US008278321B2

(12) United States Patent
Haslam

(10) Patent No.: US 8,278,321 B2
(45) Date of Patent: Oct. 2, 2012

(54) SMALL MOLECULE INHIBITION OF INTRACELLULAR TRANSPORT

(75) Inventor: David B. Haslam, St. Louis, MO (US)

(73) Assignee: Washington University, St. Louis, MO (US)

(*) Notice: Subject to any disclaimer, the term of this patent is extended or adjusted under 35 U.S.C. 154(b) by 305 days.

(21) Appl. No.: 12/645,094

(22) Filed: Dec. 22, 2009

(65) Prior Publication Data

US 2010/0159468 A1 Jun. 24, 2010

Related U.S. Application Data

(60) Provisional application No. 61/140,400, filed on Dec. 23, 2008.

(51) Int. Cl.
*A01N 43/42* (2006.01)
*A01N 43/40* (2006.01)
*A61K 31/44* (2006.01)
*A61K 31/445* (2006.01)
*C07D 221/22* (2006.01)
*C07D 221/06* (2006.01)
*C07D 211/06* (2006.01)

(52) U.S. Cl. ........... 514/290; 514/325; 546/79; 546/203

(58) Field of Classification Search .................. 514/290, 514/325; 546/79, 203
See application file for complete search history.

(56) References Cited

FOREIGN PATENT DOCUMENTS

WO  WO 2004/072046 A2 *  8/2004

OTHER PUBLICATIONS

Saenz et al. 2009 (Available online Feb. 1, 2009), "Golgicide A reveals essential roles for GBF1 in Golgi assembly and function." Nature Chemical Biology, vol. 5, No. 3, pp. 157-165.*
Reaves, B, Horn, M, and Banting, G, TGN38/41 Recycles Between the Cell Surface and the TGN: Brefeldin A Affects its Rate of Return to the TGN, Molecular Biology of the Cell, 1993, vol. 4, pp. 93-105.
Renault, L et al, Mechanism of domain closure of Sec7 domains and role in BFA sensitivity, Biochemistry, 2002, vol. 41, No. 11, pp. 3605-3612.
Renault, L, Guibert, B, and Cherfils, J, Structural snapshots of the mechanism and inhibition of a guanine nucleotide exchange factor, Nature, 2003, vol. 426, No. 6966, pp. 525-530.
Rios, RM and Bornens, M, The Golgi apparatus at the cell centre, Curr Opin Cell Biol, 2003, vol. 15, No. 1, pp. 60-66.
Rios, RM et al, GMAP-210 recruits gamma-tubulin complexes to cis-Golgi membranes and is required for Golgi ribbon formation, Cell, 2004, vol. 118, No. 3, pp. 271-272.
Robinson, MS, Adaptable adaptors for coated vesicles, Trends Cell Biol, 2004, vol. 14, No. 4, pp. 167-174.
Saenz, J, Doggett, T and Haslam, D, Identification and Characterization of Small Molecules That Inhibit Intracellular Toxin Transport, Infection and Immunity, 2007, vol. 75, No. 9, pp. 4552-4561.
Sanchez, RM et al, Prevention of the induced synthesis and secretion of group II phospholipase A2 by brefeldin A, FEBS Letters, 1993, vol. 332, No. 1-2, pp. 99-104.
Sandvig, K et al, Ricin Transport in Brefeldin A-treated Cells: Correlation between Golgi Structure and Toxic Effect, The Journal of Cell Biology, 1991, vol. 115, No. 4, pp. 971-981.
Santy, L and Casanova, J, Activation of ARF6 by ARNO stimulates epithelial cell migration through downstream activation of both Rac1 and phospholipase D, The Journal of Cell Biology, 2001, vol. 154, No. 3, pp. 599-610.
Shen, Z et al, BIG1, a brefeldin A-inhibited guanine nucleotide-exchange protein, is required for correct glycosylation and function of integrin β1, PNAS, 2007, vol. 104, No. 4, pp. 1230-1235.
Shewan, A et al, GLUT4 Recycles via a trans-Golgi Network (TGN) Subdomain Enriched in Syntaxins 6 and 16 But Not TGN38: Involvement of an Acidic Targeting Motif, Molecular Biology of the Cell, 2003, vol. 14, pp. 973-986.
Shinotsuka, C et al, Dominant-negative mutant of BIG2, an ARF-guanine nucleotide exchange factor, specifically affects membrane trafficking from the trans-Golgi network through inhibiting membrane association of AP-1 and GGA coat proteins, Biochem Biophys Res Commun, 2002, vol. 294, No. 2, pp. 254-260.
Shinotsuka, C et al, Overexpression of an ADP-ribosylation Factor-Guanine Nucleotide Exchange Factor, BIG2, Uncouples Brefeldin A-induced Adaptor Protein-1 Coat Dissociation and Membrane Tubulation, The Journal of Biological Chemistry, 2002, vol. 277, No. 11, pp. 9468-9473.
Shmuel, M et al, ARNO through Its Coiled-coil Domain Regulates Endocytosis at the Apical Surface of Polarized Epithelial Cells, The Journal of Biological Chemistry, 2006, vol. 281, No. 19, pp. 13300-13308.
Siddhanta, A et al, Fragmentation of the Golgi Apparatus, The Journal of Biological Chemistry, 2003, vol. 278, No. 3, pp. 1957-1965.
Stoorvogel, W, Oorschot, V and Geuze, H, A Novel Class of Clathrin-coated Vesicles Budding from Endosomes, The Journal of Cell Biology, 1996, vol. 132, No. 1 & 2, pp. 21-33.
Tamura, G et al, Antiviral activity of brefeldin A and verrucarin A, J. Antibiot (Tokyo), 1968, vol. 21, No. 2, pp. 160-161. Szul, T et al, Dissecting the role of the ARF guanine nucleotide exchange factor GBF1 in Golgi biogenesis and protein trafficking, Journal of Cell Science, 2007, vol. 120, pp. 3929-3940.
Traub, L, Ostrom, J and Kornfeld, S, Biochemical Dissection of AP-1 Recruitment onto Golgi Membranes, The Journal of Cell Biology, 1993, vol. 123, No. 3, pp. 561-573.
Van Dam, E and Stoorvogel, W, Dynamin-dependent Transferrin Receptor Recycling by Endosome-derived Clathrin-coated Vesicles, Molecular Biology of the Cell, 2002, vol. 13, pp. 169-182.
Van Kerkhof, P et al, Sorting nexin 17 facilitates LRP recycling in the early endosome, The EMBO Journal, 2005, vol. 24, pp. 2851-2861.
Yang, Jia-Shu et al, A role for BARS at the fission step of COPI vesicle formation from Golgi membrane, The EMBO Journal, 2005, vol. 24, pp. 4133-4143.
Zeeh, JC, et al, Dual Specificity of the Interfacial Inhibitor Brefeldin A for Arf Proteins and Sec7 Domains, The Journal of Biological Chemistry, 2006, vol. 281, No. 17, pp. 11805-11814.
Zhao, L and Haslam, D, A quantitative and highly sensitive luciferase-based assay for bacterial toxins that inhibit protein synthesis, Journal of Medical Microbiology, 2005, vol. 54, pp. 1023-1030.

(Continued)

*Primary Examiner* — Sreeni Padmanabhan
*Assistant Examiner* — Kara R McMillian
(74) *Attorney, Agent, or Firm* — Polsinelli Shughart PC

(57) ABSTRACT

The present disclosure characterizes the activity of Golgicide A (GCA), as a potent, specific and reversible small molecule inhibitor of Golgi BFA resistance factor 1 (GBF1) function. A mutant GBF1 gene that is resistant to GCA is also described. Methods of using GCA and the GCA-resistant GBF1 gene are described including methods for modulating GBF1 activity for research and therapeutic purposes. Also described are compositions incorporating a GCA-resistant GBF1.

9 Claims, 29 Drawing Sheets
(19 of 29 Drawing Sheet(s) Filed in Color)

OTHER PUBLICATIONS

Zhao, X et al, GBF1, a cis-Golgi and VTCs-localized ARF-GEF, is implicated in ER-to-Golgi protein traffic, Journal of Cell Science, 2006, vol. 119, pp. 3743-3753.

Zhao, X, Lasell, T, and Melancon, P, Localization of Large ADP-Ribosylation Factor-Guanine Nucleotide Exchange Factors to Different Golgi Compartments: Evidence for Distinct Functions in Protein Traffic, Molecular Biology of the Cell, 2002, vol. 13, pp. 119-133.

Jackson, CL Brefeldin A revealing the fundamental principles governing membrane dynamics and protein transport, Subcell Biochem, 2000, vol. 34, pp. 233-272.

Yoshida, T et al, Disruption of the Golgi apparatus by brefeldin A inhibits the cytotoxicity of ricin, modeccin, and *Pseudomonas* toxin, Exp Cell Res, 1991, vol. 192, No. 2, pp. 389-395.

Yoon, Hy, Bonifacino, JS and Randazzo, PA, In vitro assays of Arf1 interaction with GGA proteins, Methods Enzymol, 2005, vol. 404, pp. 316-332.

Adorini, L et al, Inhibition by brefeldin A of presentation of exogenous protein antigens to MHC class II-restricted T cells, Nature, 1990, vol. 346, No. 6279, pp. 63-66.

Boehm, M, Aguiblar, R and Bonifacino, J, Functional and physical interactions of the adaptor protein complex AP-4 with ADP-ribosylation factors (ARFs), The EMBO Journal, 2001, vol. 20, No. 22, pp. 6265-6276.

Boman, A et al, A Family of ADP-Ribosylation Factor Effectors That Can Alter Membrane Transport through the trans-Golgi, Molecular Biology of the Cell, 2000, vol. 11, pp. 1241-1255.

Bonifacino, J and Glick, B, The Mechanisms of Vesicle Budding and Fusion, Cell, 2004, vol. 116, pp. 153-166.

Cherfils, J and Melancon, P, On the action of Brefeldin A on Sec7-stimulated membrane-recruitment and GDP/GTP exchange of Arf proteins, Biochemical Society Transactions, 2005, vol. 33, Pt. 4, pp. 635-638.

Citterio, C et al, Unfolded protein response and cell death after depletion of brefeldin A-inhibited guanine nucleotide-exchange protein GBF1, PNAS, 2008, vol. 105, No. 8, pp. 2877-2882.

Claude, A et al, GBF1: A Novel Golgi-associated BFA-resistant Guanine Nucleotide Exchange Factor That Displays Specificity for ADP-ribosylation Factor 5, The Journal of Cell Biology, 1999, vol. 146, No. 1, pp. 71-84.

Cohen, LA et al, Active Arf6 Recruits ARNO/Cytohesin GEFs to the PM by Binding Their PH Domains, Molecular Biology of the Cell, 2007, vol. 18, pp. 2244-2253.

Cole, NB et al, Golgi Dispersal during Microtubule Disruption: Regeneration of Golgi Stacks at Peripheral Endoplasmic Reticulum Exit Sites, Molecular Biology of the Cell, 1996, vol. 7, pp. 631-650.

De Matteis, MA and Morrow, JS, ADP-Ribosylation Factor (AFR) as Regulator of Spectrin Assembly at Golgi Complex, Methods in Enzymology, 2001, vol. 329, pp. 405-416.

Dell'Angelica, E et al, GGAs: A Family of ADP Ribosylation Factor-binding Proteins Related to Adaptors and Associated with the Golgi Complex, The Journal of Cell Biology, 2000, vol. 149, No. 1, pp. 81-93.

Campli, A et al, Morphological Changes in the Golgi Complex Correlate With Actin Cytoskeleton Rearrangements, Cell Motility and the Cytoskeleton, 1999, vol. 43, pp. 334-348.

Doms, R et al, Brefeldin A Redistributes Resident and Itinerant Golgi Proteins to the Endoplasmic Reticulum, The Journal of Cell Biology, 1989, vol. 109, pp. 61-72.

Donaldson, JG, Honda A, and Weigert R, Multiple activities for Arf1 at the Golgi complex, Biochim Biophys Acta, 2005, vol. 44, No. 3, pp. 364-373.

Donaldson, JG and Jackson, CL, Regulators and effectors of the ARF GTPases, Curr. Opin. Cell Biol., 2000, vol. 12, No. 4, pp. 475-482.

Doray, B et al, Cooperation of GGAs and AP-1 in Packaging MPRs at the Trans-Golgi Network, Science, 2002, vol. 297, pp. 1700-1703.

Egea, G, Lazaro-Dieguez, F and Vilella M, Actin dynamics at the Golgi complex in mammalian cells, Curr. Opin. Cell Biol., 2006, vol. 18, No. 2, pp. 168-178.

Meskini, RE et al, A Signal Sequence is Sufficient for Green Fluorescent Protein to Be Routed to Regulated Secretory Granules, Endocrinology, 2001, vol. 142, No. 2, pp. 864-873.

Garcia-Mata, R et al, ADP-Ribosylation Factor/COPI-dependent Events at the Endoplasmic Reticulum-Golgi Interface Are Regulated by the Guanine Nucleotide Exchange Factor GBF1, Molecular Biology of the Cell, 2003, vol. 14, pp. 2250-2261.

Ghosh, P and Kornfeld, S, The GGA proteins: key players in protein sorting at the trans-Golgi network, Eur. J. Cell Biol., 2004, vol. 83, No. 6, pp. 257-262.

Godi, A et al, ADP ribosylation factor regulates spectrin binding to the Golgi complex, PNAS, 1998, vol. 95, pp. 8607-8612.

Guillemain, I and Exton, J, Effects of brefeldin A on phosphatidylcholine phospholipase D and inositolphospholipid metabolism in HL-60 cells, Eur. J. Biochem, 1997, vol. 249, pp. 812-819.

Helms, JB and Rothman, JE, Inhibition by brefeldin A of a Golgi membrane enzyme that catalyses exchange of guanine nucleotide bound to ARF, Nature, 1992, vol. 360, No. 6402, pp. 352-354.

Hirschberg, K et al, Kinetic Analysis of Secretory Protein Traffic and Characterization of Golgi to Plasma Membrane Transport Intermediates in Living Cells, The Journal of Cell Biology, 1998, vol. 143, No. 6, pp. 1485-1503.

Holloway, ZG, et al, Activation of ADP-ribosylation factor regulates biogenesis of the ATP7A-containing trans-Golgi network compartment and its Cu-induced trafficking, Am J. Physiol. Cell Physiol., 2007, vol. 293, pp. C1753-C1767.

Hunziker, W, Whitney, JA and Mellman, I, Selective inhibition of transcytosis by brefeldin A in MDCK cells, Cell, 1991, vol. 67, No. 3, pp. 617-627.

Jones, HD, Moss, J, and Vaughan, M, BIG1 and BIG2, brefeldin A-inhibited guanine nucleotide-exchange factors for ADP-ribosylation factors, Methods Enzymol., 2005, vol. 404, pp. 174-184.

Kahn, R et al, Nomenclature for the human Arf family of GTP-binding proteins: ARF, ARL, and SAR proteins, J. Cell Biol., 2006, vol. 172, No. 5, ppl. 645-650.

Kawamoto, K et al, GBF1, a guanine nucleotide exchange factor for ADP-ribosylation factors, is localized to the cis-Golgi and involved in membrane association of the COPI coat, Traffic, 2002, vol. 3, No. 7, pp. 483-495.

Ktistakis, N et al, Phospholipase D is present on Golgi-enriched membranes and its activation by ADP ribosylation factor is sensitive to brefeldin A, PNAS, 1995, vol. 92, pp. 4952-4956.

Lazaro-Dieguez, F et al, Actin filaments are involved in the maintenance of Golgi cisternae morphology and intra-Golgi pH, Cell Motil Cytoskeleton, 2006, vol. 63, No. 12, pp. 778-791.

Lefrancois, S and McCormick, PJ, The Arf GEF GBF1 is required for GGA recruitment to Golgi membranes, Traffic, 2007, vol. 8, No. 10, pp. 1440-1451.

Lin, Wei-Hsung et al, Recognition of Substrates by Tyrosylprotein Sulfotransferase, The Journal of Biological Chemistry, 1992, vol. 267, No. 5, pp. 2876-2879.

Lippincott-Schwartz, J et al, Brefeldin A's effects on endosomes, lysosomes, and the TGN suggest a general mechanism for regulating organelle structure and membrane traffic, Cell, 1991, vol. 67, No. 3, pp. 601-616.

Lippincott-Schwartz, J et al, Rapid redistribution of Golgi proteins into the ER in cells treated with brefeldin A: evidence for membrane cycling from Golgi to ER, Cell, 1989, vol. 56, No. 5, pp. 801-813.

Liu, Wei et al, ArfGAP1 dynamics and its role in COPI coat assembly on Golgi membranes of living cells, The Journal of Cell Biology, 2005, vol. 168, No. 7, pp. 1053-1063.

Mallard, F et al, Early/recycling endosomes-to-TGN transport involves two SNARE complexes and a Rab6 isoform, The Journal of Cell Biology, 2002, vol. 156, No. 4, pp. 653-664.

Manolea, F et al, Distinct Functions for Arf Guanine Nucleotide Exchange Factors at the Golgi Complex: GBF1 and BIGs are Required for Assembly and Maintenance of the Golgi Stack and trans-Golgi Network, Respectively, Molecular Biology of the Cell, 2008, vol. 19, pp. 523-535.

Mansour, S et al, p200 ARF-GEP1: A Golgi-localized guanine nucleotide exchange protein whose Sec7 domain is targeted by the drug brefeldin A, PNAS, 1999, vol. 96, pp. 7968-7973.

Monetta, P et al, Rab1b Interacts with GBF1 and Modulates both ARF1 Dynamics and COPI Association, Molecular Biology of the Cell, 2007, vol. 18, pp. 2400-2410.

Mossessova, E, Corpina, RA, and Goldberg, J, Crystal structure of ARF1*Sec7 complexed with Brefeldin A and its implications for the guanine nucleotide exchange mechanism, Mol. Cell, 2003, vol. 12, No. 6, pp. 1403-1411.

Niehrs, C and Huttner, W, Purification and characterization of tyrosylprotein sulfotransferase, The EMBO Journal, 1990, vol. 9, No. 1, pp. 35-42.

Niu, Ting-Kuang et al, Dynamics of GBF1, a Brefeldin A-Sensitive Arf1 Exchange Factor at the Golgi, Molecular Biology of the Cell, 2005, vol. 16, pp. 1213-1222.

Orci, L et al, Brefeldin A, a drug that blocks secretion, prevents the assembly of non-clathrin-coated buds on Golgi cisternae, Cell, 1991, vol. 64, No. 6, pp. 1183-1195.

Pacheco-Rodriguez, G, Moss, G, and Vaughan, M, BIG1 and BIG2: brefeldin A-inhibited guanine nucleotide-exhcnage proteins for ADP-ribosylation factors, Methods Enzymol., 2002, vol. 345, pp. 397-404.

Pasqualato, S et al, The structural GDP/GTP cycle of human Arf6, EMBO reports, 2001, vol. 2, No. 3, pp. 234-238.

Peyroche, A et al, Brefeldin A acts to stabilize an abortive ARF-GDP-Sec7 domain protein complex: involvement of specific residues of the Sec7 domain, Mol. Cell, 1999, vol. 3, No. 3, pp. 275-285.

Presley, JF et al, Dissection of COPI and Arf1 dynamics in vivo and role in Golgi membrane transport, Nature, 2002, vol. 417, No. 6885, pp. 187-193.

Prydz, K et al, Effects of Brefeldin A on Endocytosis, Transcytosis and Transport to the Golgi Complex in Polarized MDCK Cells, The Journal of Cell Biology, 1992, vol. 119, No. 2, pp. 259-272.

Reaves, B and Banting, G, Perturbation of the Morphology of the trans-Golgi Network following Brefeldin A Treatment: Redistribution of a TGN-specific Integral Membrane Protein, TGN38, The Journal of Cell Biology, 1992, vol. 116, No. 1, pp. 85-94.

* cited by examiner

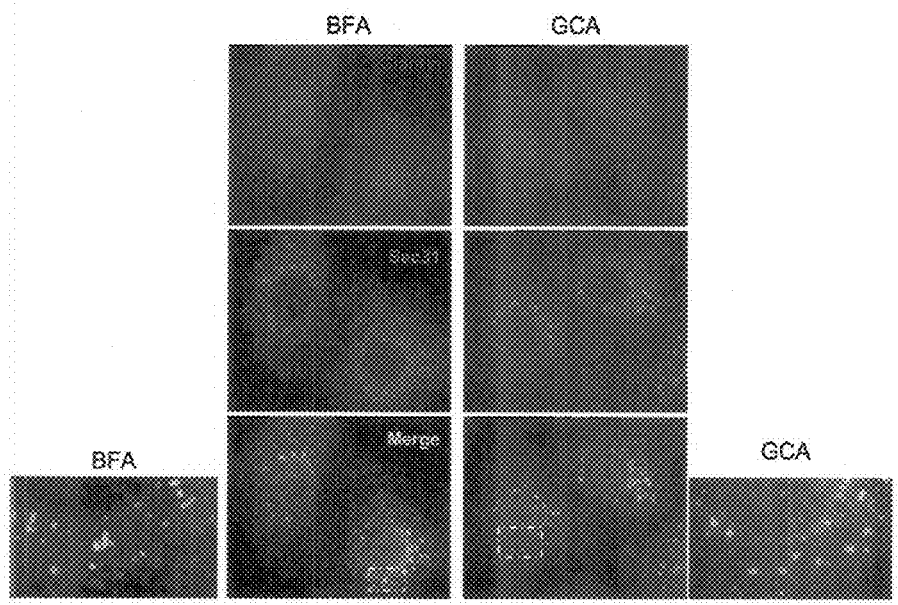

Figure 4. BFA and GCA disperse the medial-Golgi marker giantin to a partially punctate pattern adjacent to ERES. Vero cells were treated with BFA (10 mg/ml) or GCA (10 mM) for 60 mins then fixed and labeled with antibodies against giantin (red) or Sec31 (green). Both compounds cause giantin redistribution into a hazy and punctate pattern. Giantin-positive punctate structures are closely approximated to Sec31-labeled ERES.

Fig. 4

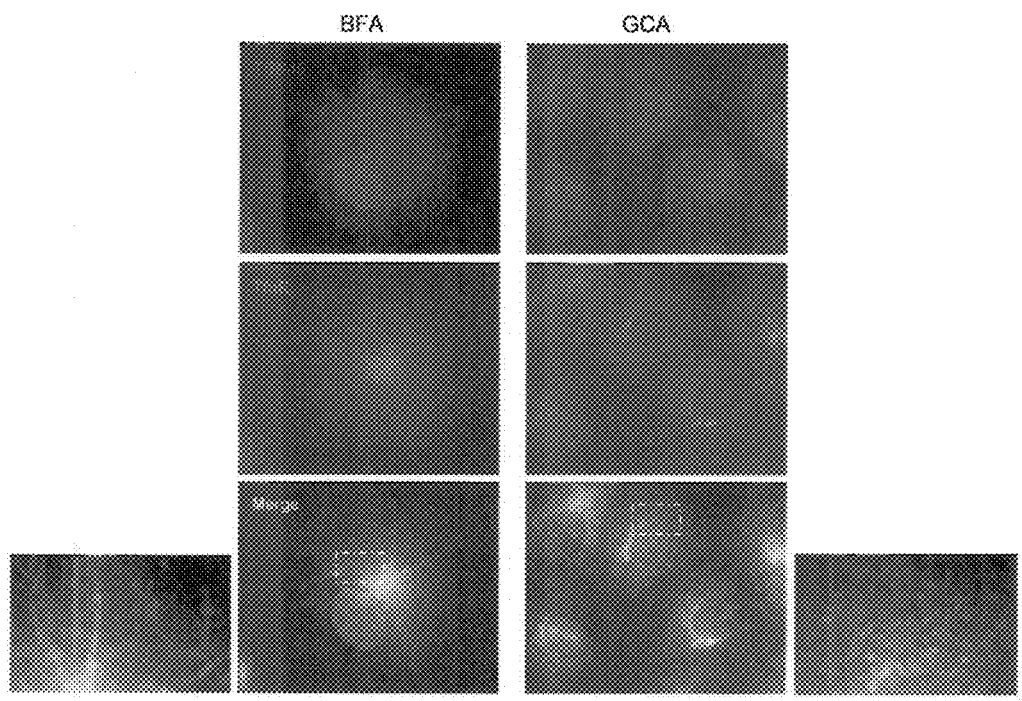

Figure 5. BFA and GCA have distinct effects on the TGN and endosomes. Vero cells were treated with BFA (10 μg/ml) or GCA (10 μM) for 15 mins then fixed and labeled with antibodies against TGN46 (red) or transferrin receptor (Tfn; green). Whereas BFA treatment resulted in tubulation and partial overlap of TGN and recycling endosomes, GCA caused both to disperse into punctate structures that did not co-localize.

Fig. 5

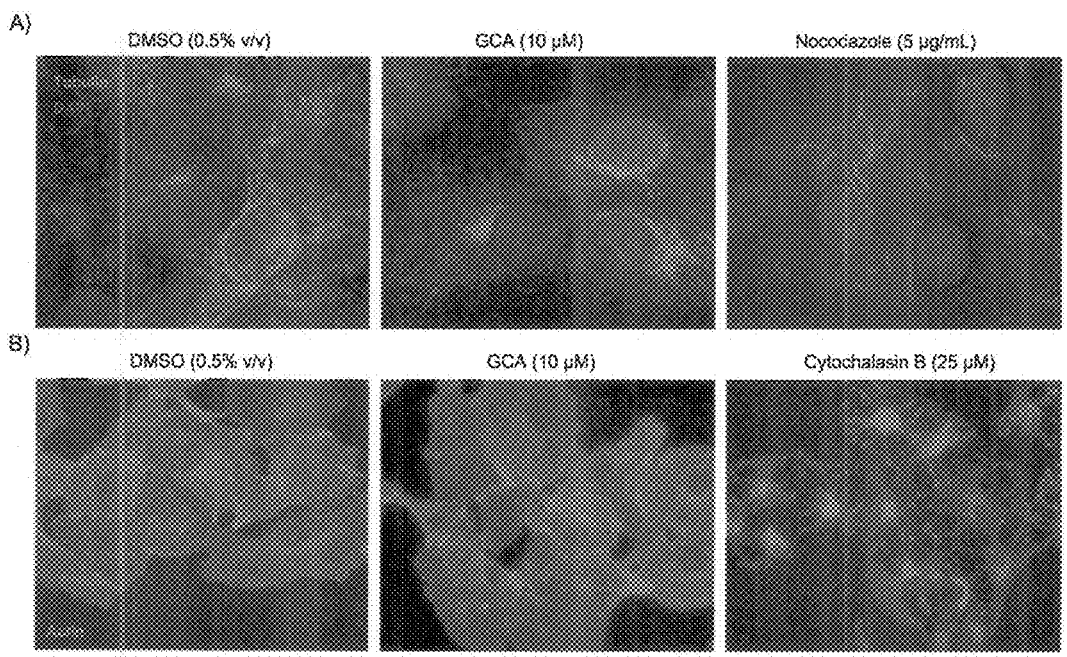

Figure 6. GCA does not affect microtubular or actin cytoskeletons. (a) Vero cells were treated for 30 min at 37°C with DMSO, GCA, or nocodazole at the indicated concentrations prior to fixation and immunostaining, as described in Supplemental Methods. At 10 μM, GCA had no observable effects on microtubules, while nocodazole, an inhibitor of microtubule polymerization, produced drastic morphological effects. (b) Vero cells were treated with DMSO, GCA, or cytochalasin B at the indicated concentrations and developed for immunofluorescence, as in (a). GCA showed no effects on actin microfilaments compared to DMSO-treated cells, while the actin-depolymerizing agent cytochalasin B induced significant changes to actin morphology.

Fig. 6

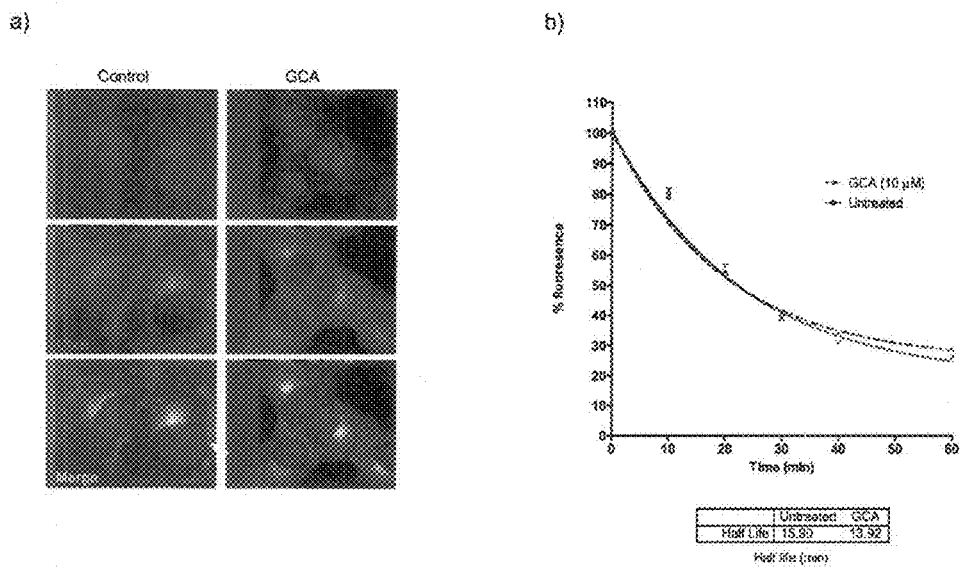

Figure 7. GCA does not affect transport through recycling endosomes. (a) GCA treatment maintains endocytic transport to recycling endosomes. Vero cells were treated for 15 min with DMSO (control; 0.5% v/v) or GCA (10 µM), then incubated with AlexaFluor 594-labeled CtxB (1 µg/mL) and 488-labeled Tfn (1 µg/mL) for 1 h at 4°C in serum-free medium prior to shifting cells to 19°C for an additional hour. Cells were then fixed and developed for immunofluorescence. GCA, similar to control cells, did not affect CtxB trafficking to a juxtanuclear, Tfn-positive recycling endosome compartment. Blue, nuclei. (b) GCA treatment does not affect the kinetics of transferrin recycling. Vero cells were left untreated or were treated with GCA for 1 h. Cells were allowed to internalize AlexaFluor-488 labeled transferrin for 60 min. Fresh media containing quenching anti-AlexaFluor-488 antibodies were added, and at various times the cells were harvested and fixed (see Supplementary Methods). Each time point was performed in triplicate, and the mean and standard deviation of each is presented. All data were fitted by nonlinear regression assuming one phase decay, and half-lives (in min; inset) were calculated using GraphPad Prism. CtxB, cholera toxin B subunit; Tfn, transferrin.

Fig. 7

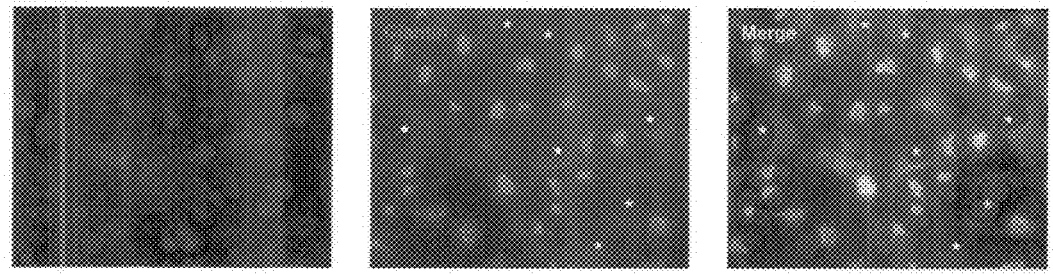

Figure 13. Transduction with GBF1-ML is less than 100% efficient. Vero cells were transduced with GBF1-ML to be used in Arf1 activation assay (Figure X). An aliquot of cells was seeded into a slide chamber. Simultaneous with cells used for the the Arf1-GTP pulldown assay, these cells were treated with GCA for 1 hr then fixed and labeled with antibodies against HA (GBF1; red) or giantin (green). Nuclei were labeled with DAPI. GBF1 expression varies from cell to cell, with approximately 85% of cells expressing detectable GBF1. These cells are protected from the effects of GCA, while approximately 15% express low or undetectable GBF1 and are not protected from GCA (white asterix).

Fig. 13

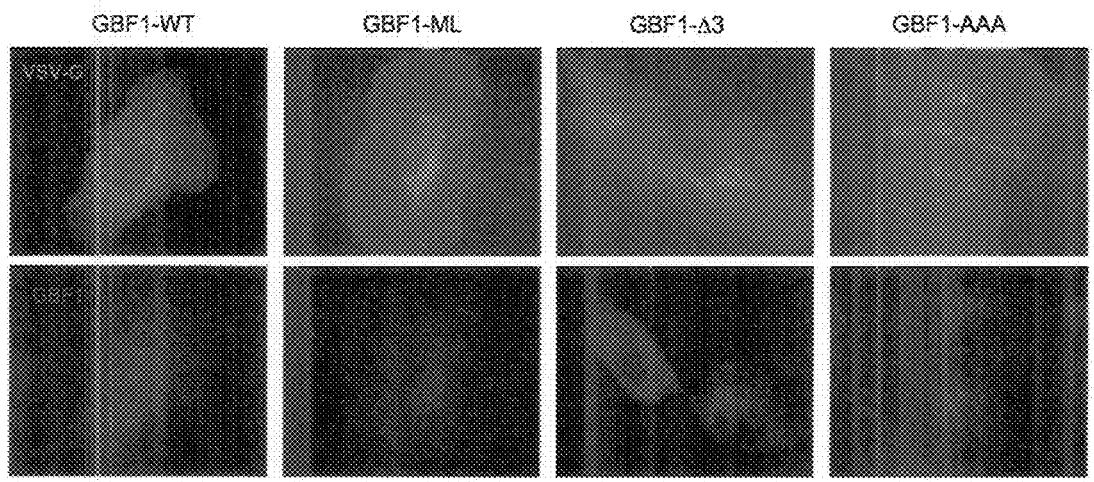
Figure 16. Expression of GBF1-ML or GBF1-loop mutants results in resistance of the effects of GCA on ts VSVG-GF

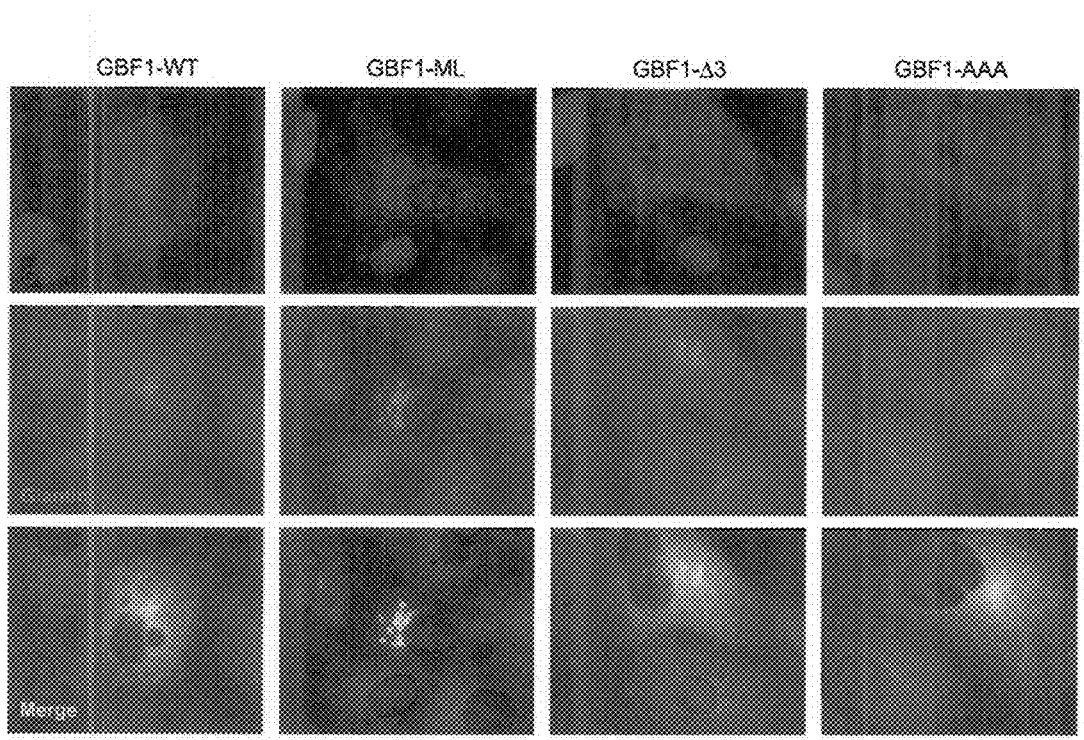

Figure 17. Expression of GBF1-ML but not GBF1-loop mutants results in resistance to the effects of BFA on Golgi morphology. Vero cells were transiently trasfected with GBF1-WT, or a GBF1-ML, GBF1-Δ3, GBF1-AAA. Two days later the cells were treated for 60 mins with BFA (10 μg/ml) then fixed and labeled with anti-HA (GBF1; red) or anti-giantin antibodies (green). Cells expressing GBF1-ML, but not GBF1-WT, GBF1-Δ3, or GBF1-AAA are resistant to the effects of BFA on Golgi morphology.

Fig. 17

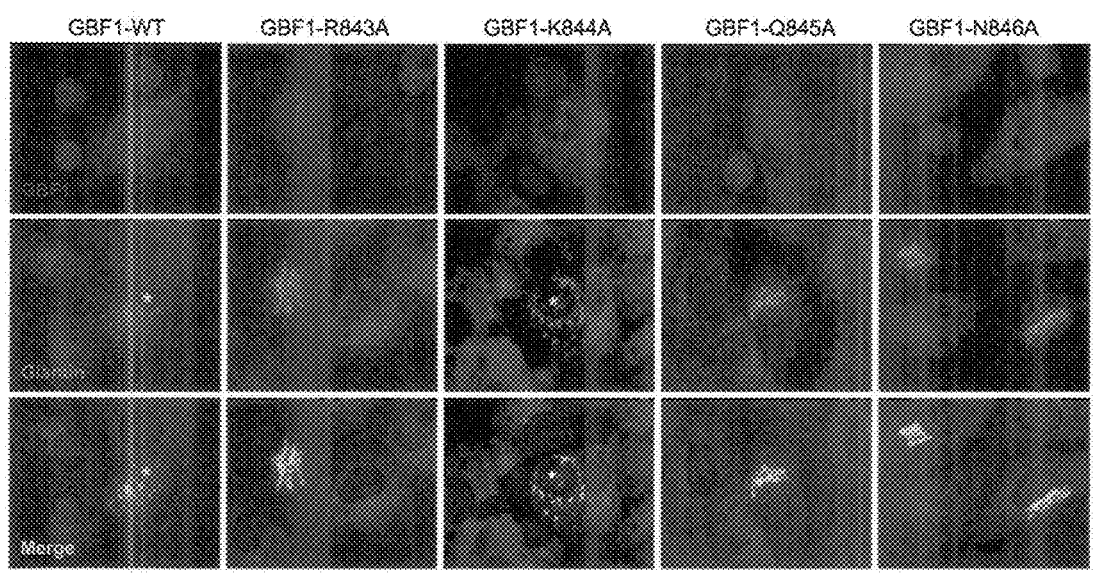

Figure 18. Expression of GBF1-M<sub>L</sub> but not GBF1-loop mutants results in resistance to the effects of BFA on Golgi morphology. Vero cells were transiently trasfected with GBF1-WT, or a GBF1-R843A, GBF1-K844A, GBF1-Q845A, or GBF1-N846A. Thirty six hours later the cells were treated for 60 mins with GCA (10mM) then fixed and labeled with anti-HA epitope (GBF1; red) or giantin (green). Cells expressing GBF1-R843A, GBF1-Q845A, and GBF1-N846A are resistant to the effects of GCA on Golgi morphology, whereas cells expressing GBF1-WT and GBF1-K844A are only partially protected. White asterix mark the partially protected cells.

Fig. 18

Hamster GBF1 M830L mutant
(mutations marked in bold/underline)

cDNA Sequence:

```
ATGGTGGATAAGAATATTTACATCATTCAAGGAGAAATTAACATTGTTGTTGGCGCCATCAAACGAAATG
CACGATGGAGCACCCATATACCACTGGATGAAGAACGGGATCCTCTGCTGCACAGTTTCAGTCATCTAAA
GGAGGTCTTAAACAGTGTAACGGAACTCTCAGAGATTGAGCAAATGTATTCCTTCGTCCATTTCTGGAA
GTTATTCGCTCTGAAGATACCACTGGTCCTATCACTGGCCTGGCGCTCACCTCTGTCAACAAATTCCTGT
CCTATGCACTCATAGATCCAACTCATGAGGGCACAGCAGAGGGCATGGAGAACATGGCAGATGCTGTCAC
TCATGCCCGTTTTGTGGGTACAGACCCTGCCAGCGATGAAGTTGTCCTGATGAAAATCCTCCAGGTTCTT
CGAACTCTGTTGCTAACCCCAGTGGGTACCCACTTAACAAATGAATCTGTGTGTGAGATTATGCAGTCTT
GCTTCCGGATTTGCTTTGAAATGAGGCTTAGTGAGTTATTGAGAAAATCCGCAGAGCACACTCTCGTAGA
CATGGTGCAGCTGCTCTTCACAAGGTTACCTCAGTTTAAAGAAGAACCCAAGAGCTATGTGGAACCAAC
ATGAAGAAGCTGAAAATGAGAGCGGGAGGCATGAGCGACTCATCCAAGTGGAAAAAGCAGAAAAGGATCCC
CTCGGCGCCCCGGTCACATGACCAGAGTCACACCCAGGTTCAGAGCTGCCCGCCCCAAATGGAGCCCACCTT
ATCCTGTAACCTCACCAGTGGCATGCCTTTCATTGATGTGCCCTCATCCATCTCCTCTGCAAGTTCAGAA
GCTGCCCTCAGCAGTGGTCAGTCCCTGTACAGACAGTGGCCTGGAATTATCCTCCCAGACCACCTCCAAGG
AGGACCCTCACTGACCCTAGAGCAAGCTGGTTCCCCAAGGGAAAGCACAACCACAGAGTCTGGGAGCAATGA
GATAGGAGTTTCCGATCAGCTTGACCCTCAGGAAGGGTCCCATGTGGAAAAGGCCCAGTCAGCATCGGTG
GAATCTATCCCTGAAGTGTTGGAGGAGTGCACATCTCCTCCTGACCACTCTGCCTCTGTCCATGACATGG
ATTATGTCAATCCCCGGGGTGTTCGCTTCACACAGTCCCTCCCAGAAGGAAGGCACAGCTTTGGTTCCTTA
TGGTCTTCCTTGCATCGAGAGCTCTTCCGCTTCCTTATCTCCCTCACAAACCCACATGACCGCCACAAC
TCAGAGGGTATGATCCACATGGGACTGCATTTGCTGACAGTGGCTCTGGAGTCAGCCCCTGTAGCCCAGT
GCCAGACCCTCTTGGGTCTCATCAAGGATGAGATGTGTCGCCCACTTATTCCAGCTACTCAGTGTAGAGCG
ATTGAACCTGTATGCTGCTTCCCTACGGGGTATGCTTCTTACTCTTTGAGAGCATGCCGGGAGCACCTCAAG
TTCCAATTAGAGATGTACATGAAAAAACTCATGGAGATCATCACTGTTGAAAACCCCAAGATGCCCTTATG
AGATGAAGGAGATGGCACTGGAGGCCATCGTGCAGCTCTGGCGCATCCCCAGCTTTGTCACTGAGCTCTA
TATCAACTACGATTGTGACTACTACTGCGCCAACCTCTTTGAAGACCTCACTAAGCTGCTGTCCAAGAAT
GCCTTTCCTGTGTCTGGTCAACTTTATACCACACACCTACTGTCCCTTGATGCCCTGTTGACGGTTATTG
ACAGCACTGAGGCTCACTGTCAAGCCAAAGTCCTCAACACTCTTACCCAGCAAGAGAAGAAGGAGACATC
CAGACCCAGCTACGAGGCAGTGGATAGCACCCAAGAAGCAAACAGTACTGAAAGAGCCACCATTGATGGG
AAAGCCACAGGCATGGCCTCAGATGCCCTAGGCCTTCATCTTCAAAGTGGAGGATGGCTGTCAGCGAGC
ATGGGAAGCCAAGATGCAATGATGTGGAAGAAGCTGGTGACTCTGGGGCTGACAAAAAGTTTACCGGGAA
GCCGGCCTCGGATTTTCCTGTCTTCTGCCAGATCCACGGGAACTAATGAAATTAAGAACAAAAAGAGGCTG
CTGATCACTGGCACAGAGCAGTTCAATCAGAAACCCAAGAAGGGCATCCAGTTTCTACAGGAAAAGGGTC
TCCTTACCATCCCAATGGATAACACAGAGGTGGCCCAGTGGCTCCGAGAGAACCCTCGGCTAGACAAGAA
AATGATTGGGGAGTTTGTGAGTGACCGAAAAAACATTGACCTGTTGGAGAGTTTTGTGAGCACCTTCAGC
TTTCAGGGTCTACGGCTTGATGAAGCTCTCCGACTCTACCTGGAAGCCTTCCGTTTGCCCGGGAAGCAC
CAGTTATTCACAGGTTGCTGGAGGCATTCACAGAGCACTGGAGGAGTTGTAATGGCTCCCCATTTGCCAA
TAGCGATGCCTGCTTTGCCCTGGCCTATGCTGTCATCTGGCTTAATACTGACCAGCATAACCACAATGTC
```

Fig. 22A

```
CGCAAACAGAATGTACCCATGACTCTGGAGGAGTTTCGAAAAAACCTAAAAGGTGTGAATGGAGGCAAGG
ACTTTGAGCAAGACATCCTGGAGGACATGTACCATGCCATCAAGAATGAGGAAATCGTGATGCCCGAGGA
ACAGACAGGCCTGGTTCGTGAGAACTATGTGTGGAGTGTGCTGCTGCACCGAGGTGCCACCCCTGAGGGT
ATATTCCTTCGTGTACCTCCTGGCAGCTATGATCTTGACCTCTTCACTATGACCTGGGGCCCAACTATTG
CTGCTCTCTCTTATGTCTTTGATAAAAGCATTGAGGAGACCATCATCCAGAAAGCCATCTCAGGTTTCAG
GAAGTGTGCCATGATCTCTGCCCACTATGGCCTCAGCGATGTGTTTGACAATCTCATCATCTCTTTGTGC
AAGTTCACAGCTCTCAGTAGTGAGTCTATTGAGAACCTTCCCACTGTGTTTGGAAGCAACCCTAAAGCTC
ACATTGCAGCCAAGACAGTATTCCACTTGGCCCATCGTCATGGTGACATCCTTCGGGAGGGCTGGAAGAA
TATCATGGAGGCTGTGCTGCAACTCTTCCGTGCTCAACTTTTACCCCAGGCTATGGTGGAGGTAGAAGAT
TTTGTGGATCCCAATGCTAAGATCTCTCTACAGCGCGGAGGAGATGCCATCAAACCGAGGAGAGTCATCGG
TACTTAGCTTTGTGAGCTGGCTGACGTTGAGTGGTCCTGAGCAGTCTAGTGTACGGGGCCCCTCCACAGA
GAACCAGGAGGCCAAGAGAGTGGCCTTGGACTGTATCAAGCAATGTGACCCGAAAAAAATGATCACGAA
AGCAAGTTCCTTCAGCTGGAATCATTGCAGGAGCTCATGAAGGCTTTGGTCTCAGTGACAGCAGATGAAG
AGACATACGATGAAGAGGATGCTGCTTTCTGTCGGAGATGCTGCTGAGGATTGTGTTGGAGAACAGGGA
CCGTGTGGGCTGTGTATGGCAGACTGTTAGAGACCATCTATACCACTTATGTGTTCAGGCACAAGATTTC
TGCTTTCTCGTGGAGCGGGCAGTGGTGGGGCTGCTACGCCTCGCGGATTCGGCTACTCCGGAGAGAGAGA
TCAGTGGCCAGGTCCTGCTGTCCCTGCGCATCTTGTTACTGATGAAGCCCAGCGTGCTGTCCAGGGTCAG
CCTACCAGGTTGCCTACGGGCTCCATGAACTCCTCAAGACCAATGCAGCCAACATCCACTCGGGTGACGAC
TGGGCCACCCTCTTCACATTGCTGGAGTGTATTGGCTCAGGGCGTGAAGCCTCCAGATGCTCTACAGGCCA
CAGCCAGGGCTGATGCTCCTGATGCTGGAGCGCAGTCAGACAGTGAGCTCCCATCCTACCATCAAAATGA
TGTCAGCCTAGACCGAGGGTACACTTCCGACTCAGAAGTCTACACTGACCATGGCAGGCCTGGCAAGATA
CACCGATCTGCCACAGATGCTGATATGGTCAACAGTGGTTGGTTAGTGGTGGGGAAGGATGACATTGATA
ACTCCAAAGCAGGAGCAGGGCTCAGCAGGCCCAGCCCTTCACCCCTGGTTAATCAATATAGCCTCACAGT
GGGCCTGGACCTGGGACCACATGACACTAAGTCCCTGCTCAAGTGTGTGCGGAATCACTGTCCTTCATTGTT
CGTGATGCTGCTCACATCGACCCCTGACAACTTTGAACTCTGTGTCAAGACTCTCCGCATCTTTGTAGAGG
CCAGTCTGAATGGTGGGTGCAAATCCCAGGATAAACGTGGCAAGAGTCACAAATATGACAGCAAAGGGAA
CCGCTTCAAGAAAAAACCGAAGGAGGGCTCAGTGCTTCGGCGGCCCCGAACCTCCAGCCAGCATGGCACT
CGGGGTGGACATAGTGATGAGGAAGAGGATGAAGGAGTGCCTGCCAGCTACCATACGGTGTCTTTACAGG
TCAGTCAGGACTTGCTGGACCTGATGCACACCCTGCACACTGGGCAGCCTCTATCTACAGCTCATGGGC
AGAGGAGCAGCGCCACCTGGAGTCAGGTGGCCGAAAGATTGAAGCTGACTCACGCACCCTCTGGGCCCAC
TGCTGGTGCCCTTTATTGCAAGGCATCGCCTGCTTGTGCTGTGATGCCCGGCGCCAAGTGCGGATGCAGG
CCCTGACGTATCTGCAGCGAGCACTTCTGGTGCATGACCTACAAAGCTAGATGCCCTGGAATGGGAGTC
CTGCCTTTAACAAGGTGCTGTTTCCTCTACTGACCAAGCTGTTAGAAAATATCAGCCCTGCAGATGTGGGT
GGGATGGAGGAGACCCGGATGAGGGCTTCCACGCTGCTCTCAAAGGTCTTCCTGCAGCACCTGTCCCCTC
TGCTGTCGCTGTCCACCTTTGCTGCCCTGTGGCTCACCATCCTGGACTTCATGGACAAGTACATGCATGC
AGGCTCCAGTGATTTGCTGTCAGAAGCAATCCCTGAGTCCCTGAAAACATGCTCCTGGTGATGGACACG
GCCGAGATCTTCACAGTGCAGATGCGAGAGGAGGCAGCCCCTCTGCCCTCTGGGAGATCACCTGGGAGC
GCATTGATTGCTTTTTGCCACACTTACGTGACGAGCTCTTCAAGCAGACTGTCATCCAGGACCCCATGCC
CACGGAACCTCACAGCCAAAACGCTCTGGCCTCCACCCACCTGACCCCTGCTGCTGGTGACCCCGGCCAT
CTACCTTCCCCAGAGATACCCTCAGAAGTGGGGGCCTGTGACTCAGAGAAGCCTGAGGGTACCCGAGCCA
```

Fig. 22B

```
CCAGCAGCAGCTCTCCGGGATCACCAGTGGCCTCCAGCCCCAGTAGACTGAGTCCTTCCCCAGAGGGACC
TCCCCCATTGGCCCAGCCCCCACTAATCCTGCAGCCCCTGACTTCCCCGCTGCAGGTGGGCGTGCCACCC
ATGGCTCTGCCCATTATCCTGAACCCTGCACTCATCGAGGCCACCTCTCCCGGTGCCTGTCTTGTCCACTC
CCCGTCCTACAGACCCTATTCCCACCTCTGAAGTCAAC
```

Fig. 22C

Peptide sequence:

```
MVDKNIYIIQGEINIVVGAIKRNARWSTRHIPLDEERDPLLASFSHLKEVLNSVTELSEIEPNVFLRPPLE
VIRSEDTTGPITGLALTSVNKFLSYALIDPTHEGTAEGMEKMADAVTHARPVGTDPASDEVVLMKILQVL
KTLLLTPVGTRLTNESVCEIMQSCPRICFEMRLSELLRKSAEHTLVDMVQLLFTRLPQFKEEPKSYVGTN
MKKLRMRAGGMSDSSKWKKQKRSPRPPRBMTRVTPGSELPAPNGATLSCNLTSGMPFIDVPSSISSASSE
AASAVVSPCTDSGLELSSQTTSKEDLTDLEQAGSPRESTTTESGSNRIGVSDQLDPQEGSNVEEAQSASV
ESIPEVLEECTSPPIHSASVHDMDYVNPRGVRFTQSSQREGTALVPYGLPCIRELFRFLISLTNSHDRHN
SEGMIRMGLHLLTVALESAPVAQCQTLLGLIKDEMCRHLPQLLSVERLNLYAASLRVCFLLPESMREHLK
PQLEMYMKKLMEITTVENPKMPYEMKEMALEAIVQLWRIPSFVTELYINYDCDYYCANLFEDLTKLLSKN
AFPVSGQLYTTHLLSLDALLTVIDSTEAHCQAKVLNTLTQQEKKETSRPSYEAVDSTQEANSTERATIDS
KATGMASDALGLHLQSGGWLSAEHGKPRCNDVEEAGDSGADKKFTRKPFRPSCLLPDPRELIEIKNKKKL
LITGTEQFNQKPKKGIQFLQEKGLLTIPMDNTEVAQNLRENPRLDKKMIGEPVSDRKNIELLESFVSTFS
PQGLRLDEALRLYLEAFKLPGEAPVIHRLLEAFTERWRSCNGSPFANSDACFALAYAVILLNTDQEMHNV
RKQNYPMTLEEPRKNLKGVNGGKDPEQDILEDMYHAIKNEEIVMPEEQTGLVRENYWMSVLLHRGATPEG
IFLRVPPGSYDLDLFDMTNGPTIAALSYVPDKSIEETIIQKAISGFRKCAMISAHYGLSDVPDNLIISLC
KFTALSSESIENLPTVPGSNPKAHIAAKTVPHLAHEHGDILEEGWKNIMEAVLQLFRAQLLPQAMVEVED
FVDPNGKISLQREEMPSNRGESSVLSFVSNLTLSGPEQSSVRGPSTENQEAKRVALDCIKQCDPEKMITE
SKFLQLESLQELMKALVSVTADEETYDEEDAAFCLEMLLRIVLENRDRVGCVWQTVRDHLYHLCVQAQDP
CFLVERAVVGLLRLAIRLLRREEISGQVLLSLRILLLMKPSVLSRVSHQVAYGLHELLKTRAANIRSGDS
WATLPTLLECIGSGVKPPDALQATARADAPDAGAQSDSELPSYHQNDVSLERGYTSDSEVYTDHGRPGKI
HRSATDADMVNSGWLVVGKDDIDNSKAGAGLSRPSPSPLVNQYSLTVGLDLGPHDTKSLLKCVESLSFIV
RDAAHITPDNFELCVRTLRIFVEASLNGGCKSQDKRGKSRRYDSKGNRFKKKPKEGSVLRRPKTSSQHGT
RGGHSDEKEDSGVPASYHTVSLQVSQHLLELMHTLHTRAASIYSSWAEEQEHLESGGRKIEADSRTLWAH
CWCPLLQGIACLCCDARRQVRMQALTYLQRALLVHDLQKLDALEWESCFNKVLFPLLTKLLENISPADVG
GMEETRMRASTLLSKVFLQHLSPLLSLSTFAALNLTILDFMDKYMHAGSSDLLSEAIPESLKNMLLVMDT
AEIFRSADARGNSPSALWEITWERIDCFLPRLRDELFKQTVIQDPMPTEPRSQNALASTMLTPAACDPGN
LPSPEIPSEVGACDSEKPEGTRATSSSSPGSPVASSPSRLSPSPEGPPPLAQPPLILQPLTSPLQVGVPP
MALPIILNPALIEATSPVPLLSTPRPTDPIPTSEVN
```

Fig. 23

Hamster GBF1 E792K mutant
(mutations marked in bold/underline)

cDNA Sequence

ATGGTGGATAAGAATATTTACATCATTCAAGGAGAAATTAACATTGTTGTTGGCGCCATCAAACGAAATG
CACGATGGAGCACCCATATACCACTGGATGAAGAACGGGATCCTCTGCTGCACAGTTTCAGTCATCTAAA
GGAGGTCTTAAACAGTGTAACAGAACTCTCAGAGATTGAGCCAAATGTATTCCTTCGTCCATTTCTGGAA
GTTATTCGCTCTGAAGATACCACTGGTCCTATCACTGGCCTGGCGCTCACCTCTGTCAACAAATTCCTGT
CCTATGCACTCATAGATCCAACTCATGAGGGCACAGCAGAGGGCATGGAGAACATGCAGATGCTGTCAC
TCATGCCCGTTTTGTGGGTACAGACCCTGCCAGCGATGAAGTTGTCCTGATGAAAATCCTCCAGGTTCTT
CGAACTCTGTTGCTAACCCCAGTGGGTACCCACTTAACAAATGAATCTGTGTGTGAGATTATGCAGTCTT
GCTTCCGGATTTGCTTTGAAATGAGGCTTAGTGAGTTATTGAGAAAATCCGCAGAGCACACTCTCGTAGA
CATGGTGCAGCTGCTCTTCACAAGGGTTACCCTCAGTTTAAAGAAGAACCCAAGAGCTATGTGGGAACCAAC
ATGAAGAAGCTGAAAATGAGAGCGGGAGGCATGAGCGACTCATCCAAGTGGAAAAAGCAGAAAAGATCCC
CTCGGCCCCCGCGTCACATGACCAGAGTCACACCACAGGTTCAGAGCTGCCCCGCCCCAAATGGAGCCACCTT
ATCCTGTAACCTCACCAGTGGCATGCCTTTCATTGATGTGCCCTCATCCATCTCCTCTGCAAGTTCAGAA
GCTGCCTCAGCAGTRGTCAGTCCCTGTACAGACAGTGGCCTGGAATTATCCTCCCAGACCACCTCCAAGG
AGGACCTCACTGACCTAGAGCAAGCTGGTTCCCCAAGGGAAAGCACAACCACAGAGTCTGGGAGCAATGA
GATAGGAGTTTCCGATCAGCTTGACCCTCAGGAAGGGTCCCATGTGGAAAAGGCCCAGTCAGCATCGGTG
GAATCTATCCCTGAAGTGTTGGAGGAGTGCACATCTCCTCCTGACCACTCTGCCTCTGTCCATGACATGG
ATTATGTCAATCCCCGGGGTGTTCGCTTCACACAGTCCTCCCAGAAGGAAGGCACAGCTTTGGTTCCTTA
TGGTCTTCCTTGCATCCGAGAGCTCTTCCGCTTCCTTATCTCCCTCACAAACCCACATGACCGCCACAAC
TCAGAGGGTATGATCCACATGGGACTGCATTTGCTGACAGTGGCTCTGGAGTCAGCCCCTGTAGCCCAGT
GCCAGACCCTCTTGGGTCTCATCAAGGATGAGATGTGTCGCCACTTATTCCAGCTACTCAGTGTAGAGCG
ATTGAACCTGTATGCTGCTTCCCTACGGGTATGCTTCTTACTCTTTGAGAGCATGGGGAGCACCTCAAGG
TTCCAATTAGAGGATGTACATGAAAAAACTCATGGAGGATCATCACTGTTGAAAACCCCAAGATGCCTTATG
AGATGAAGGAGATGGCACTGGAGGCCATCGTGCAGCTCTGGCGCATCCCCGCTTTGTCACTGAGCTCTA
TATCAACTACGATTGTGACTACTACTGCGCCAACCTCTTTGAAGACCTCACTAAGCTGCTGTCCAAGAAT
GCCTTTCCTGTGTCTGGTCAACTTTATACCACACACCTACTGTCCCTTGATGCCCCGTTGACGGTTATTG
ACAGCACTGAGGCTCACTGTCAAGCCAAAGTCCTCAACACTCTTACCCAGCAAGAGAAGAAGGAGACATC
CAGACCCAGCTACGAGGCAGTGGATAGCACCCAAGAAGCAAACAGTACTGAAAGAGCCCACCATTGATGGG
AAAGCCACAGGCATGGCCCTCAGATGCCCTAGGCCTTCATCTTCAAAGTGGAGGATGGCTGTCAGCAGAGC
ATGGGAAGCCAAGATGCAATGATGTGGAAGAAGCTGGTGACTCTGGGGCTGACAAAAAGTTTACCAGGAA
GCCGGCCTCGATTTTCCTGTCTTCTGCCAGATCCACGGGAACTAATTGAAATTAAGGACAAAAAGAAGCTG
CTGATCACTGGCACAGAGCAGTTCAATCAGAAACCCAAGAAGGGCATCCAGTTTCTACAGGAAAAAGGTC
TCCTTACCATCCCAATGGATAACACAGGAGGTGGCCCAGTGGCTCCGAGAGAACCCTCGGCTAGACAAGAA
AATGATTGGGGAGTTTGTGAGTGACCGAAAAAACATTGACCTGTTGGAGAGTTTTGTGAGCACCTTCAGC
TTTCAGGGTCTACGGCTTGATGAAGCTCTCCGACTCTACCTGGAAGCCTTCCGTTTGCCCGGGAAGGCAC
CAGTTATTCACAGGTTGCTGGAGGCATTCACAGAGCACTGGAGGAGTTGTAATGGCTCCCCATTTGCCAA

Fig. 24A

```
TAGCGATGCCTGCTTTGCCCTGGCCTATGCTGTCATCATGCTTAATACTGACCAGCATAACCACAATGTC
CGCAAACAGAATGTACCCATGACTCTGGAGGAGTTTCGAAAAAACCTAAAAGGTGTGAATGGAGGCAAGG
ACTTTGAGCAAGACATCCTGGAGGACATGTACCATGCCATCAAGAATGAGGAAATCGTGATGCCCGAGGA
ACAGACAGGCCTGGTTCGTGAGAACTATGTGTGGAGTGTGCTGCTGCACCGAGGTGCCACCCCTGAGGGT
ATATTCCTTCGTGTACCTCCTGGCAGCTATGATCTGACCTCTTCACTATGACCTGGGGCCCAACTATTG
CTGCTCTCTCTTATGTCTTTGATAAAAGCATTGAGGAGACCATCATCCAGAAAGCCATCTCAGGTTTCAG
GAAGTGTGCCATGATCTCTGCCCACTATGGCCTCAGCGATGTGTTTGACAATCTCATCATCTCTTTGTGC
AAGTTCACAGCTCTCAGTAGTGAGTCTATTGAGAACCTTCCCACTGTGTTTGGAAGCAACCCTAAAGCTC
ACATTGCAGCCAAGACAGTATTCCACTTGGCCCATCGTCATGGTGACATCCTTCGGGAGGGCTGGAAGAA
TATCATGGAGGCTGTGCTGCAACTCTTCCGTGCTCAACTTTTACCCCAGGCTATGGTGGAGGTAGAAGAT
TTTGTGGATCCCAATGGTAAGATCTCTCTACAGCGGGAGGAGATGCCATCAAACCGAGGAGAGTCATCGG
TACTTAGCTTTGTGAGCTGGCTGACGTTGAGTGGTCCTGAGCAGTCTAGTGTACGGGCCCCTCCACAGA
GAACCAGGAGCCAAGAGAGTGGCCCTTGGACTGTATCAAGCAATGTGACCCAGAAAAAATGATCACAGAA
AGCAAGTTCCTTCAGCTGGAATCATTGCAGGAGCTCATGAAGGCTTTGGTCTCAGTGACAGCAGATGAAG
AGACATACGATGAAGAGGATGCTGCTTTCTGTCTGGAGATGCTGCTGAGGATTGTGTTGGAGAACAGGGA
CCGTGTGGGCTGTGTATGGCAGACTGTTAGAGACCATCTATACCACTTATGTGTTCAGGCACAAGATTTC
TGCTTTCTCGTGGAGCGGGCAGTGGTGGGGCTGCTACGCCTCGCGATTCGGCTACTCCGGAGAGAAGAGA
TCAGTGGCCAGGTCCTGCTGTCCCTGGGCATCTTGTTACTGATGAAGCCCAGCGTGCTGTCCAGGGTCAG
CCACCAGGTTGCCTACGGGCTCCATGAACTCCTCAAGACCAATGCAGCCAACATCCACTCGGGTGACGAC
TGGGCCACCCTCTTCACATTGCTGGAGTGTATTGGCTCAGGCGTGAAGCCTCCAGATGCTCTACAGGCCA
CAGCCAGGGCTGATGCTCCTGATGCTGGAGCGCAGTCAGACAGTGAGCTCCCATCCTACCATCAAAATGA
TGTCAGCCTAGACCCGAGGGTACACTTCCGACTCAGAAGTCTACACTGACCATGGCAGGCCTGGCAAGATA
CACCGATCTGCCACAGATGCTGATATGGTCAACAGTGGTTGGTTAGTGGTGGGAAGGATGACATTGATA
ACTCCAAAGCAGGAGCAGGGCTCAGCAGGCCCAGCCCTTCACCCCTGGTTAATCAATATAGCCTCACAGT
GGGCCTGGACCTGGGACCACATGACACTAAGTCCCTGCTCAAGTGTGTGTGGAATCACTGTCCTTCATTGTT
CGTGATGCTGCTCACATCACCCCTGACAACTTTGAACTCTGTGTCAAGACTCTCCGCATCTTTGTAGAGG
CCAGTCTGAATGGTGGGGTGCAAATCCCAGGATAAACGTGGCAAGAGTCACAAATATGACAGCAAAGGGAA
CCGCTTCAAGAAAAAACCGAAGGAGGGCTCAGTGCTTCGGCGGCCCCGAACCTCCAGCCAGCATGGCACT
CGGGGTGGACATAGTGATGAGGAAGAGGATGAAGGAGTGCCTGCCAGCTACCATACGGTGTCTTTACAGG
TCAGTCAGGACTTGCTGGACCTGATGCACACCCTGCACACTCGGGCAGCCTCTATCTACAGCTCATGGGC
AGAGGAGCAGCCCACCTGGAGTCAGGTGGCCGAAAGATTGAAGCTGACTCACGCACCCTCTGGGCCCAC
TGCTGGTGCCCTTTATTGCAAGGCATCGCCTGCTTGTGCTGTGATGCCCGGCGCCAAGTGCGGATGCAGG
CCCTGACGTATCTGCAGCGAGCACTTCTGGTGCATGACCTACAAAAGCTAGATGCCCTGGAATGGGAGTC
CTGCTTTAACAAGGTGCTGTTTCCTCTACTGACCAAGCTGTTAGAAAATATCAGCCCTGCAGATGTGGGT
GGGATGGAGGAGACCCGGATGAGGGCTTCCACGCTGCTCTCAAAGGTCTTCCTGCAGCACCTGTCCCCTC
TGCTGTGCTGTCCACCTTTGCTGCCCTGTGGCTCACCATCCTGGACTTCATGGACAAGTACATGCATGC
AGGCTCCAGTGATTTGCTGTCAGAAGCAATCCCTGAGTCCCTGAAAAACATGCTCCTGGGTGATGGACACG
GCCGAGATCTTCCACAGTGCAGATGCGAGAGGAGGCAGCCCCTCTGCCCTCTGGGAGATCACCTGGGAGC
```

Fig. 24B

```
GCATTGATTGCTTTTTGCCACACTTACGTGACGAGCTCTTCAAGCAGACTGTCATCCAGGACCCCATGCC
CACGGAACCTCACAGCCAAAACGCTCTGGCCTCCACCCACCTGACCCCTGCTGCTGGTGACCCCGGCCAT
CTACCTTCCCCAGAGATACCCTCAGAAGTGGGGGCCTGTGACTCAGAGAAGCCTGAGGGTACCCGAGCCA
CCAGCAGCAGCTCTCCGGGATCACCAGTGGCCTCCGGCCCAGTAGACTGAGTCCTTCCCCAGAGGGACC
TCCCCGATTGGCCCAGCCCCCACTAATCCTGCAGCCCCTGACTTCCCCGCTGCAGGTGGGGTGCCACCC
ATGGCTCTGCCCATTATCCTCAACCCTGCACTCATCGAGGCCACCTCTCCGGTGCCTCTCTTGTCCACTC
CCCGTCCTACAGACCCTATTCCCACCTCTGAAGTCAAC
```

Fig. 24C

Peptide Sequence

MVDENIYIIQGEINIVVGAIKRNARNSTHIPLDEERDPLLHSPSHLKEVLNSVTELSEIEPNVPLRPFLE
VIRSEDTTGPITGLALTSVNKFLSYALIDPTHEGTAEGMENMADAVTHARFVGTDPASDBVVLMKILQVL
KTLLLTPVGTHLTNESVCEIMQSCFRICPEMRLSELLRKSAENTLVDMVQLLFTRLPQFKEEPKSYVGTN
MEKLEMRAGGMSDSSKNKKQKRSPRPPRHMTRVTPGSELPAPNGATLSCNLTSGMPFIDVPSSISSASSE
AASAVVSPCTDSGLELSSQTTSKEDLTDLEQAGSPKESTTTESGSREIGVSDQLDPQEGSHVEKAQSASV
ESIPEVLEECTSPFDHSASVHDMDYVNPKGVRFTQSSQKEGTALVPYGLPCIRELFKFLISLTNFHDRHN
SEGMINMGLHLLTVALESAPVAQCCQTLLGLIKDEMCRHLPQLLSVERLNLYAASLRVCFLLPESMREHLK
PQLEMYNKKLMEIITVENPKMPYEMKEMALEAIVQLWRIPSFVTELYINYDCDYYCANLFEDLTKLLSKN
AFPVSGQLYTTHLLGLDALLTVIDSTEAHCQAKVLNTLTQQEKKETSRPSYEAVDSTQEANSTERATIDG
KATGMASDALGLHLQSGGWLSAEHGKPRCKDVEEAGDSGADKKFTRKPPRFSCLLFDPRELIEIRNKKKL
LITGTEQFNQKFKKGIQFLQEKGLLTIFMENTEVAQWLRENFRLDKKMIGEFVSDRKNIELLESFVSTPS
FQGLELDEALRLYLEAFRLFGKAPVIHRLLEAFTEHNRSCKGSPFANSDACFALAYAVIMLNTDQHRHNV
RKQNVPMTLEEFRKNLRGVNGGKDPEQDILEDMYHAIKNEEIVMPEEQTSLVRENYVWSVLLSRGATPRG
IFLRVPPGSYDLDLFTMTWGPTIAALSYVFDKSIEETIIQKAISGFRKCAMISAHYGLSEVFDNLIISLC
KPTALSSESIENLPTVPGSNPKAHIAAKTVFHLAHRHGDILREGWKNIMEAVLQLPRAQLLPQAMVEVED
FVDPNGKISLQREEMPSNRGESSVLSPVSWLTLSGPEQSSVRGPSTERQEAKRVALECIKQCDPEKMITE
SKFLQLESLQELMKALVSVTADEETYDEEDAAFCLEMLLRIVLENRBRVGCVNQTVRDHLYHLCVQAQDF
CFLVERAVVGLLRLAIRLLRREEIGGQVLLSLRILLLMKPSVLSRVSHQVAYGLHELLKTNAANINSGDD
WATLPTLLECIGSGVEPPDALQATARADAPDAGAQSDSELPSYHQNDVSLDRGYTSDSEVYTDHGRPGKI
HRSATDADMVNSGWLVVGKDDIDNSKAGAGLSRPSPSPLVRQYSLTVGLDLGPHDTKSLLKCVESLSFIV
RDAAHITPDNFELCVKTLRIFVEASLNGGCKSQDKRGKSHKYDSKGNRFKKKFKEGSVLRRPRTSSQHGT
KGSHSDEEEDEGVPASYHTVSLQVSQDLLDLMHTLHTRAASIYSSWASEQHHLESGSRKIEADSRTLNAH
CWCPLLQGIACLCCDARRQVEMQALTYLQRALLVHDLQKLDALEWESCFNKVLFPLLTKLLENISPADVG
GNEETRMRASTLLSEVPLQHLSPLLSLSTPAALNLTILDPMEKYMHAGSSDLLSEAIPESLKNMLLVMDT
AEIFHSADARCGSPSALNEITNERIDCFLPHLEDELFKQTVIQDPMPTEPHSQHALASTHLTPAACDPGH
LPSPEIPSEVGACDSEKPEGTRATSSSSPGSPVASSPSRLSPSPEGPPPLAQPPLILQPLTSPLQVGVPP
MALPIILNPALIEATSPVPLLSTPRPTDPIPTSEVN

Fig. 25

SEQUENCE LISTING

```
<160> NUMBER OF SEQ ID NOS: 22

<210> SEQ ID NO 1
<211> LENGTH: 1861
<212> TYPE: PRT
<213> ORGANISM: Homo sapiens

<400> SEQUENCE: 1

Met Val Asp Lys Asn Ile Tyr Ile Ile Gln Gly Glu Ile Asn Ile Val
1               5                   10                  15

Val Gly Ala Ile Lys Arg Asn Ala Arg Trp Ser Thr His Thr Pro Leu
            20                  25                  30

Asp Glu Glu Arg Asp Pro Leu Leu His Ser Phe Gly His Leu Lys Glu
        35                  40                  45

Val Leu Asn Ser Ile Thr Glu Leu Ser Glu Ile Glu Pro Asn Val Phe
    50                  55                  60

Leu Arg Pro Phe Leu Glu Val Ile Arg Ser Glu Asp Thr Thr Gly Pro
65                  70                  75                  80
```

```
Ile Thr Gly Leu Ala Leu Thr Ser Val Asn Lys Phe Leu Ser Tyr Ala
                85                  90                  95

Leu Ile Asp Pro Thr His Glu Gly Thr Ala Glu Gly Met Glu Asn Met
            100                 105                 110

Ala Asp Ala Val Thr His Ala Arg Phe Val Gly Thr Asp Pro Ala Ser
            115                 120                 125

Asp Glu Val Val Leu Met Lys Ile Leu Gln Val Leu Arg Thr Leu Leu
            130                 135                 140

Leu Thr Pro Val Gly Ala His Leu Thr Asn Glu Ser Val Cys Glu Ile
145                 150                 155                 160

Met Gln Ser Cys Phe Arg Ile Cys Phe Glu Met Arg Leu Ser Glu Leu
                165                 170                 175

Leu Arg Lys Ser Ala Glu His Thr Leu Val Asp Met Val Gln Leu Leu
            180                 185                 190

Phe Thr Arg Leu Pro Gln Phe Lys Glu Glu Pro Lys Asn Tyr Val Gly
            195                 200                 205

Thr Asn Met Lys Lys Leu Lys Met Arg Ala Gly Gly Met Ser Asp Ser
    210                 215                 220

Ser Lys Trp Lys Lys Gln Lys Arg Ser Pro Arg Pro Arg His Met
225                 230                 235                 240

Thr Lys Val Thr Pro Gly Ser Glu Leu Pro Thr Pro Asn Gly Thr Thr
            245                 250                 255

Leu Ser Ser Asn Leu Thr Gly Gly Met Pro Phe Ile Asp Val Pro Thr
            260                 265                 270

Pro Ile Ser Ser Ala Ser Ser Glu Ala Ala Ser Ala Val Val Ser Pro
            275                 280                 285

Ser Thr Asp Ser Gly Leu Glu Phe Ser Ser Gln Thr Thr Ser Lys Glu
    290                 295                 300

Asp Leu Thr Asp Leu Glu Gln Pro Gly Ser Pro Gly Tyr Ser Thr Ala
305                 310                 315                 320

Thr Glu Pro Gly Ser Ser Glu Leu Gly Val Pro Glu Gln Pro Asp Leu
            325                 330                 335

Gln Glu Gly Thr His Val Glu Lys Ser Gln Ser Ala Ser Val Glu Ser
            340                 345                 350

Ile Pro Glu Val Leu Glu Glu Cys Thr Ser Pro Ala Asp His Ser Asp
            355                 360                 365

Ser Ala Ser Val His Asp Met Asp Tyr Val Asn Pro Arg Gly Val Arg
    370                 375                 380

Phe Thr Gln Ser Ser Gln Lys Glu Gly Thr Ala Leu Val Pro Tyr Gly
385                 390                 395                 400

Leu Pro Cys Ile Arg Glu Leu Phe Arg Phe Leu Ile Ser Leu Thr Asn
            405                 410                 415

Pro His Asp Arg His Asn Ser Glu Val Met Ile His Met Gly Leu His
            420                 425                 430

Leu Leu Thr Val Ala Leu Glu Ser Ala Pro Val Ala Gln Cys Gln Thr
            435                 440                 445

Leu Leu Gly Leu Ile Lys Asp Glu Met Cys Arg His Leu Phe Gln Leu
    450                 455                 460

Leu Ser Ile Glu Arg Leu Asn Leu Tyr Ala Ala Ser Leu Arg Val Cys
465                 470                 475                 480

Phe Leu Leu Phe Glu Ser Met Arg Glu His Leu Lys Phe Gln Met Glu
            485                 490                 495

Met Tyr Ile Lys Lys Leu Met Glu Ile Ile Thr Val Glu Asn Pro Lys
            500                 505                 510
```

-continued

```
Met Pro Tyr Glu Met Lys Glu Met Ala Leu Glu Ala Ile Val Gln Leu
            515                 520                 525

Trp Arg Ile Pro Ser Phe Val Thr Glu Leu Tyr Ile Asn Tyr Asp Cys
            530                 535                 540

Asp Tyr Tyr Cys Ser Asn Leu Phe Glu Glu Leu Thr Lys Leu Leu Ser
545                 550                 555                 560

Lys Asn Ala Phe Pro Val Ser Gly Gln Leu Tyr Thr Thr His Leu Leu
            565                 570                 575

Ser Leu Asp Ala Leu Leu Thr Val Ile Asp Ser Thr Glu Ala His Cys
            580                 585                 590

Gln Ala Lys Val Leu Asn Ser Leu Thr Gln Gln Lys Lys Glu Thr
            595                 600                 605

Ala Arg Pro Ser Cys Glu Ile Val Asp Gly Thr Arg Glu Ala Ser Asn
            610                 615                 620

Thr Glu Arg Thr Ala Ser Asp Gly Lys Ala Val Gly Met Ala Ser Asp
625                 630                 635                 640

Ile Pro Gly Leu His Leu Pro Gly Gly Arg Leu Pro Glu His
            645                 650                 655

Gly Lys Ser Gly Cys Ser Asp Leu Glu Ala Val Asp Ser Gly Ala
            660                 665                 670

Asp Lys Lys Phe Ala Arg Lys Pro Arg Phe Ser Cys Leu Leu Pro
            675                 680                 685

Asp Pro Arg Glu Leu Ile Glu Ile Lys Asn Lys Lys Leu Leu Ile
            690                 695                 700

Thr Gly Thr Glu Gln Phe Asn Gln Lys Pro Lys Lys Gly Ile Gln Phe
705                 710                 715                 720

Leu Gln Glu Lys Gly Leu Leu Thr Ile Pro Met Asp Asn Thr Glu Val
            725                 730                 735

Ala Gln Trp Leu Arg Glu Asn Pro Arg Leu Asp Lys Lys Met Ile Gly
            740                 745                 750

Glu Phe Val Ser Asp Arg Lys Asn Ile Asp Leu Leu Glu Ser Phe Val
            755                 760                 765

Ser Thr Phe Ser Phe Gln Gly Leu Arg Leu Asp Glu Ala Leu Arg Leu
            770                 775                 780

Tyr Leu Glu Ala Phe Arg Leu Pro Gly Glu Ala Pro Val Ile Gln Arg
785                 790                 795                 800

Leu Leu Glu Ala Phe Thr Glu Arg Trp Met Asn Cys Asn Gly Ser Pro
            805                 810                 815

Phe Ala Asn Ser Asp Ala Cys Phe Ser Leu Ala Tyr Ala Val Ile Met
            820                 825                 830

Leu Asn Thr Asp Gln His Asn His Asn Val Arg Lys Gln Asn Ala Pro
            835                 840                 845

Met Thr Leu Glu Glu Phe Arg Lys Asn Leu Lys Gly Val Asn Gly Gly
            850                 855                 860

Lys Asp Phe Glu Gln Asp Ile Leu Glu Asp Met Tyr His Ala Ile Lys
865                 870                 875                 880

Asn Glu Glu Ile Val Met Pro Glu Glu Gln Thr Gly Leu Val Arg Glu
            885                 890                 895

Asn Tyr Val Trp Asn Val Leu Leu His Arg Gly Ala Thr Pro Glu Gly
            900                 905                 910

Ile Phe Leu Arg Val Pro Thr Ala Ser Tyr Asp Leu Asp Leu Phe Thr
            915                 920                 925

Met Thr Trp Gly Pro Thr Ile Ala Ala Leu Ser Tyr Val Phe Asp Lys
```

```
            930             935             940
Ser Leu Glu Glu Thr Ile Ile Gln Lys Ala Ile Ser Gly Phe Arg Lys
945                 950                 955                 960

Cys Ala Met Ile Ser Ala His Tyr Gly Leu Ser Asp Val Phe Asp Asn
            965             970             975

Leu Ile Ile Ser Leu Cys Lys Phe Thr Ala Leu Ser Ser Glu Ser Ile
            980             985             990

Glu Asn Leu Pro Ser Val Phe Gly Ser Asn Pro Lys Ala His Ile Ala
        995                 1000            1005

Ala Lys Thr Val Phe His Leu Ala His Arg His Gly Asp Ile Leu
    1010            1015            1020

Arg Glu Gly Trp Lys Asn Ile Met Glu Ala Met Leu Gln Leu Phe
    1025            1030            1035

Arg Ala Gln Leu Leu Pro Lys Ala Met Ile Glu Val Glu Asp Phe
    1040            1045            1050

Val Asp Pro Asn Gly Lys Ile Ser Leu Gln Arg Glu Glu Thr Pro
    1055            1060            1065

Ser Asn Arg Gly Glu Ser Thr Val Leu Ser Phe Val Ser Trp Leu
    1070            1075            1080

Thr Leu Ser Gly Pro Glu Gln Ser Ser Val Arg Gly Pro Ser Thr
    1085            1090            1095

Glu Asn Gln Glu Ala Lys Arg Val Ala Leu Glu Cys Ile Lys Gln
    1100            1105            1110

Cys Asp Pro Glu Lys Met Ile Thr Glu Ser Lys Phe Leu Gln Leu
    1115            1120            1125

Glu Ser Leu Gln Glu Leu Met Lys Ala Leu Val Ser Val Thr Pro
    1130            1135            1140

Asp Glu Glu Thr Tyr Asp Glu Glu Asp Ala Ala Phe Cys Leu Glu
    1145            1150            1155

Met Leu Leu Arg Ile Val Leu Glu Asn Arg Asp Arg Val Gly Cys
    1160            1165            1170

Val Trp Gln Thr Val Arg Asp His Leu Tyr His Leu Cys Val Gln
    1175            1180            1185

Ala Gln Asp Phe Cys Phe Leu Val Glu Arg Ala Val Val Gly Leu
    1190            1195            1200

Leu Arg Leu Ala Ile Arg Leu Leu Arg Arg Glu Glu Ile Ser Ala
    1205            1210            1215

Gln Val Leu Leu Ser Leu Arg Ile Leu Leu Leu Met Lys Pro Ser
    1220            1225            1230

Val Leu Ser Arg Val Ser His Gln Val Ala Tyr Gly Leu His Glu
    1235            1240            1245

Leu Leu Lys Thr Asn Ala Ala Asn Ile His Ser Gly Asp Asp Trp
    1250            1255            1260

Ala Thr Leu Phe Thr Leu Leu Glu Cys Ile Gly Ser Gly Val Lys
    1265            1270            1275

Pro Pro Ala Ala Leu Gln Ala Thr Ala Arg Ala Asp Ala Pro Asp
    1280            1285            1290

Ala Gly Ala Gln Ser Asp Ser Glu Leu Pro Ser Tyr His Gln Asn
    1295            1300            1305

Asp Val Ser Leu Asp Arg Gly Tyr Thr Ser Asp Ser Glu Val Tyr
    1310            1315            1320

Thr Asp His Gly Arg Pro Gly Lys Ile His Arg Ser Ala Thr Asp
    1325            1330            1335
```

-continued

```
Ala Asp Val Val Asn Ser Gly Trp Leu Val Val Gly Lys Asp Asp
1340                1345                1350

Val Asp Asn Ser Lys Pro Gly Pro Ser Arg Pro Gly Pro Ser Pro
1355                1360                1365

Leu Ile Asn Gln Tyr Ser Leu Thr Val Gly Leu Asp Leu Gly Pro
1370                1375                1380

His Asp Thr Lys Ser Leu Leu Lys Cys Val Glu Ser Leu Ser Phe
1385                1390                1395

Ile Val Arg Asp Ala Ala His Ile Thr Pro Asp Asn Phe Glu Leu
1400                1405                1410

Cys Val Lys Thr Leu Arg Ile Phe Val Glu Ala Ser Leu Asn Gly
1415                1420                1425

Gly Cys Lys Ser Gln Glu Lys Arg Gly Lys Ser His Lys Tyr Asp
1430                1435                1440

Ser Lys Gly Asn Arg Phe Lys Lys Ser Lys Glu Gly Ser Met
1445                1450                1455

Leu Arg Arg Pro Arg Thr Ser Ser Gln His Ala Ser Arg Gly Gly
1460                1465                1470

Gln Ser Asp Asp Asp Glu Asp Glu Gly Val Pro Ala Ser Tyr His
1475                1480                1485

Thr Val Ser Leu Gln Val Ser Gln Asp Leu Leu Asp Leu Met His
1490                1495                1500

Thr Leu His Thr Arg Ala Ala Ser Ile Tyr Ser Ser Trp Ala Glu
1505                1510                1515

Glu Gln Arg His Leu Glu Thr Gly Gly Gln Lys Ile Glu Ala Asp
1520                1525                1530

Ser Arg Thr Leu Trp Ala His Cys Trp Cys Pro Leu Leu Gln Gly
1535                1540                1545

Ile Ala Cys Leu Cys Cys Asp Ala Arg Arg Gln Val Arg Met Gln
1550                1555                1560

Ala Leu Thr Tyr Leu Gln Arg Ala Leu Leu Val His Asp Leu Gln
1565                1570                1575

Lys Leu Asp Ala Leu Glu Trp Glu Ser Cys Phe Asn Lys Val Leu
1580                1585                1590

Phe Pro Leu Leu Thr Lys Leu Leu Glu Asn Ile Ser Pro Ala Asp
1595                1600                1605

Val Gly Gly Met Glu Glu Thr Arg Met Arg Ala Ser Thr Leu Leu
1610                1615                1620

Ser Lys Val Phe Leu Gln His Leu Ser Pro Leu Leu Ser Leu Ser
1625                1630                1635

Thr Phe Ala Ala Leu Trp Leu Thr Ile Leu Asp Phe Met Asp Lys
1640                1645                1650

Tyr Met His Ala Gly Ser Ser Asp Leu Leu Ser Glu Ala Ile Pro
1655                1660                1665

Glu Ser Leu Lys Asn Met Leu Leu Val Met Asp Thr Ala Glu Ile
1670                1675                1680

Phe His Ser Ala Asp Ala Arg Gly Gly Gly Pro Ser Ala Leu Trp
1685                1690                1695

Glu Ile Thr Trp Glu Arg Ile Asp Cys Phe Leu Pro His Leu Arg
1700                1705                1710

Asp Glu Leu Phe Lys Gln Thr Val Ile Gln Asp Pro Met Pro Met
1715                1720                1725

Glu Pro Gln Gly Gln Lys Pro Leu Ala Ser Ala His Leu Thr Ser
1730                1735                1740
```

```
Ala Ala Gly Asp Thr Arg Thr Pro Gly His Pro Pro Pro Glu
    1745             1750                 1755

Ile Pro Ser Glu Leu Gly Ala Cys Asp Phe Glu Lys Pro Glu Ser
    1760                 1765             1770

Pro Arg Ala Ala Ser Ser Ser Ser Pro Gly Ser Pro Val Ala Ser
    1775                 1780                 1785

Ser Pro Ser Arg Leu Ser Pro Thr Pro Asp Gly Pro Pro Pro Leu
    1790                 1795                 1800

Ala Gln Pro Pro Leu Ile Leu Gln Pro Leu Ala Ser Pro Leu Gln
    1805                 1810                 1815

Val Gly Val Pro Pro Met Thr Leu Pro Ile Ile Leu Asn Pro Ala
    1820                 1825                 1830

Leu Ile Glu Ala Thr Ser Pro Val Pro Leu Leu Ala Thr Pro Arg
    1835                 1840                 1845

Pro Thr Asp Pro Ile Pro Thr Ser Glu Val Asn Ala Ala
    1850                 1855                 1860

<210> SEQ ID NO 2
<211> LENGTH: 6376
<212> TYPE: DNA
<213> ORGANISM: Homo sapiens

<400> SEQUENCE: 2
gacagggaag gtacccggct ctactgcccg tcccggacga ctcatcctgg cggactgtgc      60
agtcccaccc tgacttcagc ctcaatttcc aggaaacagg ctccttctct tctcccatct    120
gctaccagag ccgggagagc tgctcggaga cgcctccggg gtgcgggctg acatgagca     180
gcggctgccg gtcctgggac taggccccgc cattttggat ccgctgacag gtttgccaag    240
atggtggata gaatatttta catcattcaa ggggagatta acattgtggt tggggccatc    300
aaacgaaatg cccgatggag cacccataca ccactggatg aagaacggga tcctctgctg    360
catagtttcg gtcatctaaa ggaggtttta acagtataa cagaactctc agaaattgag     420
cccaatgtat tccttcgacc tttctggaa gtgattcgct ctgaagatac cactggccct     480
atcactggac tggcactcac ctctgtcaac aagttcctgt cctatgcact catagatccc    540
acccatgagg gcacagcaga gggcatggag aacatggcag atgctgtcac ccatgctcgt    600
tttgtgggca cggatcctgc cagtgatgaa gttgtcctga tgaaaatcct tcaggttcta    660
cggactctgc tgctaacccc agtgggtgcc cacctaacca atgaatctgt gtgtgagatt    720
atgcagtctt gcttccggat ctgctttgaa atgaggctca gtgagttatt gagaaaatcc    780
gcagagcaca ctctcgtaga catggtgcag ctgctcttca aaggttacc tcagtttaaa     840
gaagaaccca gaactatgt ggggaccaac atgaagaagc tgaaaatgag agccggaggc    900
atgagtgatt catccaaatg gaagaaacag aagagatccc ctcggccccc acgccatatg    960
accaaagtca caccaggttc agagctgccc actcccaatg gaaccacctt atcatctaac   1020
ctcactggtg gcatgccctt cattgatgtg cccactccca tctcctctgc aagttcagaa   1080
gctgcctcag cagtggtcag tccctctaca gacagtggcc tggaattctc ctcccaaacc   1140
acttccaagg aagaccttac tgatctagag caacctggct ctccagggta cagcacagct   1200
acagagcctg gaagcagtga gctaggtgtt cccgagcagc tgacctcca ggaagggacc    1260
catgtggaaa agtcccagtc agcatctgtg gagtccatcc ctgaagtgtt agaggagtgc   1320
acgtccctg ccgaccactc tgactctgcc tctgtccatg acatggatta cgtcaatccc    1380
cgggcgtgc gctttacaca gtcctcccag aaagaaggca cagctttggt ccctatggt    1440
```

```
cttccctgca tccgcgagct cttccgcttc ctcatctccc tcaccaatcc acacgaccgc   1500
cataactcag aggttatgat tcacatggga ctgcatttgc tgacagtggc ccttgagtca   1560
gcccctgtag cccagtgcca gaccctcttg ggcctcatca aggatgagat gtgccgtcac   1620
ttattccagc tactcagcat agagcgacta aacctttatg ctgcttccct gcgagtatgc   1680
ttcctactgt ttgagagcat gcgagagcac ctcaagttcc aaatggagat gtacatcaaa   1740
aagcttatgg agatcatcac tgtggagaac cccaagatgc cttatgagat gaaggagatg   1800
gcactggagg ccattgtgca gctctggcgc atccccagct tgtcacaga gctctacatc    1860 aactatgatt gtgactacta ctgttccaac ctctttgagg aactcacaaa gctgctgtcc   1920
aagaatgcct tccctgtgtc tggtcaactc tatacaacac acctactatc tcttgatgcc   1980
ctattgacag tgattgacag caccgaggcc cactgccagg ctaaagtcct caacagcctc   2040
acccagcaag agaagaagga cacagccaga ccaagctgtg agatagtaga tggcacccga   2100
gaagctagca atactgagag aactgccagc gatgggaaag ctgtaggcat ggcctcagac   2160
atcccaggcc tgcatctgcc aggtggaggg cggctgccac cagaacatgg gaaatcagga   2220
tgcagtgatc tggaggaagc tgttgactct ggggctgaca aaaagtttgc ccggaagcca   2280
ccccgatttt cctgtctcct gccagatcca cgggaactaa ttgaaattaa aaacaaaaag   2340
aagctgctaa tcactggcac agagcagttc aatcagaaac caagaagggg gattcagttt   2400
ctgcaagaga aaggcctcct caccatccca atggacaaca cagaggttgc tcagtggctc   2460
cgagagaacc ctcggctgga caagaagatg attggagagt tgtgagtga ccgcaaaaac    2520 attgacctgt tggagagctt tgtgagcacc ttcagttttc agggtctgcg actggacgaa   2580
gccctccgcc tctacctgga agccttccgt ttgcctgggg aagcaccagt catccagagg   2640
ttgctggagg cattcacaga gcgttggatg aattgtaatg gctcccccatt tgccaatagc   2700 gatgcctgct tttccctggc ctatgctgtc atcatgctta atactgacca gcacaaccac   2760
aatgttcgta acagaatgc acccatgacc ctggaggagt ttcgcaaaaa tctgaaggt     2820 gtgaatggag gcaaggactt tgagcaagac atcctggagg acatgtacca tgccatcaag   2880
aatgaggaaa ttgtaatgcc tgaggagcag acaggcttgg ttcgggagaa ctatgtgtgg   2940
aatgtgctgc ttcatcgagg tgccacccct gagggcatat tcctgcgtgt gcctactgcc   3000
agctatgatc ttgacctctt caccatgacc tggggcccca ctattgctgc tctctcttat   3060
gtctttgaca aaagccttga ggagacaatc atccagaaag ccatctcagg cttcaggaag   3120
tgcgccatga tctccgccca ctatggcctc agcgatgtgt ttgacaatct catcatctct   3180
ctatgcaaat tcacagctct cagcagtgag tctattgaga acctgcccag tgtatttgga   3240
agcaacccta aagcccatat tgcagccaag acagtattcc atttggccca tcgtcatggt   3300
gacatcctgc gggagggctg gaagaatatc atggaggcca tgctgcagct cttccgagcc   3360
caactactgc ccaaggctat gatagaggta gaagatttcg tggatcccaa tggcaagatc   3420
tctctacagc gggaagagac accatcaaac cgaggagagt caacagtgct gagctttgtg   3480
agctggctaa cactgagtgg tcctgagcag tctagtgttc ggggcccatc cactgaaaac   3540
caagaggcca agagagtggc cttagagtgt ataaagcaat gtgacccaga aaaatgatc    3600 acagaaagca agttcctcca gctggagtca ctacaggagc tcatgaaggc tctggtctca   3660
gtgacaccag atgaagagac atatgatgag gaagatgctg ctttctgcct agagatgctg   3720
ctaaggattg tgttggagaa cagggatcgt gtgggctgtg tgtggcagac tgttcgagac   3780
catctatacc acctctgtgt tcaggcacaa gatttctgct tccttgtgga gcgggcagtg   3840
```

```
gtggggttgc tacgcctggc cattcggctt ctccggagag aagagatcag tgctcaggtg   3900
ctgctctccc tgcgcatttt gctactgatg aagcccagtg tgctatcccg agtcagccac   3960
caggttgcgt atgggctcca tgaactcctg aagaccaatg cagccaacat ccactcaggt   4020
gatgactggg ccacactctt cacactgctg gagtgcatcg gctcaggtgt gaagcctcca   4080
gctgctctgc aggccacagc cagggcagat gcacctgatg ccggggccca gtcagatagt   4140
gagctcccat cctaccatca gaatgacgtg agcctggatc gagggtacac ttccgactca   4200
gaggtctaca ctgaccatgg caggccgggc aagatacacc gatcagccac agatgccgat   4260
gtggtcaaca gtggttggtt agtggttggg aaggatgacg ttgataactc caagccaggg   4320
cccagccgcc caggcccttc acccctgatc aatcaataca gcctaacagt gggactggat   4380
ttggggccac acgacactaa gtctctgctt aagtgtgtgg aatcgctgtc cttcatcgtg   4440
cgtgatgctg cccacatcac acctgacaac tttgagctct gcgtcaagac tctccggatc   4500
tttgtggagg ccagtctgaa tggcggatgc aagtcccagg agaaacgtgg caagagtcac   4560
aaatatgaca gcaagggaa ccgcttcaag aagaaatcca agagggatc aatgcttcgc   4620 cggcctcgaa cctccagcca acatgcctct cggggcgggc agagtgatga tgatgaggac   4680
gaaggcgtgc ctgccagcta ccatacggtg tctttacagg tcagtcagga cttgctagac   4740
ctgatgcaca ccctgcacac gcgggcagcc tctatctaca gctcatgggc ggaggagcaa   4800
cgccacctgg agacaggtgg ccagaagatt gaagctgatt ctcgcaccct ctgggcccac   4860
tgctggtgcc ctttactgca gggtattgcc tgcctgtgct gcgatgcccg cgcgcaggta   4920
cggatgcagg cactgaccta tctgcagcga gcactacttg tacatgatct gcaaaagcta   4980
gatgccctgg aatgggagtc ctgttttaac aaggtgctgt ttcctctact taccaagctc   5040
ttggagaaca tcagccctgc agatgtgggt gggatggagg agacccggat gagggcttcc   5100
acattgctct ctaaggtctt cctgcagcac ctgtctccac tgctgtcact ctctacctt    5160 gcggccctct ggctcaccat cttggacttc atggacaagt acatgcacgc aggctccagc   5220
gacttactgt cagaggcgat ccctgagtct ctgaagaaca tgcttctggt gatggacaca   5280
gcggagattt ccacagtgc agatgcacgg ggaggcggcc cctcggccct ctgggagatc   5340
acctgggaac gcattgactg ttttctccct cacctacgag atgaactctt caagcagacc   5400
gtcatccagg accccatgcc catggagcct caaggccaaa agcctctcgc ctcagcccac   5460
ctgacttccg ctgctggcga cactaggaca cctggccatc caccgccccc agagattcca   5520
tctgagctgg gggcctgtga ctttgagaag cccgagagcc cccgagccgc cagcagcagc   5580
tccccaggat caccagtggc ctcaagcccc agcaggctga gccccacccc cgacgggcct   5640
ccacccttgg ctcagccccc actgatcctg cagcccttgg cctccccact gcaggtgggc   5700
gtgccaccta tgactctgcc catcatcctc aaccctgcgc tcatcgaggc cacctcacca   5760 gtgccccctcc tggccacacc ccgccccaca gatcccatac ccacctctga ggtcaactaa   5820
ggcaggtcac tcagagatca ggaccagtgc ttcccaccag gctttccttg accccacttc   5880
tggctgtcct gcgggccaca agctcttcag gccaagtcag agctgctgtt gctgccactt   5940
ggatggggac ctgaaaaaga gaatgttgat agccccagct aagaccccca atcagctgtg   6000 ggacctttt cctcctctgc gctccattcc tgggggttca gcctgagagt gaactcagct   6060
gtcatctgca gcctctgcct ccagcccggc agctctgggg aggcatccgt gtgccggccc   6120
tgcagtgcct gcccacggtc aggcattgaa aactaagccc aaccactctg cactttgttt   6180
cccactccca ttagccctgg gccacctcct ccagttcttc ctcttttact aattagttgg   6240
```

```
tcagtttgga gagttgactg gcaccatgga gggtaggcag gtgggggctg ggtgggggac    6300
tgcccacagg agcatgtaca tatggaaaaa cagaacaaca gtggactttt tatgatataa    6360
taaatgtctt agtacc                                                   6376

<210> SEQ ID NO 3
<211> LENGTH: 77
<212> TYPE: DNA
<213> ORGANISM: Homo sapiens

<400> SEQUENCE: 3
gccgcgctag cctgaggcat agtcaggcac gtcataagga tagccgttga cttcagaggt    60
gggaataggg tctgtag                                                  77

<210> SEQ ID NO 4
<211> LENGTH: 39
<212> TYPE: DNA
<213> ORGANISM: Homo sapiens

<400> SEQUENCE: 4
gacaggtttg ccaagatggt ggataagaat atttacatc                          39

<210> SEQ ID NO 5
<211> LENGTH: 43
<212> TYPE: DNA
<213> ORGANISM: Homo sapiens

<400> SEQUENCE: 5
gccttccgtt tgcccgggaa ggcaccagtt attcacaggt tgc                     43

<210> SEQ ID NO 6
<211> LENGTH: 43
<212> TYPE: DNA
<213> ORGANISM: Homo sapiens

<400> SEQUENCE: 6
gcaacctgtg aataactggt gccttcccgg gcaaacggaa ggc                     43

<210> SEQ ID NO 7
<211> LENGTH: 35
<212> TYPE: DNA
<213> ORGANISM: Homo sapiens

<400> SEQUENCE: 7
ggcctatgct gtcatcttgc ttaatactga ccagc                              35

<210> SEQ ID NO 8
<211> LENGTH: 35
<212> TYPE: DNA
<213> ORGANISM: Homo sapiens

<400> SEQUENCE: 8
gctggtcagt attaagcaag atgacagcat aggcc                              35

<210> SEQ ID NO 9
<211> LENGTH: 5571
<212> TYPE: DNA
<213> ORGANISM: Cricetulus griseus

<400> SEQUENCE: 9
atggtggata agaatattta catcattcaa ggagaaatta acattgttgt tggcgccatc    60
aaacgaaatg cacgatggag cacccatata ccactggatg aagaacggga tcctctgctg    120
```

```
cacagtttca gtcatctaaa ggaggtctta aacagtgtaa cagaactctc agagattgag    180
ccaaatgtat tccttcgtcc atttctggaa gttattcgct ctgaagatac cactggtcct    240
atcactggcc tggcgctcac ctctgtcaac aaattcctgt cctatgcact catagatcca    300
actcatgagg gcacagcaga gggcatggag aacatggcag atgctgtcac tcatgcccgt    360
tttgtgggta cagaccctgc cagcgatgaa gttgtcctga tgaaaatcct ccaggttctt    420
cgaactctgt tgctaacccc agtgggtacc cacttaacaa atgaatctgt gtgtgagatt    480
atgcagtctt gcttccggat ttgctttgaa atgaggctta gtgagttatt gagaaaatcc    540
gcagagcaca ctctcgtaga catggtgcag ctgctcttca caaggttacc tcagtttaaa    600
gaagaaccca gagctatgt gggaaccaac atgaagaagc tgaaaatgag agcgggaggc    660
atgagcgact catccaagtg gaaaaagcag aaaagatccc ctcggccccc gcgtcacatg    720
accagagtca caccaggttc agagctgccc gccccaaatg gagccacctt atcctgtaac    780
ctcaccagtg gcatgccttt cattgatgtg ccctcatcca tctcctctgc aagttcagaa    840
gctgcctcag cagtggtcag tccctgtaca gacagtggcc tggaattatc ctcccagacc    900
acctccaagg aggacctcac tgacctagag caagctggtt ccccaaggga aagcacaacc    960
acagagtctg ggagcaatga gataggagtt ccgatcagc ttgaccctca ggaagggtcc   1020
catgtggaaa aggcccagtc agcatcggtg gaatctatcc ctgaagtgtt ggaggagtgc   1080
acatctcctc ctgaccactc tgcctctgtc catgacatgg attatgtcaa tccccggggt   1140
gttcgcttca cacagtcctc ccagaaggaa ggcacagctt tggttcctta tggtcttcct   1200
tgcatccgag agctcttccg cttccttatc tccctcacaa acccacatga ccgccacaac   1260
tcagagggta tgatccacat gggactgcat ttgctgacag tggctctgga gtcagcccct   1320
gtagcccagt gccagaccct cttgggtctc atcaaggatg agatgtgtcg ccacttattc   1380
cagctactca gtgtagagcg attgaactg tatgctgctt ccctacgggt atgcttctta   1440 ctcttttgaga gcatgcggga gcacctcaag ttccaattag agatgtacat gaaaaaactc   1500
atggagatca tcactgttga aaaccccaag atgccttatg agatgaagga gatggcactg   1560
gaggccatcg tgcagctctg gcgcatcccc agctttgtca ctgagctcta tatcaactac   1620
gattgtgact actactgcgc caacctcttt gaagacctca ctaagctgct gtccaagaat   1680
gcctttcctg tgtctggtca actttatacc acacacctac tgtcccttga tgccctgttg   1740
acggttattg acagcactga ggctcactgt caagccaaag tcctcaacac tcttacccag   1800
caagagaaga aggagacatc cagacccagc tacgaggcag tggatagcac ccaagaagca   1860
aacagtactg aaagagccac cattgatggg aaagccacag gcatggcctc agatgcccta   1920
ggccttcatc ttcaaagtgg aggatggctg tcagcagagc atgggaagcc aagatgcaat   1980
gatgtggaag aagctggtga ctctgggggct gacaaaaagt ttaccaggaa gccgcctcga   2040
ttttcctgtc ttctgccaga tccacgggaa ctaattgaaa ttaagaacaa aaagaagctg   2100
ctgatcactg gcacagagca gttcaatcag aaacccaaga agggcatcca gtttctacag   2160
gaaaaaggtc tccttaccat cccaatggat aacacagagg tggcccagtg gctccgagag   2220
aaccctcggc tagacaagaa aatgattggg gagtttgtga gtgaccgaaa aacattgac    2280 ctgttggaga gttttgtgag caccttcagc tttcagggtc tacggcttga tgaagctctc   2340
cgactctacc tggaagcctt ccgtttgccc ggggaagcac cagttattca caggttgctg   2400
gaggcattca cagagcactg gaggagttgt aatggctccc catttgccaa tagcgatgcc   2460
tgctttgccc tggcctatgc tgtcatcatg cttaatactg accagcataa ccacaatgtc   2520
```

```
cgcaaacaga atgtacccat gactctggag gagtttcgaa aaaacctaaa aggtgtgaat    2580
ggaggcaagg actttgagca agacatcctg gaggacatgt accatgccat caagaatgag    2640
gaaatcgtga tgcccgagga acagacaggc ctggttcgtg agaactatgt gtggagtgtg    2700
ctgctgcacc gaggtgccac ccctgagggt atattccttc gtgtacctcc tggcagctat    2760
gatcttgacc tcttcactat gacctggggc ccaactattg ctgctctctc ttatgtcttt    2820
gataaaagca ttgaggagac catcatccag aaagccatct caggtttcag gaagtgtgcc    2880
atgatctctg cccactatgg cctcagcgat gtgtttgaca atctcatcat ctctttgtgc    2940
aagttcacag ctctcagtag tgagtctatt gagaaccttc ccactgtgtt tggaagcaac    3000
cctaaagctc acattgcagc caagacagta ttccacttgg cccatcgtca tggtgacatc    3060
cttcgggagg gctggaagaa tatcatggag gctgtgctgc aactcttccg tgctcaactt    3120 ttacccagg ctatggtgga ggtagaagat tttgtggatc ccaatggtaa gatctctcta    3180
cagcgggagg agatgccatc aaaccgagga gagtcatcgg tacttagctt tgtgagctgg    3240
ctgacgttga gtggtcctga gcagtctagt gtacggggcc cctccacaga gaaccaggag    3300
gccaagagag tggccttgga ctgtatcaag caatgtgacc cagaaaaaat gatcacagaa    3360
agcaagttcc ttcagctgga atcattgcag gagctcatga aggctttggt ctcagtgaca    3420
gcagatgaag agacatacga tgaagaggat gctgctttct gtctggagat gctgctgagg    3480
attgtgttgg agaacaggga ccgtgtgggc tgtgtatggc agactgttag agaccatcta    3540
taccacttat gtgttcaggc acaagatttc tgctttctcg tggagcgggc agtggtgggg    3600
ctgctacgcc tcgcgattcg gctactccgg agagaagaga tcagtggcca ggtcctgctg    3660
tccctgcgca tcttgttact gatgaagccc agcgtgctgt ccagggtcag ccaccaggtt    3720
gcctacgggc tccatgaact cctcaagacc aatgcagcca acatccactc gggtgacgac    3780
tgggccaccc tcttcacatt gctggagtgt attggctcag gcgtgaagcc tccagatgct    3840
ctacaggcca cagccagggc tgatgctcct gatgctggag cgcagtcaga cagtgagctc    3900
ccatcctacc atcaaaatga tgtcagccta gaccgagggt acacttccga ctcagaagtc    3960
tacactgacc atggcaggcc tggcaagata caccgatctg ccacagatgc tgatatggtc    4020
aacagtggtt ggttagtggt ggggaaggat gacattgata actccaaagc aggagcaggg    4080
ctcagcaggc ccagcccttc acccctggtt aatcaatata gcctcacagt gggcctggac    4140
ctgggaccac atgacactaa gtccctgctc aagtgtgtgg aatcactgtc cttcattgtt    4200
cgtgatgctg ctcacatcac ccctgacaac tttgaactct gtgtcaagac tctccgcatc    4260
tttgtagagg ccagtctgaa tggtgggtgc aaatcccagg ataaacgtgg caagagtcac    4320
aaatatgaca gcaaagggaa ccgcttcaag aaaaaaccga aggagggctc agtgcttcgg    4380
cggccccgaa cctccagcca gcatggcact cggggtggac atagtgatga ggaagaggat    4440
gaaggagtgc ctgccagcta ccatacggtg tctttacagg tcagtcagga cttgctggac    4500
ctgatgcaca ccctgcacac tcgggcagcc tctatctaca gctcatgggc agaggagcag    4560
cgccacctgg agtcaggtgg ccgaaagatt gaagctgact cacgcaccct ctgggcccac    4620
tgctggtgcc ctttattgca aggcatcgcc tgcttgtgct gtgatgcccg gcgccaagtg    4680
cggatgcagg ccctgacgta tctgcagcga gcacttctgg tgcatgacct acaaaagcta    4740
gatgccctgg aatgggagtc ctgctttaac aaggtgctgt tcctctact gaccaagctg    4800 ttagaaaata tcagccctgc agatgtgggt gggatggagg agacccggat gagggcttcc    4860
acgctgctct caaaggtctt cctgcagcac ctgtcccctc tgctgtcgct gtccaccttt    4920
```

| | |
|---|---|
| gctgccctgt ggctcaccat cctggacttc atggacaagt acatgcatgc aggctccagt | 4980 |
| gatttgctgt cagaagcaat ccctgagtcc ctgaaaaaca tgctcctggt gatggacacg | 5040 |
| gccgagatct tccacagtgc agatgcgaga ggaggcagcc cctctgccct ctgggagatc | 5100 |
| acctgggagc gcattgattg cttttttgcca cacttacgtg acgagctctt caagcagact | 5160 |
| gtcatccagg accccatgcc cacggaacct cacagccaaa acgctctggc ctccacccac | 5220 |
| ctgacccctg ctgctggtga ccccggccat ctaccttccc cagagatacc ctcagaagtg | 5280 |
| ggggcctgtg actcagagaa gcctgagggt acccgagcca ccagcagcag ctctccggga | 5340 |
| tcaccagtgg cctccagccc cagtagactg agtccttccc cagagggacc tcccccattg | 5400 |
| gcccagcccc cactaatcct gcagcccctg acttccccgc tgcaggtggg cgtgccaccc | 5460 |
| atggctctgc ccattatcct caaccctgca ctcatcgagg ccacctctcc ggtgcctctc | 5520 |
| ttgtccactc cccgtcctac agaccctatt cccacctctg aagtcaacta a | 5571 |

<210> SEQ ID NO 10
<211> LENGTH: 5568
<212> TYPE: DNA
<213> ORGANISM: Cricetulus griseus

<400> SEQUENCE: 10

| | |
|---|---|
| atggtggata agaatattta catcattcaa ggagaaatta acattgttgt tggcgccatc | 60 |
| aaacgaaatg cacgatggag cacccatata ccactggatg aagaacggga tcctctgctg | 120 |
| cacagtttca gtcatctaaa ggaggtctta aacagtgtaa cagaactctc agagattgag | 180 |
| ccaaatgtat tccttcgtcc atttctggaa gttattcgct ctgaagatac cactggtcct | 240 |
| atcactggcc tggcgctcac ctctgtcaac aaattcctgt cctatgcact catagatcca | 300 |
| actcatgagg gcacagcaga gggcatggag aacatggcag atgctgtcac tcatgcccgt | 360 |
| tttgtgggta cagaccctgc cagcgatgaa gttgtcctga tgaaaatcct ccaggttctt | 420 |
| cgaactctgt tgctaacccc agtgggtacc cacttaacaa atgaatctgt gtgtgagatt | 480 |
| atgcagtctt gcttccggat ttgctttgaa atgaggctta gtgagttatt gagaaaatcc | 540 |
| gcagagcaca ctctcgtaga catggtgcag ctgctcttca caaggttacc tcagtttaaa | 600 |
| gaagaaccca agagctatgt gggaaccaac atgaagaagc tgaaaatgag agcgggaggc | 660 |
| atgagcgact catccaagtg gaaaaagcag aaaagatccc ctcggccccc gcgtcacatg | 720 |
| accagagtca caccaggttc agagctgccc gccccaaatg gagccacctt atcctgtaac | 780 |
| ctcaccagtg gcatgccttt cattgatgtg ccctcatcca tctcctctgc aagttcagaa | 840 |
| gctgcctcag cagtggtcag tccctgtaca gacagtggcc tggaattatc ctcccagacc | 900 |
| acctccaagg aggacctcac tgacctagag caagctggtt cccaagggaa agcacaacc | 960 |
| acagagtctg ggagcaatga ataggagtt tccgatcagc ttgaccctca ggaagggtcc | 1020 |
| catgtggaaa aggcccagtc agcatcggtg gaatctatcc ctgaagtgtt ggaggagtgc | 1080 |
| acatctcctc ctgaccactc tgcctctgtc catgacatgg attatgtcaa tcccgggggt | 1140 |
| gttcgcttca cacagtcctc ccagaaggaa ggcacagctt tggttcctta tggtcttcct | 1200 |
| tgcatccgag agctcttccg cttccttatc tccctcacaa acccacatga ccgccacaac | 1260 |
| tcagagggta tgatccacat gggactgcat ttgctgacag tggctctgga gtcagcccct | 1320 |
| gtagcccagt gccagaccct cttgggtctc atcaaggatg agatgtgtcg ccacttattc | 1380 |
| cagctactca gtgtagagcg attgaacctg tatgctgctt ccctacgggt atgcttctta | 1440 |
| ctctttgaga gcatgcggga gcacctcaag ttccaattag agatgtacat gaaaaaactc | 1500 |

```
atggagatca tcactgttga aaacccccaag atgccttatg agatgaagga gatggcactg    1560
gaggccatcg tgcagctctg gcgcatcccc agctttgtca ctgagctcta tatcaactac    1620
gattgtgact actactgcgc caacctcttt gaagacctca ctaagctgct gtccaagaat    1680
gcctttcctg tgtctggtca actttatacc acacacctac tgtcccttga tgccctgttg    1740
acggttattg acagcactga ggctcactgt caagccaaag tcctcaacac tcttacccag    1800
caagagaaga aggagacatc cagacccagc tacgaggcag tggatagcac ccaagaagca    1860
aacagtactg aaagagccac cattgatggg aaagccacag gcatggcctc agatgcccta    1920
ggccttcatc ttcaaagtgg aggatggctg tcagcagagc atgggaagcc aagatgcaat    1980
gatgtggaag aagctggtga ctctggggct gacaaaaagt ttaccaggaa gccgcctcga    2040 tttcctgtc ttctgccaga tccacgggaa ctaattgaaa ttaagaacaa aaagaagctg    2100
ctgatcactg gcacagagca gttcaatcag aaacccaaga agggcatcca gtttctacag    2160
gaaaaaggtc tccttaccat cccaatggat aacacagagg tggcccagtg gctccgagag    2220
aaccctcggc tagacaagaa aatgattggg gagtttgtga gtgaccgaaa aaacattgac    2280
ctgttggaga gttttgtgag caccttcagc tttcagggtc tacggcttga tgaagctctc    2340
cgactctacc tggaagcctt ccgtttgccc ggggaagcac cagttattca caggttgctg    2400
gaggcattca cagagcactg gaggagttgt aatggctccc catttgccaa tagcgatgcc    2460
tgctttgccc tggcctatgc tgtcatcttg cttaatactg accagcataa ccacaatgtc    2520
cgcaaacaga atgtacccat gactctggag gagtttcgaa aaaacctaaa aggtgtgaat    2580
ggaggcaagg actttgagca agacatcctg gaggacatgt accatgccat caagaatgag    2640
gaaatcgtga tgcccgagga acagacaggc ctggttcgtg agaactatgt gtggagtgtg    2700
ctgctgcacc gaggtgccac ccctgagggt atattccttc gtgtacctcc tggcagctat    2760
gatcttgacc tcttcactat gacctgggc ccaactattg ctgctctctc ttatgtcttt    2820
gataaaagca ttgaggagac catcatccag aaagccatct caggtttcag gaagtgtgcc    2880
atgatctctg cccactatgg cctcagcgat gtgtttgaca atctcatcat ctctttgtgc    2940
aagttcacag ctctcagtag tgagtctatt gagaaccttc ccactgtgtt tggaagcaac    3000
cctaaagctc acattgcagc caagacagta ttccacttgg cccatcgtca tggtgacatc    3060
cttcgggagg gctggaagaa tatcatggag gctgtgctgc aactcttccg tgctcaactt    3120
ttaccccagg ctatggtgga ggtagaagat tttgtggatc ccaatggtaa gatctctcta    3180
cagcgggagg agatgccatc aaaccgagga gagtcatcgg tacttagctt tgtgagctgg    3240
ctgacgttga gtggtcctga gcagtctagt gtacggggcc cctccacaga gaaccaggag    3300
gccaagagag tggccttgga ctgtatcaag caatgtgacc agaaaaaat gatcacagaa    3360 agcaagttcc ttcagctgga atcattgcag gagctcatga aggctttggt ctcagtgaca    3420
gcagatgaag agacatacga tgaagaggat gctgctttct gtctggagat gctgctgagg    3480
attgtgttgg agaacaggga ccgtgtgggc tgtgtatggc agactgttag agaccatcta    3540
taccacttat gtgttcaggc acaagatttc tgctttctcg tggagcgggc agtggtgggg    3600
ctgctacgcc tcgcgattcg gctactccgg agagaagaga tcagtggcca ggtcctgctg    3660
tccctgcgca tcttgttact gatgaagccc agcgtgctgt ccagggtcag ccaccaggtt    3720
gcctacgggc tccatgaact cctcaagacc aatgcagcca acatccactc gggtgacgac    3780
tgggccaccc tcttcacatt gctggagtgt attggctcag gcgtgaagcc tccagatgct    3840
ctacaggcca cagccagggc tgatgctcct gatgctggag cgcagtcaga cagtgagctc    3900
```

```
ccatcctacc atcaaaatga tgtcagccta gaccgagggt acacttccga ctcagaagtc    3960
tacactgacc atggcaggcc tggcaagata caccgatctg ccacagatgc tgatatggtc    4020
aacagtggtt ggttagtggt ggggaaggat gacattgata actccaaagc aggagcaggg    4080
ctcagcaggc ccagcccttc acccctggtt aatcaatata gcctcacagt gggcctggac    4140
ctgggaccac atgacactaa gtccctgctc aagtgtgtgg aatcactgtc cttcattgtt    4200
cgtgatgctg ctcacatcac ccctgacaac tttgaactct gtgtcaagac tctccgcatc    4260
tttgtagagg ccagtctgaa tggtgggtgc aaatcccagg ataaacgtgg caagagtcac    4320
aaatatgaca gcaagggaa ccgcttcaag aaaaaaccga aggagggctc agtgcttcgg    4380
cggccccgaa cctccagcca gcatggcact cggggtggac atagtgatga ggaagaggat    4440
gaaggagtgc ctgccagcta ccatacggtg tctttacagg tcagtcagga cttgctggac    4500
ctgatgcaca ccctgcacac tcgggcagcc tctatctaca gctcatgggc agaggagcag    4560
cgccacctgg agtcaggtgg ccgaaagatt gaagctgact cacgcaccct ctgggccac    4620 tgctggtgcc ctttattgca aggcatcgcc tgcttgtgct gtgatgcccg gcgccaagtg    4680
cggatgcagg ccctgacgta tctgcagcga gcacttctgg tgcatgacct acaaaagcta    4740
gatgccctgg aatgggagtc ctgctttaac aaggtgctgt ttcctctact gaccaagctg    4800
ttagaaaata tcagccctgc agatgtgggt gggatggagg agacccggat gagggcttcc    4860
acgctgctct caaaggtctt cctgcagcac ctgtcccctc tgctgtcgct gtccaccttt    4920
gctgccctgt ggctcaccat cctggacttc atggacaagt acatgcatgc aggctccagt    4980
gatttgctgt cagaagcaat ccctgagtcc ctgaaaaaca tgctcctggt gatggacacg    5040
gccgagatct ccacagtgc agatgcgaga ggaggcagcc cctctgccct ctgggagatc    5100
acctgggagc gcattgattg cttttttgcca cacttacgtg acgagctctt caagcagact    5160
gtcatccagg accccatgcc cacggaacct cacagccaaa acgctctggc ctccacccac    5220 ctgaccctg ctgctggtga ccccggccat ctaccttccc cagagatacc ctcagaagtg    5280
ggggcctgtg actcagagaa gcctgagggt acccgagcca ccagcagcag ctctccggga    5340
tcaccagtgg cctccagccc cagtagactg agtccttccc cagagggacc tcccccattg    5400
gcccagcccc cactaatcct gcagcccctg acttccccgc tgcaggtggg cgtgccaccc    5460
atggctctgc ccattatcct caaccctgca ctcatcgagg ccacctctcc ggtgcctctc    5520
ttgtccactc cccgtcctac agaccctatt cccacctctg aagtcaac              5568

<210> SEQ ID NO 11
<211> LENGTH: 671
<212> TYPE: DNA
<213> ORGANISM: Canis familiaris

<400> SEQUENCE: 11
attgcccttc gattttcctg tctcctgcca gatccacggg aactgattga aattaaaaac      60
aaaaagaagc tgctaatcac tggcacagag cagttcaacc agaaaccaaa gaagggaatc     120
cagtttctgc aggagaaagg cctcctcacc atcccaatgg acaacacaga ggtagcccag     180
tggctccgag agaaccctcg gctggacaag aaaatgattg agagtttgt gagtgaccgc     240 aaaaacattg acctgttgga gagctttgtg agcaccttca gctttcaggg tctgcggctg     300
gatgaagctc ttcgtctcta cctggaagcc tttcgcttac ctggggaagc accagtcatc     360
cagaggttgc tggaggcatt cacagagcat ggaggaatt gtaatggctc cccatttgcc     420
aatagcgatg cctgctttgc tctggcctat gctgtcatct tgcttaatac tgaccagcac     480
```

-continued

| aaccacaacg ttcgcaaaca gaatgcaccc atgactctag aggagtttcg caaaaaccta | 540 |
| aaaggtgtga atggaggcaa ggactttgag caagacatcc tggaggacat gtaccatgcc | 600 |
| atcaagaatg aggaaattgt gatgcctgaa gagcagacag gcttggttcg ggagaactat | 660 |
| gtgtggaagg g | 671 |

<210> SEQ ID NO 12
<211> LENGTH: 51
<212> TYPE: DNA
<213> ORGANISM: Canis familiaris

<400> SEQUENCE: 12

| gtccttccac ctgtccacaa gcatggttgt gaggtgggag caaaaccaac g | 51 |

<210> SEQ ID NO 13
<211> LENGTH: 76
<212> TYPE: DNA
<213> ORGANISM: Canis familiaris

<400> SEQUENCE: 13

| ccgcgctagc ctgaggcata gtcaggcacg tcataaggat agccgttctt ctggttccgg | 60 |
| agctgattgg acagcc | 76 |

<210> SEQ ID NO 14
<211> LENGTH: 31
<212> TYPE: DNA
<213> ORGANISM: Canis familiaris

<400> SEQUENCE: 14

| cgattttcct gtctcctgcc agatccacgg g | 31 |

<210> SEQ ID NO 15
<211> LENGTH: 27
<212> TYPE: DNA
<213> ORGANISM: Canis familiaris

<400> SEQUENCE: 15

| ccacacatag ttctcccgaa ccaagcc | 27 |

<210> SEQ ID NO 16
<211> LENGTH: 5568
<212> TYPE: DNA
<213> ORGANISM: Cricetulus griseus

<400> SEQUENCE: 16

| atggtggata gaatattta catcattcaa ggagaaatta acattgttgt tggcgccatc | 60 |
| aaacgaaatg cacgatggag cacccatata ccactggatg aagaacggga tcctctgctg | 120 |
| cacagtttca gtcatctaaa ggaggtctta aacagtgtaa cagaactctc agagattgag | 180 |
| ccaaatgtat tccttcgtcc atttctggaa gttattcgct ctgaagatac cactggtcct | 240 |
| atcactggcc tggcgctcac ctctgtcaac aaattcctgt cctatgcact catagatcca | 300 |
| actcatgagg gcacagcaga gggcatggag aacatgcag atgctgtcac tcatgcccgt | 360 |
| tttgtgggta cagaccctgc cagcgatgaa gttgtcctga tgaaaatcct ccaggttctt | 420 |
| cgaactctgt tgctaacccc agtgggtacc cacttaacaa tgaatctgt gtgtgagatt | 480 |
| atgcagtctt gcttccggat ttgctttgaa atgaggctta gtgagttatt gagaaaatcc | 540 |
| gcagagcaca ctctcgtaga catggtgcag ctgctcttca aaggttacc tcagtttaaa | 600 |
| gaagaaccca gagctatgt gggaaccaac atgaagaagc tgaaaatgag agcgggaggc | 660 |

```
atgagcgact catccaagtg gaaaaagcag aaaagatccc ctcggccccc gcgtcacatg    720
accagagtca caccaggttc agagctgccc gccccaaatg gagccaccct atcctgtaac    780
ctcaccagtg gcatgccttt cattgatgtg ccctcatcca tctcctctgc aagttcagaa    840
gctgcctcag cagtggtcag tccctgtaca gacagtggcc tggaattatc ctcccagacc    900
acctccaagg aggacctcac tgacctagag caagctggtt ccccaaggga agcacaacc     960
acagagtctg ggagcaatga gataggagtt tccgatcagc ttgaccctca ggaagggtcc   1020
catgtggaaa aggcccagtc agcatcggtg gaatctatcc ctgaagtgtt ggaggagtgc   1080
acatctcctc ctgaccactc tgcctctgtc catgacatgg attatgtcaa tccccggggt   1140
gttcgcttca cacagtcctc ccagaaggaa ggcacagctt tggttcctta tggtcttcct   1200
tgcatccgag agctcttccg cttccttatc tccctcacaa acccacatga ccgccacaac   1260
tcagagggta tgatccacat gggactgcat ttgctgacag tggctctgga gtcagcccct   1320
gtagcccagt gccagaccct cttgggtctc atcaaggatg agatgtgtcg ccacttattc   1380
cagctactca gtgtagagcg attgaacctg tatgctgctt ccctacgggt atgcttctta   1440
ctctttgaga gcatgcggga gcacctcaag ttccaattag agatgtacat gaaaaaactc   1500
atggagatca tcactgttga aaaccccaag atgccttatg agatgaagga gatggcactg   1560
gaggccatcg tgcagctctg gcgcatcccc agctttgtca ctgagctcta tatcaactac   1620
gattgtgact actactgcgc caacctcttt gaagacctca ctaagctgct gtccaagaat   1680
gcctttcctg tgtctggtca actttatacc acacacctac tgtcccttga tgccctgttg   1740
acggttattg acagcactga ggctcactgt caagccaaag tcctcaacac tcttacccag   1800
caagagaaga aggagacatc cagacccagc tacgaggcag tggatagcac caagaagca   1860
aacagtactg aaagagccac cattgatggg aaagccacag gcatggcctc agatgcccta   1920
ggccttcatc ttcaaagtgg aggatggctg tcagcagagc atgggaagcc aagatgcaat   1980
gatgtggaag aagctggtga ctctggggct gacaaaaagt ttaccaggaa gccgcctcga   2040
ttttcctgtc ttctgccaga tccacgggaa ctaattgaaa ttaagaacaa aaagaagctg   2100
ctgatcactg gcacagagca gttcaatcag aaacccaaga agggcatcca gtttctacag   2160
gaaaaaggtc tccttaccat cccaatggat aacacagagg tggcccagtg gctccgagag   2220
aaccctcggc tagacaagaa aatgattggg gagtttgtga gtgaccgaaa aacattgac    2280
ctgttggaga gttttgtgag caccttcagc tttcagggtc tacggcttga tgaagctctc   2340
cgactctacc tggaagcctt ccgtttgccc gggaaggcac cagttattca caggttgctg   2400
gaggcattca cagagcactg gaggagttgt aatggctccc catttgccaa tagcgatgcc   2460
tgctttgccc tggcctatgc tgtcatcatg cttaatactg accagcataa ccacaatgtc   2520
cgcaaacaga atgtacccat gactctggag gagtttcgaa aaacctaaa aggtgtgaat   2580
ggaggcaagg actttgagca agacatcctg gaggacatgt accatgccat caagaatgag   2640
gaaatcgtga tgcccgagga acagacaggc ctggttcgtg agaactatgt gtggagtgtg   2700
ctgctgcacc gaggtgccac ccctgagggt atattccttc gtgtacctcc tggcagctat   2760
gatcttgacc tcttcactat gacctggggc ccaactattg ctgctctctc ttatgtcttt   2820
gataaaagca ttgaggagac catcatccag aaagccatct caggtttcag gaagtgtgcc   2880
atgatctctg cccactatgg cctcagcgat gtgtttgaca atctcatcat ctctttgtgc   2940
aagttcacag ctctcagtag tgagtctatt gagaaccttc ccactgtgtt tggaagcaac   3000
cctaaagctc acattgcagc caagacagta ttccacttgg cccatcgtca tggtgacatc   3060
```

```
cttcgggagg gctggaagaa tatcatggag gctgtgctgc aactcttccg tgctcaactt    3120
ttaccccagg ctatggtgga ggtagaagat tttgtggatc ccaatggtaa gatctctcta    3180
cagcgggagg agatgccatc aaaccgagga gagtcatcgg tacttagctt tgtgagctgg    3240
ctgacgttga gtggtcctga gcagtctagt gtacggggcc cctccacaga gaaccaggag    3300
gccaagagag tggccttgga ctgtatcaag caatgtgacc cagaaaaaat gatcacagaa    3360
agcaagttcc ttcagctgga atcattgcag gagctcatga aggctttggt ctcagtgaca    3420
gcagatgaag agacatacga tgaagaggat gctgctttct gtctggagat gctgctgagg    3480
attgtgttgg agaacaggga ccgtgtgggc tgtgtatggc agactgttag agaccatcta    3540
taccacttat gtgttcaggc acaagatttc tgctttctcg tggagcgggc agtggtgggg    3600
ctgctacgcc tcgcgattcg gctactccgg agagaagaga tcagtggcca ggtcctgctg    3660
tccctgcgca tcttgttact gatgaagccc agcgtgctgt ccagggtcag ccaccaggtt    3720
gcctacgggc tccatgaact cctcaagacc aatgcagcca acatccactc gggtgacgac    3780
tgggccaccc tcttcacatt gctggagtgt attggctcag gcgtgaagcc tccagatgct    3840
ctacaggcca cagccagggc tgatgctcct gatgctggag cgcagtcaga cagtgagctc    3900
ccatcctacc atcaaaatga tgtcagccta gaccgagggt acacttccga ctcagaagtc    3960
tacactgacc atggcaggcc tggcaagata caccgatctg ccacagatgc tgatatggtc    4020
aacagtggtt ggttagtggt ggggaaggat gacattgata actccaaagc aggagcaggg    4080
ctcagcaggc ccagcccttc acccctggtt aatcaatata gcctcacagt gggcctggac    4140
ctgggaccac atgacactaa gtccctgctc aagtgtgtgg aatcactgtc cttcattgtt    4200
cgtgatgctg ctcacatcac ccctgacaac tttgaactct gtgtcaagac tctccgcatc    4260
tttgtagagg ccagtctgaa tggtgggtgc aaatcccagg ataaacgtgg caagagtcac    4320
aaatatgaca gcaaagggaa ccgcttcaag aaaaaaccga aggagggctc agtgcttcgg    4380
cggccccgaa cctccagcca gcatggcact cggggtggac atagtgatga ggaagaggat    4440
gaaggagtgc ctgccagcta ccatacggtg tctttacagg tcagtcagga cttgctggac    4500
ctgatgcaca ccctgcacac tcgggcagcc tctatctaca gctcatgggc agaggagcag    4560
cgccacctgg agtcaggtgg ccgaaagatt gaagctgact cacgcaccct ctgggccac    4620 tgctggtgcc ctttattgca aggcatcgcc tgcttgtgct gtgatgcccg cgccaagtg    4680 cggatgcagg ccctgacgta tctgcagcga gcacttctgg tgcatgacct acaaaagcta    4740
gatgccctgg aatgggagtc ctgctttaac aaggtgctgt ttcctctact gaccaagctg    4800
ttagaaaata tcagccctgc agatgtgggt gggatggagg agaccggat gagggcttcc    4860 acgctgctct caaaggtctt cctgcagcac ctgtcccctc tgctgtcgct gtccaccttt    4920
gctgccctgt ggctcaccat cctggacttc atggacaagt acatgcatgc aggctccagt    4980
gatttgctgt cagaagcaat ccctgagtcc ctgaaaaaca tgctcctggt gatggacacg    5040
gccgagatct tccacagtgc agatgcgaga ggaggcagcc cctctgccct ctgggagatc    5100
acctgggagc gcattgattg cttttttgcca cacttacgtg acgagctctt caagcagact    5160
gtcatccagg accccatgcc cacggaacct cacagccaaa acgctctggc ctccacccac    5220
ctgacccctg ctgctggtga ccccggccat ctaccttccc cagagatacc ctcagaagtg    5280
ggggcctgtg actcagagaa gcctgagggt acccgagcca ccagcagcag ctctccggga    5340
tcaccagtgg cctccagccc cagtagactg agtccttccc cagagggacc tccccattg    5400 gcccagcccc cactaatcct gcagcccctg acttccccgc tgcaggtggg cgtgccaccc    5460
```

-continued

```
atggctctgc ccattatcct caaccctgca ctcatcgagg ccacctctcc ggtgcctctc       5520
ttgtccactc cccgtcctac agaccctatt cccacctctg aagtcaac                    5568
```

```
<210> SEQ ID NO 17
<211> LENGTH: 28
<212> TYPE: DNA
<213> ORGANISM: Homo sapiens

<400> SEQUENCE: 17
gtccttccac ctgtccacaa gcatgggg                                          28

<210> SEQ ID NO 18
<211> LENGTH: 76
<212> TYPE: DNA
<213> ORGANISM: Homo sapiens

<400> SEQUENCE: 18
ccgcgctagc ctgaggcata gtcaggcacg tcataaggat agccgttctt ctggttccgg       60
agctgattgg acagcc                                                        76

<210> SEQ ID NO 19
<211> LENGTH: 34
<212> TYPE: DNA
<213> ORGANISM: Homo sapiens

<400> SEQUENCE: 19
ggccgaattc atggcggagg cggaagggga aagc                                   34

<210> SEQ ID NO 20
<211> LENGTH: 41
<212> TYPE: DNA
<213> ORGANISM: Homo sapiens

<400> SEQUENCE: 20
ccggctcgag tcagtcaggc agggttaagg tagccacctc g                           41

<210> SEQ ID NO 21
<211> LENGTH: 1856
<212> TYPE: PRT
<213> ORGANISM: Cricetulus griseus

<400> SEQUENCE: 21

Met Val Asp Lys Asn Ile Tyr Ile Ile Gln Gly Glu Ile Asn Ile Val
1               5                   10                  15

Val Gly Ala Ile Lys Arg Asn Ala Arg Trp Ser Thr His Ile Pro Leu
            20                  25                  30

Asp Glu Glu Arg Asp Pro Leu Leu His Ser Phe Ser His Leu Lys Glu
        35                  40                  45

Val Leu Asn Ser Val Thr Glu Leu Ser Glu Ile Glu Pro Asn Val Phe
    50                  55                  60

Leu Arg Pro Phe Leu Glu Val Ile Arg Ser Glu Asp Thr Thr Gly Pro
65                  70                  75                  80

Ile Thr Gly Leu Ala Leu Thr Ser Val Asn Lys Phe Leu Ser Tyr Ala
                85                  90                  95

Leu Ile Asp Pro Thr His Glu Gly Thr Ala Glu Gly Met Glu Asn Met
            100                 105                 110

Ala Asp Ala Val Thr His Ala Arg Phe Val Gly Thr Asp Pro Ala Ser
        115                 120                 125

Asp Glu Val Val Leu Met Lys Ile Leu Gln Val Leu Arg Thr Leu Leu
```

```
                130                 135                 140
Leu Thr Pro Val Gly Thr His Leu Thr Asn Glu Ser Val Cys Glu Ile
145                 150                 155                 160

Met Gln Ser Cys Phe Arg Ile Cys Phe Glu Met Arg Leu Ser Glu Leu
                165                 170                 175

Leu Arg Lys Ser Ala Glu His Thr Leu Val Asp Met Val Gln Leu Leu
                180                 185                 190

Phe Thr Arg Leu Pro Gln Phe Lys Glu Glu Pro Lys Ser Tyr Val Gly
                195                 200                 205

Thr Asn Met Lys Lys Leu Lys Met Arg Ala Gly Gly Met Ser Asp Ser
                210                 215                 220

Ser Lys Trp Lys Lys Gln Lys Arg Ser Pro Arg Pro Arg His Met
225                 230                 235                 240

Thr Arg Val Thr Pro Gly Ser Glu Leu Pro Ala Pro Asn Gly Ala Thr
                245                 250                 255

Leu Ser Cys Asn Leu Thr Ser Gly Met Pro Phe Ile Asp Val Pro Ser
                260                 265                 270

Ser Ile Ser Ser Ala Ser Ser Glu Ala Ala Ser Ala Val Val Ser Pro
                275                 280                 285

Cys Thr Asp Ser Gly Leu Glu Leu Ser Ser Gln Thr Thr Ser Lys Glu
                290                 295                 300

Asp Leu Thr Asp Leu Glu Gln Ala Gly Ser Pro Arg Glu Ser Thr Thr
305                 310                 315                 320

Thr Glu Ser Gly Ser Asn Glu Ile Gly Val Ser Asp Gln Leu Asp Pro
                325                 330                 335

Gln Glu Gly Ser His Val Glu Lys Ala Gln Ser Ala Ser Val Glu Ser
                340                 345                 350

Ile Pro Glu Val Leu Glu Glu Cys Thr Ser Pro Pro Asp His Ser Ala
                355                 360                 365

Ser Val His Asp Met Asp Tyr Val Asn Pro Arg Gly Val Arg Phe Thr
                370                 375                 380

Gln Ser Ser Gln Lys Glu Gly Thr Ala Leu Val Pro Tyr Gly Leu Pro
385                 390                 395                 400

Cys Ile Arg Glu Leu Phe Arg Phe Leu Ile Ser Leu Thr Asn Pro His
                405                 410                 415

Asp Arg His Asn Ser Glu Gly Met Ile His Met Gly Leu His Leu Leu
                420                 425                 430

Thr Val Ala Leu Glu Ser Ala Pro Val Ala Gln Cys Gln Thr Leu Leu
                435                 440                 445

Gly Leu Ile Lys Asp Glu Met Cys Arg His Leu Phe Gln Leu Leu Ser
450                 455                 460

Val Glu Arg Leu Asn Leu Tyr Ala Ala Ser Leu Arg Val Cys Phe Leu
465                 470                 475                 480

Leu Phe Glu Ser Met Arg Glu His Leu Lys Phe Gln Leu Glu Met Tyr
                485                 490                 495

Met Lys Lys Leu Met Glu Ile Ile Thr Val Glu Asn Pro Lys Met Pro
                500                 505                 510

Tyr Glu Met Lys Glu Met Ala Leu Glu Ala Ile Val Gln Leu Trp Arg
                515                 520                 525

Ile Pro Ser Phe Val Thr Glu Leu Tyr Ile Asn Tyr Asp Cys Asp Tyr
                530                 535                 540

Tyr Cys Ala Asn Leu Phe Glu Asp Leu Thr Lys Leu Leu Ser Lys Asn
545                 550                 555                 560
```

-continued

```
Ala Phe Pro Val Ser Gly Gln Leu Tyr Thr Thr His Leu Leu Ser Leu
            565                 570                 575
Asp Ala Leu Leu Thr Val Ile Asp Ser Thr Glu Ala His Cys Gln Ala
                580                 585                 590
Lys Val Leu Asn Thr Leu Thr Gln Gln Glu Lys Lys Glu Thr Ser Arg
            595                 600                 605
Pro Ser Tyr Glu Ala Val Asp Ser Thr Gln Glu Ala Asn Ser Thr Glu
            610                 615                 620
Arg Ala Thr Ile Asp Gly Lys Ala Thr Gly Met Ala Ser Asp Ala Leu
625                 630                 635                 640
Gly Leu His Leu Gln Ser Gly Gly Trp Leu Ser Ala Glu His Gly Lys
                645                 650                 655
Pro Arg Cys Asn Asp Val Glu Glu Ala Gly Asp Ser Gly Ala Asp Lys
            660                 665                 670
Lys Phe Thr Arg Lys Pro Pro Arg Phe Ser Cys Leu Leu Pro Asp Pro
            675                 680                 685
Arg Glu Leu Ile Glu Ile Lys Asn Lys Lys Leu Leu Ile Thr Gly
690                 695                 700
Thr Glu Gln Phe Asn Gln Lys Pro Lys Lys Gly Ile Gln Phe Leu Gln
705                 710                 715                 720
Glu Lys Gly Leu Leu Thr Ile Pro Met Asp Asn Thr Glu Val Ala Gln
                725                 730                 735
Trp Leu Arg Glu Asn Pro Arg Leu Asp Lys Lys Met Ile Gly Glu Phe
                740                 745                 750
Val Ser Asp Arg Lys Asn Ile Asp Leu Leu Glu Ser Phe Val Ser Thr
            755                 760                 765
Phe Ser Phe Gln Gly Leu Arg Leu Asp Glu Ala Leu Arg Leu Tyr Leu
            770                 775                 780
Glu Ala Phe Arg Leu Pro Gly Glu Ala Pro Val Ile His Arg Leu Leu
785                 790                 795                 800
Glu Ala Phe Thr Glu His Trp Arg Ser Cys Asn Gly Ser Pro Phe Ala
                805                 810                 815
Asn Ser Asp Ala Cys Phe Ala Leu Ala Tyr Ala Val Ile Leu Leu Asn
            820                 825                 830
Thr Asp Gln His Asn His Asn Val Arg Lys Gln Asn Val Pro Met Thr
            835                 840                 845
Leu Glu Glu Phe Arg Lys Asn Leu Lys Gly Val Asn Gly Gly Lys Asp
850                 855                 860
Phe Glu Gln Asp Ile Leu Glu Asp Met Tyr His Ala Ile Lys Asn Glu
865                 870                 875                 880
Glu Ile Val Met Pro Glu Glu Gln Thr Gly Leu Val Arg Glu Asn Tyr
            885                 890                 895
Val Trp Ser Val Leu Leu His Arg Gly Ala Thr Pro Glu Gly Ile Phe
            900                 905                 910
Leu Arg Val Pro Pro Gly Ser Tyr Asp Leu Asp Leu Phe Thr Met Thr
            915                 920                 925
Trp Gly Pro Thr Ile Ala Ala Leu Ser Tyr Val Phe Asp Lys Ser Ile
            930                 935                 940
Glu Glu Thr Ile Ile Gln Lys Ala Ile Ser Gly Phe Arg Lys Cys Ala
945                 950                 955                 960
Met Ile Ser Ala His Tyr Gly Leu Ser Asp Val Phe Asp Asn Leu Ile
                965                 970                 975
Ile Ser Leu Cys Lys Phe Thr Ala Leu Ser Ser Glu Ser Ile Glu Asn
            980                 985                 990
```

```
Leu Pro Thr Val Phe Gly Ser Asn  Pro Lys Ala His Ile  Ala Ala Lys
        995                 1000                1005
Thr Val  Phe His Leu Ala His  Arg His Gly Asp Ile  Leu Arg Glu
    1010              1015                 1020
Gly Trp  Lys Asn Ile Met Glu  Ala Val Leu Gln Leu  Phe Arg Ala
    1025              1030                 1035
Gln Leu  Leu Pro Gln Ala Met  Val Glu Val Glu Asp  Phe Val Asp
    1040              1045                 1050
Pro Asn  Gly Lys Ile Ser Leu  Gln Arg Glu Glu Met  Pro Ser Asn
    1055              1060                 1065
Arg Gly  Glu Ser Ser Val Leu  Ser Phe Val Ser Trp  Leu Thr Leu
    1070              1075                 1080
Ser Gly  Pro Glu Gln Ser Ser  Val Arg Gly Pro Ser  Thr Glu Asn
    1085              1090                 1095
Gln Glu  Ala Lys Arg Val Ala  Leu Asp Cys Ile Lys  Gln Cys Asp
    1100              1105                 1110
Pro Glu  Lys Met Ile Thr Glu  Ser Lys Phe Leu Gln  Leu Glu Ser
    1115              1120                 1125
Leu Gln  Glu Leu Met Lys Ala  Leu Val Ser Val Thr  Ala Asp Glu
    1130              1135                 1140
Glu Thr  Tyr Asp Glu Glu Asp  Ala Ala Phe Cys Leu  Glu Met Leu
    1145              1150                 1155
Leu Arg  Ile Val Leu Glu Asn  Arg Asp Arg Val Gly  Cys Val Trp
    1160              1165                 1170
Gln Thr  Val Arg Asp His Leu  Tyr His Leu Cys Val  Gln Ala Gln
    1175              1180                 1185
Asp Phe  Cys Phe Leu Val Glu  Arg Ala Val Val Gly  Leu Leu Arg
    1190              1195                 1200
Leu Ala  Ile Arg Leu Leu Arg  Arg Glu Glu Ile Ser  Gly Gln Val
    1205              1210                 1215
Leu Leu  Ser Leu Arg Ile Leu  Leu Leu Met Lys Pro  Ser Val Leu
    1220              1225                 1230
Ser Arg  Val Ser His Gln Val  Ala Tyr Gly Leu His  Glu Leu Leu
    1235              1240                 1245
Lys Thr  Asn Ala Ala Asn Ile  His Ser Gly Asp Asp  Trp Ala Thr
    1250              1255                 1260
Leu Phe  Thr Leu Leu Glu Cys  Ile Gly Ser Gly Val  Lys Pro Pro
    1265              1270                 1275
Asp Ala  Leu Gln Ala Thr Ala  Arg Ala Asp Ala Pro  Asp Ala Gly
    1280              1285                 1290
Ala Gln  Ser Asp Ser Glu Leu  Pro Ser Tyr His Gln  Asn Asp Val
    1295              1300                 1305
Ser Leu  Asp Arg Gly Tyr Thr  Ser Asp Ser Glu Val  Tyr Thr Asp
    1310              1315                 1320
His Gly  Arg Pro Gly Lys Ile  His Arg Ser Ala Thr  Asp Ala Asp
    1325              1330                 1335
Met Val  Asn Ser Gly Trp Leu  Val Val Gly Lys Asp  Asp Ile Asp
    1340              1345                 1350
Asn Ser  Lys Ala Gly Ala Gly  Leu Ser Arg Pro Ser  Pro Ser Pro
    1355              1360                 1365
Leu Val  Asn Gln Tyr Ser Leu  Thr Val Gly Leu Asp  Leu Gly Pro
    1370              1375                 1380
His Asp  Thr Lys Ser Leu Leu  Lys Cys Val Glu Ser  Leu Ser Phe
```

```
                    1385                1390                1395

Ile Val Arg Asp Ala Ala His Ile Thr Pro Asp Asn Phe Glu Leu
    1400                1405                1410

Cys Val Lys Thr Leu Arg Ile Phe Val Glu Ala Ser Leu Asn Gly
    1415                1420                1425

Gly Cys Lys Ser Gln Asp Lys Arg Gly Lys Ser His Lys Tyr Asp
    1430                1435                1440

Ser Lys Gly Asn Arg Phe Lys Lys Lys Pro Lys Glu Gly Ser Val
    1445                1450                1455

Leu Arg Arg Pro Arg Thr Ser Ser Gln His Gly Thr Arg Gly Gly
    1460                1465                1470

His Ser Asp Glu Glu Glu Asp Glu Gly Val Pro Ala Ser Tyr His
    1475                1480                1485

Thr Val Ser Leu Gln Val Ser Gln Asp Leu Leu Asp Leu Met His
    1490                1495                1500

Thr Leu His Thr Arg Ala Ala Ser Ile Tyr Ser Ser Trp Ala Glu
    1505                1510                1515

Glu Gln Arg His Leu Glu Ser Gly Gly Arg Lys Ile Glu Ala Asp
    1520                1525                1530

Ser Arg Thr Leu Trp Ala His Cys Trp Cys Pro Leu Leu Gln Gly
    1535                1540                1545

Ile Ala Cys Leu Cys Cys Asp Ala Arg Arg Gln Val Arg Met Gln
    1550                1555                1560

Ala Leu Thr Tyr Leu Gln Arg Ala Leu Leu Val His Asp Leu Gln
    1565                1570                1575

Lys Leu Asp Ala Leu Glu Trp Glu Ser Cys Phe Asn Lys Val Leu
    1580                1585                1590

Phe Pro Leu Leu Thr Lys Leu Leu Glu Asn Ile Ser Pro Ala Asp
    1595                1600                1605

Val Gly Gly Met Glu Glu Thr Arg Met Arg Ala Ser Thr Leu Leu
    1610                1615                1620

Ser Lys Val Phe Leu Gln His Leu Ser Pro Leu Leu Ser Leu Ser
    1625                1630                1635

Thr Phe Ala Ala Leu Trp Leu Thr Ile Leu Asp Phe Met Asp Lys
    1640                1645                1650

Tyr Met His Ala Gly Ser Ser Asp Leu Leu Ser Glu Ala Ile Pro
    1655                1660                1665

Glu Ser Leu Lys Asn Met Leu Leu Val Met Asp Thr Ala Glu Ile
    1670                1675                1680

Phe His Ser Ala Asp Ala Arg Gly Gly Ser Pro Ser Ala Leu Trp
    1685                1690                1695

Glu Ile Thr Trp Glu Arg Ile Asp Cys Phe Leu Pro His Leu Arg
    1700                1705                1710

Asp Glu Leu Phe Lys Gln Thr Val Ile Gln Asp Pro Met Pro Thr
    1715                1720                1725

Glu Pro His Ser Gln Asn Ala Leu Ala Ser Thr His Leu Thr Pro
    1730                1735                1740

Ala Ala Gly Asp Pro Gly His Leu Pro Ser Pro Glu Ile Pro Ser
    1745                1750                1755

Glu Val Gly Ala Cys Asp Ser Glu Lys Pro Glu Gly Thr Arg Ala
    1760                1765                1770

Thr Ser Ser Ser Ser Pro Gly Ser Pro Val Ala Ser Ser Pro Ser
    1775                1780                1785
```

-continued

```
Arg Leu Ser Pro Ser Pro Glu Gly Pro Pro Leu Ala Gln Pro
    1790            1795            1800

Pro Leu Ile Leu Gln Pro Leu Thr Ser Pro Leu Gln Val Gly Val
    1805            1810            1815

Pro Pro Met Ala Leu Pro Ile Ile Leu Asn Pro Ala Leu Ile Glu
    1820            1825            1830

Ala Thr Ser Pro Val Pro Leu Leu Ser Thr Pro Arg Pro Thr Asp
    1835            1840            1845

Pro Ile Pro Thr Ser Glu Val Asn
    1850            1855

<210> SEQ ID NO 22
<211> LENGTH: 1856
<212> TYPE: PRT
<213> ORGANISM: Cricetulus griseus

<400> SEQUENCE: 22

Met Val Asp Lys Asn Ile Tyr Ile Ile Gln Gly Glu Ile Asn Ile Val
1               5                   10                  15

Val Gly Ala Ile Lys Arg Asn Ala Arg Trp Ser Thr His Ile Pro Leu
            20                  25                  30

Asp Glu Glu Arg Asp Pro Leu Leu His Ser Phe Ser His Leu Lys Glu
        35                  40                  45

Val Leu Asn Ser Val Thr Glu Leu Ser Glu Ile Glu Pro Asn Val Phe
    50                  55                  60

Leu Arg Pro Phe Leu Glu Val Ile Arg Ser Glu Asp Thr Thr Gly Pro
65                  70                  75                  80

Ile Thr Gly Leu Ala Leu Thr Ser Val Asn Lys Phe Leu Ser Tyr Ala
                85                  90                  95

Leu Ile Asp Pro Thr His Glu Gly Thr Ala Glu Gly Met Glu Asn Met
            100                 105                 110

Ala Asp Ala Val Thr His Ala Arg Phe Val Gly Thr Asp Pro Ala Ser
        115                 120                 125

Asp Glu Val Val Leu Met Lys Ile Leu Gln Val Leu Arg Thr Leu Leu
    130                 135                 140

Leu Thr Pro Val Gly Thr His Leu Thr Asn Glu Ser Val Cys Glu Ile
145                 150                 155                 160

Met Gln Ser Cys Phe Arg Ile Cys Phe Glu Met Arg Leu Ser Glu Leu
                165                 170                 175

Leu Arg Lys Ser Ala Glu His Thr Leu Val Asp Met Val Gln Leu Leu
            180                 185                 190

Phe Thr Arg Leu Pro Gln Phe Lys Glu Glu Pro Lys Ser Tyr Val Gly
        195                 200                 205

Thr Asn Met Lys Lys Leu Lys Met Arg Ala Gly Gly Met Ser Asp Ser
    210                 215                 220

Ser Lys Trp Lys Lys Gln Lys Arg Ser Pro Arg Pro Arg His Met
225                 230                 235                 240

Thr Arg Val Thr Pro Gly Ser Glu Leu Pro Ala Pro Asn Gly Ala Thr
                245                 250                 255

Leu Ser Cys Asn Leu Thr Ser Gly Met Pro Phe Ile Asp Val Pro Ser
            260                 265                 270

Ser Ile Ser Ser Ala Ser Ser Glu Ala Ala Ser Ala Val Val Ser Pro
        275                 280                 285

Cys Thr Asp Ser Gly Leu Glu Leu Ser Ser Gln Thr Thr Ser Lys Glu
    290                 295                 300
```

```
Asp Leu Thr Asp Leu Glu Gln Ala Gly Ser Pro Arg Glu Ser Thr Thr
305                 310                 315                 320

Thr Glu Ser Gly Ser Asn Glu Ile Gly Val Ser Asp Gln Leu Asp Pro
            325                 330                 335

Gln Glu Gly Ser His Val Glu Lys Ala Gln Ser Ala Ser Val Glu Ser
        340                 345                 350

Ile Pro Glu Val Leu Glu Glu Cys Thr Ser Pro Pro Asp His Ser Ala
    355                 360                 365

Ser Val His Asp Met Asp Tyr Val Asn Pro Arg Gly Val Arg Phe Thr
370                 375                 380

Gln Ser Ser Gln Lys Glu Gly Thr Ala Leu Val Pro Tyr Gly Leu Pro
385                 390                 395                 400

Cys Ile Arg Glu Leu Phe Arg Phe Leu Ile Ser Leu Thr Asn Pro His
            405                 410                 415

Asp Arg His Asn Ser Glu Gly Met Ile His Met Gly Leu His Leu Leu
        420                 425                 430

Thr Val Ala Leu Glu Ser Ala Pro Val Ala Gln Cys Gln Thr Leu Leu
    435                 440                 445

Gly Leu Ile Lys Asp Glu Met Cys Arg His Leu Phe Gln Leu Leu Ser
450                 455                 460

Val Glu Arg Leu Asn Leu Tyr Ala Ala Ser Leu Arg Val Cys Phe Leu
465                 470                 475                 480

Leu Phe Glu Ser Met Arg Glu His Leu Lys Phe Gln Leu Glu Met Tyr
            485                 490                 495

Met Lys Lys Leu Met Glu Ile Ile Thr Val Glu Asn Pro Lys Met Pro
        500                 505                 510

Tyr Glu Met Lys Glu Met Ala Leu Glu Ala Ile Val Gln Leu Trp Arg
    515                 520                 525

Ile Pro Ser Phe Val Thr Glu Leu Tyr Ile Asn Tyr Asp Cys Asp Tyr
530                 535                 540

Tyr Cys Ala Asn Leu Phe Glu Asp Leu Thr Lys Leu Leu Ser Lys Asn
545                 550                 555                 560

Ala Phe Pro Val Ser Gly Gln Leu Tyr Thr Thr His Leu Leu Ser Leu
            565                 570                 575

Asp Ala Leu Leu Thr Val Ile Asp Ser Thr Glu Ala His Cys Gln Ala
        580                 585                 590

Lys Val Leu Asn Thr Leu Thr Gln Gln Glu Lys Lys Glu Thr Ser Arg
    595                 600                 605

Pro Ser Tyr Glu Ala Val Asp Ser Thr Gln Glu Ala Asn Ser Thr Glu
610                 615                 620

Arg Ala Thr Ile Asp Gly Lys Ala Thr Gly Met Ala Ser Asp Ala Leu
625                 630                 635                 640

Gly Leu His Leu Gln Ser Gly Gly Trp Leu Ser Ala Glu His Gly Lys
            645                 650                 655

Pro Arg Cys Asn Asp Val Glu Glu Ala Gly Asp Ser Gly Ala Asp Lys
        660                 665                 670

Lys Phe Thr Arg Lys Pro Pro Arg Phe Ser Cys Leu Leu Pro Asp Pro
    675                 680                 685

Arg Glu Leu Ile Glu Ile Lys Asn Lys Lys Leu Leu Ile Thr Gly
690                 695                 700

Thr Glu Gln Phe Asn Gln Lys Pro Lys Lys Gly Ile Gln Phe Leu Gln
705                 710                 715                 720

Glu Lys Gly Leu Leu Thr Ile Pro Met Asp Asn Thr Glu Val Ala Gln
            725                 730                 735
```

```
Trp Leu Arg Glu Asn Pro Arg Leu Asp Lys Lys Met Ile Gly Glu Phe
            740                 745                 750

Val Ser Asp Arg Lys Asn Ile Asp Leu Leu Glu Ser Phe Val Ser Thr
            755                 760                 765

Phe Ser Phe Gln Gly Leu Arg Leu Asp Glu Ala Leu Arg Leu Tyr Leu
    770                 775                 780

Glu Ala Phe Arg Leu Pro Gly Lys Ala Pro Val Ile His Arg Leu Leu
785                 790                 795                 800

Glu Ala Phe Thr Glu His Trp Arg Ser Cys Asn Gly Ser Pro Phe Ala
            805                 810                 815

Asn Ser Asp Ala Cys Phe Ala Leu Ala Tyr Ala Val Ile Met Leu Asn
            820                 825                 830

Thr Asp Gln His Asn His Asn Val Arg Lys Gln Asn Val Pro Met Thr
            835                 840                 845

Leu Glu Glu Phe Arg Lys Asn Leu Lys Gly Val Asn Gly Lys Asp
            850                 855                 860

Phe Glu Gln Asp Ile Leu Glu Asp Met Tyr His Ala Ile Lys Asn Glu
865                 870                 875                 880

Glu Ile Val Met Pro Glu Glu Gln Thr Gly Leu Val Arg Glu Asn Tyr
            885                 890                 895

Val Trp Ser Val Leu Leu His Arg Gly Ala Thr Pro Glu Gly Ile Phe
            900                 905                 910

Leu Arg Val Pro Pro Gly Ser Tyr Asp Leu Asp Leu Phe Thr Met Thr
            915                 920                 925

Trp Gly Pro Thr Ile Ala Ala Leu Ser Tyr Val Phe Asp Lys Ser Ile
            930                 935                 940

Glu Glu Thr Ile Ile Gln Lys Ala Ile Ser Gly Phe Arg Lys Cys Ala
945                 950                 955                 960

Met Ile Ser Ala His Tyr Gly Leu Ser Asp Val Phe Asp Asn Leu Ile
            965                 970                 975

Ile Ser Leu Cys Lys Phe Thr Ala Leu Ser Ser Glu Ser Ile Glu Asn
            980                 985                 990

Leu Pro Thr Val Phe Gly Ser Asn  Pro Lys Ala His Ile  Ala Ala Lys
            995                 1000                1005

Thr Val  Phe His Leu Ala His  Arg His Gly Asp Ile  Leu Arg Glu
    1010                1015                1020

Gly Trp  Lys Asn Ile Met Glu  Ala Val Leu Gln Leu  Phe Arg Ala
1025                1030                1035

Gln Leu  Leu Pro Gln Ala Met  Val Glu Val Glu Asp  Phe Val Asp
    1040                1045                1050

Pro Asn  Gly Lys Ile Ser Leu  Gln Arg Glu Glu Met  Pro Ser Asn
    1055                1060                1065

Arg Gly  Glu Ser Ser Val Leu  Ser Phe Val Ser Trp  Leu Thr Leu
    1070                1075                1080

Ser Gly  Pro Glu Gln Ser Ser  Val Arg Gly Pro Ser  Thr Glu Asn
    1085                1090                1095

Gln Glu  Ala Lys Arg Val Ala  Leu Asp Cys Ile Lys  Gln Cys Asp
    1100                1105                1110

Pro Glu  Lys Met Ile Thr Glu  Ser Lys Phe Leu Gln  Leu Glu Ser
    1115                1120                1125

Leu Gln  Glu Leu Met Lys Ala  Leu Val Ser Val Thr  Ala Asp Glu
    1130                1135                1140

Glu Thr  Tyr Asp Glu Glu Asp  Ala Ala Phe Cys Leu  Glu Met Leu
```

```
            1145                1150                1155

Leu Arg  Ile Val Leu Glu Asn  Arg Asp Arg Val Gly  Cys Val Trp
    1160                1165                1170

Gln Thr  Val Arg Asp His Leu  Tyr His Leu Cys Val  Gln Ala Gln
    1175                1180                1185

Asp Phe  Cys Phe Leu Val Glu  Arg Ala Val Val Gly  Leu Leu Arg
    1190                1195                1200

Leu Ala  Ile Arg Leu Leu Arg  Arg Glu Glu Ile Ser  Gly Gln Val
    1205                1210                1215

Leu Leu  Ser Leu Arg Ile Leu  Leu Leu Met Lys Pro  Ser Val Leu
    1220                1225                1230

Ser Arg  Val Ser His Gln Val  Ala Tyr Gly Leu His  Glu Leu Leu
    1235                1240                1245

Lys Thr  Asn Ala Ala Asn Ile  His Ser Gly Asp Asp  Trp Ala Thr
    1250                1255                1260

Leu Phe  Thr Leu Leu Glu Cys  Ile Gly Ser Gly Val  Lys Pro Pro
    1265                1270                1275

Asp Ala  Leu Gln Ala Thr Ala  Arg Ala Asp Ala Pro  Asp Ala Gly
    1280                1285                1290

Ala Gln  Ser Asp Ser Glu Leu  Pro Ser Tyr His Gln  Asn Asp Val
    1295                1300                1305

Ser Leu  Asp Arg Gly Tyr Thr  Ser Asp Ser Glu Val  Tyr Thr Asp
    1310                1315                1320

His Gly  Arg Pro Gly Lys Ile  His Arg Ser Ala Thr  Asp Ala Asp
    1325                1330                1335

Met Val  Asn Ser Gly Trp Leu  Val Val Gly Lys Asp  Asp Ile Asp
    1340                1345                1350

Asn Ser  Lys Ala Gly Ala Gly  Leu Ser Arg Pro Ser  Pro Ser Pro
    1355                1360                1365

Leu Val  Asn Gln Tyr Ser Leu  Thr Val Gly Leu Asp  Leu Gly Pro
    1370                1375                1380

His Asp  Thr Lys Ser Leu Leu  Lys Cys Val Glu Ser  Leu Ser Phe
    1385                1390                1395

Ile Val  Arg Asp Ala Ala His  Ile Thr Pro Asp Asn  Phe Glu Leu
    1400                1405                1410

Cys Val  Lys Thr Leu Arg Ile  Phe Val Glu Ala Ser  Leu Asn Gly
    1415                1420                1425

Gly Cys  Lys Ser Gln Asp Lys  Arg Gly Lys Ser His  Lys Tyr Asp
    1430                1435                1440

Ser Lys  Gly Asn Arg Phe Lys  Lys Pro Lys Glu Gly  Ser Val
    1445                1450                1455

Leu Arg  Arg Pro Arg Thr Ser  Ser Gln His Gly Thr  Arg Gly Gly
    1460                1465                1470

His Ser  Asp Glu Glu Glu Asp  Glu Gly Val Pro Ala  Ser Tyr His
    1475                1480                1485

Thr Val  Ser Leu Gln Val Ser  Gln Asp Leu Leu Asp  Leu Met His
```

-continued

```
                    1490                1495                1500

Thr Leu His Thr Arg Ala Ala Ser Ile Tyr Ser Ser Trp Ala Glu
    1505                1510                1515

Glu Gln Arg His Leu Glu Ser Gly Gly Arg Lys Ile Glu Ala Asp
    1520                1525                1530

Ser Arg Thr Leu Trp Ala His Cys Trp Cys Pro Leu Leu Gln Gly
    1535                1540                1545

Ile Ala Cys Leu Cys Cys Asp Ala Arg Arg Gln Val Arg Met Gln
    1550                1555                1560

Ala Leu Thr Tyr Leu Gln Arg Ala Leu Leu Val His Asp Leu Gln
    1565                1570                1575

Lys Leu Asp Ala Leu Glu Trp Glu Ser Cys Phe Asn Lys Val Leu
    1580                1585                1590

Phe Pro Leu Leu Thr Lys Leu Leu Glu Asn Ile Ser Pro Ala Asp
    1595                1600                1605

Val Gly Gly Met Glu Glu Thr Arg Met Arg Ala Ser Thr Leu Leu
    1610                1615                1620

Ser Lys Val Phe Leu Gln His Leu Ser Pro Leu Leu Ser Leu Ser
    1625                1630                1635

Thr Phe Ala Ala Leu Trp Leu Thr Ile Leu Asp Phe Met Asp Lys
    1640                1645                1650

Tyr Met His Ala Gly Ser Ser Asp Leu Leu Ser Glu Ala Ile Pro
    1655                1660                1665

Glu Ser Leu Lys Asn Met Leu Leu Val Met Asp Thr Ala Glu Ile
    1670                1675                1680

Phe His Ser Ala Asp Ala Arg Gly Gly Ser Pro Ser Ala Leu Trp
    1685                1690                1695

Glu Ile Thr Trp Glu Arg Ile Asp Cys Phe Leu Pro His Leu Arg
    1700                1705                1710

Asp Glu Leu Phe Lys Gln Thr Val Ile Gln Asp Pro Met Pro Thr
    1715                1720                1725

Glu Pro His Ser Gln Asn Ala Leu Ala Ser Thr His Leu Thr Pro
    1730                1735                1740

Ala Ala Gly Asp Pro Gly His Leu Pro Ser Pro Glu Ile Pro Ser
    1745                1750                1755

Glu Val Gly Ala Cys Asp Ser Glu Lys Pro Glu Gly Thr Arg Ala
    1760                1765                1770

Thr Ser Ser Ser Ser Pro Gly Ser Pro Val Ala Ser Ser Pro Ser
    1775                1780                1785

Arg Leu Ser Pro Ser Pro Glu Gly Pro Pro Leu Ala Gln Pro
    1790                1795                1800

Pro Leu Ile Leu Gln Pro Leu Thr Ser Pro Leu Gln Val Gly Val
    1805                1810                1815

Pro Pro Met Ala Leu Pro Ile Ile Leu Asn Pro Ala Leu Ile Glu
    1820                1825                1830

Ala Thr Ser Pro Val Pro Leu Leu Ser Thr Pro Arg Pro Thr Asp
    1835                1840                1845

Pro Ile Pro Thr Ser Glu Val Asn
    1850                1855
```

SMALL MOLECULE INHIBITION OF INTRACELLULAR TRANSPORT

CROSS REFERENCE TO A RELATED APPLICATION

This application claims priority from U.S. Provisional Application Ser. No. 61/140,400 filed on Dec. 23, 2008, which is hereby incorporated by reference in its entirety.

GOVERNMENTAL RIGHTS

This invention was made in part with government support under grant 54 AI057160 awarded by the National Institutes of Health. The government has certain rights in the invention.

REFERENCE TO SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821(f).

FIELD OF INVENTION

The present disclosure relates generally to the activity of intracellular transport proteins and in particular to compositions and methods useful in inhibiting such proteins for research and therapeutic purposes.

BACKGROUND OF THE INVENTION

The Golgi complex controls trafficking of proteins, including their transport, processing and packaging, and plays an especially important role in the processing of proteins destined for secretion. Arf proteins (ADP-ribosylation factor proteins) are members of the Ras superfamily of small guanosine triphosphatases (GTPases) and mediate vesicular transport in the cellular secretory and endocytic pathways. Arf1 is a Golgi-localized protein present in all higher eukaryotic cells and regulates both anterograde and retrograde traffic. Like other Ras GTPases, Arf1 cycles between its cytosolic GDP-bound form and its membrane-associated GTP-bound form. In its GTP-bound state, Arf1 recruits adaptor and vesicle coat proteins to initiate the formation and release of transport vesicles.

Brefeldin (BFA) is a metabolite of the fungus *Eupenicillium brefeldianum* that specifically and reversibly blocks protein transport from the endoplasmic reticulum (ER) to the Golgi apparatus in certain eukaryotic cell types, and has become an important tool in cell biology research. BFA has been used successfully to investigate the activity of Arf1, for example to demonstrate Arf1 activation by guanine nucleotide exchange factors (GEFs), which exchange GDP for GTP.

The function of individual ArfGEFs has also been the subject of recent investigations. The ArfGEFS are divided into two families consisting of the large BFA-susceptible molecules, which localize to the Golgi and trans-golgi network (TGN), and the smaller BFA-resistant ARNO-family GEFs, which predominantly localize to endosomes. In mammalian cells, GBF1 (Golgi BFA resistance factor 1) is a large BFA-susceptible ArfGEF. More specifically, GBF1 is a cis-Golgi-localized ArfGEF that assists in the recruitment of coat protein COPI 4-6. Following activation by GBF1, Arf1 mediates the COPI coat recruitment that enables vesicle transport between the Golgi and endoplasmic reticulum (ER). The proteins BIG1 and BIG2 are also large BFA-susceptible ArfGEFs, functionally similar, that facilitate recruitment of clathrin coat protein. Arf1 activation by BIG1 and BIG2 results in Arf1 recruitment of adaptor proteins (AP-1, AP-3, and AP-4). These adaptor proteins mediate transport between endosomes and either the TGN or lysosomes, and also mediate recruitment of certain Arf-binding proteins (GGA 1-3) that are involved in trafficking from the TGN and within the endosomal compartment.

Among the ArfGEFs, GBF1 has been studied most intensively, either by siRNA-mediated silencing (see, e.g., Citterio et al., 2008) or by the expression of dominant-negative forms (see, e.g., Holloway et al., 2007). However, results from these perturbations have not produced complete agreement about the phenotypic and functional characteristics of GBF1. While the results do indicate that GBF1 plays an important role in intra-Golgi transport, nevertheless, understanding of GBF1 function remains limited, as does the availability of tools for isolating the specific activity and function of GBF1 and other ArfGEF's, particularly with respect to distinguishing among them.

SUMMARY OF INVENTION

In one aspect, the present disclosure provides a method of inhibiting Golgi BFA resistance factor (GBF1) in a eukaryotic cell, the method comprising contacting the cell with Golgicide A. Contacting the cell with Golgicide A may comprise contacting the cell with a solution of Golgicide A in an organic solvent, such as for example DMSO. The solution of Golgicide A may comprise Golgicide A at a concentration of from about 0.1 µM to about 100 µM, or from about 5 µM to about 20 µM. The eukaryotic cell may be a mammalian cell, and may be more particularly a human cell. In one embodiment, the method may further comprise exposing the cell to a cytotoxin selected from the group consisting of: shiga toxin, cholera toxin, heat labile toxin, heat stable toxin, abrin, and ricin. The method may further comprise at least partially reversing the effect of Golgicide A on GBF1 by wash-out of Golgicide A with a cell medium lacking Golgicide A.

In another aspect, the present disclosure provides a kit for characterizing GBF1 function comprising: an isolated nucleic acid encoding a mutant GCA-resistant GBF1; an amount of Golgicide A; and instructions for measuring at least one of: synthesis of a protein, secretion of a protein and transport of a protein. In the kit, the nucleic acid encoding a GCA-resistant GBF1 may comprise SEQ. ID. NO: 10 or a conservative variant thereof. The protein is for example a soluble protein. The protein may be a membrane-bound protein. The kit may further comprise an amount of a medium lacking Golgicide A and instructions for at least partially reversing Golgicide A activity in the cell by wash-out with the medium lacking Golgicide A. The kit may further comprise an amount of a cytotoxin, which may be selected from the group consisting of: shiga toxin, cholera toxin, heat labile toxin, heat stable toxin, abrin, and ricin. The kit may further comprise a transfection agent.

In another aspect, the present disclosure provides an isolated mutant GBF1 gene lacking sensitivity to GCA comprising GBF1-M832L (SEQ ID NO: 10) or a conservative variant thereof. Also disclosed is an expression construct that comprises an isolated mutant GBF1 gene lacking sensitivity to GCA or a conservative variant thereof. Also disclosed is a host cell comprising such an expression construct. Also disclosed is a vector comprising a gene of interest and a mutant GBF1 gene lacking sensitivity to Golgicide A, and a method of using same in a method of selecting cells expressing a gene of interest, the method comprising: exposing a population of cells to the vector, so that at least a cell in the population of cells is co-transfected with the gene of interest and a mutant GBF1 gene; and exposing the population of cells to Golgicide A so that at least a portion of non-transfected cells are destroyed.

BRIEF DESCRIPTION OF THE FIGURES

FIG. 4 is a series of photomicrographs showing that BFA and GCA disperse the medial-Golgi marker giantin to a partially punctate pattern adjacent to ERES.

FIG. 5 is a series of photomicrographs showing that BFA and GCA have distinct effects on the TGN and endosomes.

FIGS. 6A and B are a series of photomicrographs showing that GCA does not affect microtubular or actin cytoskeletons.

FIGS. 7A and B are a series of photomicrographs showing that GCA does not affect transport through recycling endosomes.

FIG. 13 is a series of photomicrographs showing that transduction with GBF1-ML is less than 100% efficient.

FIG. 16 is a series of photomicrographs showing that expression of GBF1-ML or GBF1-loop mutants results in resistance of the effects of GCA on is VSVG-GFP transport.

FIG. 17 is a series of photomicrographs showing that expression of GBF1-ML but not GBF1-loop mutants results in resistance to the effects of BFA on Golgi morphology.

FIG. 18 is a series of photomicrographs showing that expression of GBF1-ML but not GBF1-loop mutants results in resistance to the effects of BFA on Golgi morphology. Vero cells were transiently transfected with GBF1-WT, or a GBF1-R843A, GBF1-K844A, GBF1-Q845A, or GBF1-N846A. Thirty-six hours later the cells were treated for 60 mins with GCA (10 mM) then fixed and labeled with anti-HA epitope (GBF1; red) or giantin (green). Cells expressing GBF1-R843A, GBF1-Q845A, and GBF1-N846A are resistant to the effects of GCA on Golgi morphology, whereas cells expressing GBF1-WT and GBF1-K844A are only partially protected. White asterix mark the partially protected cells.

FIG

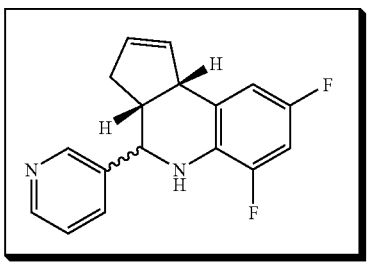

Formula (I)

Figure 1:
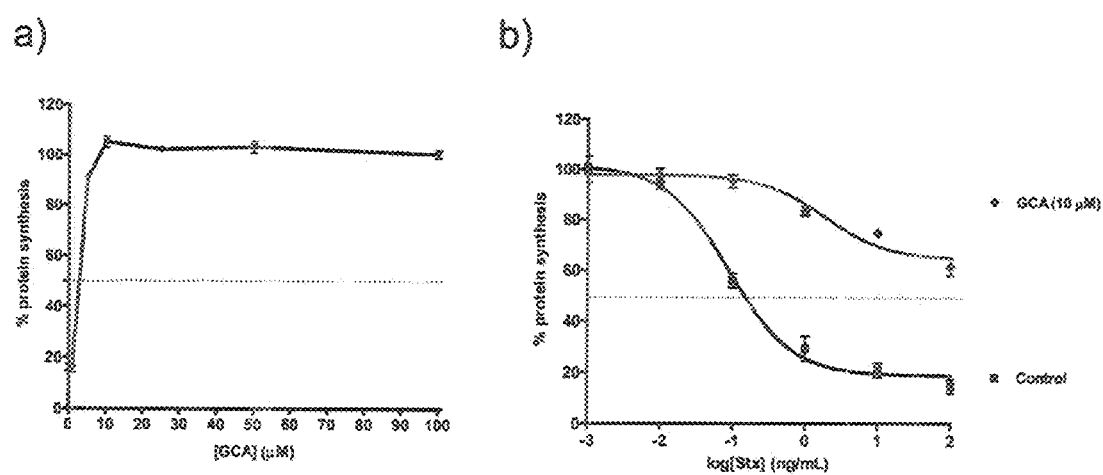
FIG. 1 shows graphs of the effects of Golgicide A (GCA) on Vero cells treated with shiga toxin.

Analysis of the compound of Formula (I) as obtained from ChemDiv by reverse-phase LC-MS revealed the compound to be present as a 10:1 diastereomeric mixture. The compound was resynthesized which also resulted in a 10:1 diastereomeric mixture. The resultant mixture was then determined to be identical to that obtained as part of a screening library from ChemDiv using $^1$H NMR and LC-MS ($^1$H NMR 600 MHz (CDCl$_3$) δ 8.78 (d, J=1.5 Hz, 1H), 8.62 (dd, J=1.2, 3.8 Hz, 1H), 8.03 (d, J=7.9 Hz, 1H), 7.52 (m, 1H), 6.63 (m, 2H), 5.83 (m, 1H), 5.69 (m, 1H), 4.70 (d, J=2.9 Hz, 1H), 4.10 (d, J=8.5 Hz, 1H), 3.95 (s, 1H), 3.00 (m, 1H), 2.59 (m, 1H), 1.82 (m, 1H); $^{13}$C NMR 150 MHz (CDCl$_3$) δ 147.7, 147.2, 138.7, 135.8, 133.0, 132.2, 131.1, 124.3, 110.4, 110.3, 101.3, 101.2, 101.1, 55.6, 46.2, 45.6, 31.3; MS m/z 285.19 (M+1)). Purification of the major isomer was achieved by recrystallization from acetonitrile and water. The biological activity of this purified major isomer is identical to the material obtained in the screening library as a DMSO solution.

Briefly, GCA was found to specifically and reversibly inhibit GBF1 function in eukaryotic cells. The result is rapid dissociation of COPI from Golgi membranes and subsequent disassembly of the Golgi and trans-Golgi network (TGN). Thus, GCA exposure arrests secretion of both soluble and membrane-associated proteins at the Endoplasmic Reticulum-Golgi Intermediate Compartment (ERGIC). However, GCA-induced GBF1 inhibition does not affect endocytosis and recycling of transferrin. In addition, GCA arrests certain internalized cytotoxins within the endocytic compartment, and the arrested cytotoxin is unable to reach the dispersed TGN. Because of its surprisingly specific and reversible effects on GBF1 and consequently on protein transport and trafficking, Golgicide A is a potent agent for manipulating GBF1 activity for research and therapeutic purposes.

In accordance with the present invention, conventional molecular biology, microbiology, and recombinant DNA techniques as well known and within the skill of the art are employed. Such techniques are well explained and familiar to those in the art. Applicable and helpful resources regarding routine procedures include, e.g., Sambrook, Fritsch & Maniatis, MOLECULAR CLONING: A LABORATORY MANUAL, SECOND EDITION (1989), Cold Spring Harbor Laboratory Press, Cold Spring Harbor, N.Y. (herein "Sambrook et al., 1989"); and F. M. Ausubel et al. (eds.), CURRENT PROTOCOLS IN MOLECULAR BIOLOGY, John Wiley & Sons, Inc. (1994).

DEFINITIONS

As used herein the term "GBF1" refers to human Golgi-specific BFA resistance factor protein, a cis-Golgi-localized guanine nucleotide exchange factor having the amino acid sequence (SEQ ID NO: 1) published in Mansour, S. J., Herbrick, J. A., Scherer, S. W. and Melancon, P. (1998) *Human GBF1 is a ubiquitously expressed gene of the sec7 domain family mapping to 10q24. Genomics* 54 (2), 323-327 (1998), (GenBank Accession No.: # NM_004184.1), and conservative variants thereof.

The term "GBF1 gene" refers to the genomic nucleic acid sequence (SEQ ID NO: 2) that encodes the human Golgi-specific BFA resistance factor protein of SEQ ID NO: 1, specifically, the gene sequence available from GenBank under accession number 004193.1, and to allelic variants thereof. The nucleotide sequence of the gene, as used herein, encompasses both coding regions, referred to as exons, and intervening, non-coding regions, referred to as introns.

As used herein, the phrase "shiga toxin" encompasses the toxin produced by the bacterium *Shigella dysenteriae*, and the shiga-like toxin, an ABS-type shiga toxin produced by the bacterium *Escherichia coli*, sometimes referred to as verotoxin, and toxic subunits and variants thereof.

As used herein, the phrase "cholera toxin" encompasses the enterotoxin produced by the bacterium *Vibrio cholerae*, and toxic subunits and variants thereof.

As used herein, the phrase "heat labile toxin" encompasses the temperature sensitive enterotoxin produced by the bacterium *Escherichia coli*, and toxic subunits and variants thereof.

As used herein, the phrase "heat stable toxin" encompasses the temperature insensitive enterotoxin produced by the bacterium *Escherichia coli*, and toxic subunits and variants thereof.

As used herein, the term "abrin" encompasses the toxic lectins from *Abrus precatorius* and toxic subunits and variants thereof.

As used herein, the term "ricin" encompasses the lectin RCA60 from *Ricinus communis* (castor bean) and toxic subunits and variants thereof.

"Conservative variant": conservative variants of nucleotide sequences include nucleotide substitutions that do not result in changes in the amino acid sequence, as well as nucleotide substitutions that result in conservative amino acid substitutions, or amino acid substitutions which do not substantially affect the character of the polypeptide translated from said nucleotides. For example, GBF1 polypeptide character is not substantially affected if the nucleotide substitutions in a nucleotide sequence variant of GBF1 translate to a polypeptide sequence that does not preclude specific inhibition by GCA. The polypeptide character of a GBF1 mutant polypeptide lacking sensitivity to GCA is not substantially affected if the sensitivity of the mutant is not substantially increased by a nucleotide substitution or substitutions, in addition to a nucleotide substitution associated with the decreased sensitivity to GCA of the GBF1 mutant polypeptide, in the nucleotide sequence encoding the GBF1 mutant. Correspondingly, conservative variants of polypeptides have an amino acid sequence that differs from a polypeptide sequence by one or more conservative amino acid substitutions and/or modifications which do not substantially affect the character of the polypeptide. For example, conservative variants of a GBF1 polypeptide include those for which the specific inhibition by GCA is not substantially diminished. In the case of a GBF1 mutant polypeptide lacking sensitivity to GCA, conservative variants include those for which the specific inhibition by GCA is not substantially increased. Preferably, a conservative polypeptide variant contains substitutions and/or modifications at no more than about 20% of the amino acid residues, and more preferably at no more than about 10% of residues. Such substitutions, which are preferably conservative, may be made in noncritical and/or critical regions of the native protein. Variants may also, or alternatively, contain other modifications, including the deletion or addition of amino acids that have minimal influence on the activity of the polypeptide. In particular, variants may contain additional amino acid sequences at the amino and/or carboxy temini. Such sequences may be used, for example, to facilitate purification or detection of the polypeptide.

I. Methods Using GCA

In one aspect the methods encompass a method of inhibiting GBF1 in a eukaryotic cell, the method comprising contacting the cell with GCA. GCA can be prepared as a stock solution by dissolving the commercially obtained GCA in white crystalline powder form in an organic solvent such as ethanol, methanol or dimethyl sulfoxide (DMSO). An exemplary GCA solution is prepared in DMSO at a concentration of about 0.1 µM to about 100 µM of GCA, preferably from about 5 µM to about 20 µM, and in an exemplary embodiment about 10 µM.

The eukaryotic cell can be for example any eukaryotic cell, especially a mammalian cell such as a dog, monkey, mouse, rat or human cell, and may be a stem cell or a cell from an immortalized cell line such as a HeLa cell line. Exemplary cells are those from commonly used cell lines including HeLa cells, Vero cells (African green monkey kidney, CRL-1587), MDCK (Madin-Darby canine kidney, CCL-34), and 293A-HEK (Human embryonic kidney, CRL-1573) cells, all of which can be obtained from the American Type Tissue Culture Collection (ATCC) of Manassas, Va. Cells are typically maintained in vitro in a bath of appropriate cell or tissue culture medium according to ATCC recommendations and also as well known in the art. The cell is contacted with GCA typically by simply adding the GCA solution to the cell medium bathing the cell in vitro, or by exchanging a GCA-free cell or tissue medium with a GCA-containing cell or tissue medium.

Through its effect on the Golgi and TGN, exposure of the cell to GCA inhibits the effect of certain cytotoxins to which the cell is also exposed. For example, GCA exposure inhibits the effects of shiga toxin and cholera toxin and any other toxin or subunit thereof that depends upon the integrity of the Golgi and TGN to produce a cytotoxic effect. Other such toxins include *E. coli* heat labile toxin, *E. coli* heat stable toxin, abrin, and ricin. Exposure of the cell to a cytotoxin in vitro can be achieved by any of various methods known in the art. For example, shiga toxin and cholera toxin and toxic subunits thereof are commercially available and can be dissolved in commonly used cell or tissue media. The *E. coli* enterotoxins, heat labile toxin and hest stable toxin, and toxic subunits thereof are commercially available in lyophilized powder form from Sigma Aldrich Corporation of St. Louis, Mo. Abrin is a naturally occurring poison found in the seeds of the rosary pea (also known as the jequirity pea), and is similar to ricin, a toxin found in the seeds of the castor bean plant. Abrin and ricin can be prepared in the form of a powder, a mist, or a pellet, and can also be dissolved in water. In one aspect the invention provides a method of inhibiting effects of a cytotoxin on a eukaryotic cell, in which the cell is contacted by GCA and also exposed to the cytotoxin. Exposure of the cell to the toxin may be simultaneous with exposure to GCA, or may occur after exposure to GCA.

The effect of GCA on GBF1 is reversible. After a cell has been exposed to GCA, the GCA can be washed out using for example a cell or tissue medium lacking any GCA. Wash-out is performed by changing a GCA-containing bathing solution, such as a GCA-containing tissue or cell culture medium, at least once or several times with a GCA-free medium, or by circulating GCA-free medium through a cell or issue perfusion system that is perfusing the cell. Following washout, effects of GCA on the cell are reduced or eliminated. Specifically, removal of GCA is followed by reassembly of the Golgi and TGN.

In another aspect, the invention provides a method for characterizing GBF1 function including providing a eukaryotic cell with DNA encoding a GCA-resistant form of GBF, exposing the cell to GCA, and subsequently measuring certain events relating to expression and activity of one or more proteins that are of interest. For example, it is useful to compare protein synthesis, protein secretion, and protein transport of selected protein(s) in cells with intact GBF1 and cells lacking GBF1 activity caused by exposure to GCA. Moreover, in characterizing the effect of GBF1 on cell function, distinctions can be made with respect to GBF1 function as it impacts soluble proteins and membrane-bound proteins. That the effect of GCA can be reversed by simple washout is an advantage in terms of designing an experimental protocol that compares observations of protein activity before and after GCA exposure. For example, the reversibility of GCA makes it well suited for experiments designed to quantify specific effects of GCA on the cell, such as on cellular protein activity that may or may not be impacted by interference with the Golgi network. After an initial exposure of a cell to GCA, a first measurement of protein activity is taken at a first point in time. The protein activity is for example protein synthesis, protein secretion or protein transport. GCA is then at least partially reversed by washout of the GCA using a cell or tissue medium lacking GCA. After washout of the GCA, a second measurement of the protein activity is taken at a second point in time, and the first and second measurements are compared. A difference in the two measurements is determined. Similar measurements made under control conditions can be performed to help identify any specific effect of GCA on the protein activity under examination. In an exemplary embodiment, the cell is also exposed to a cytotoxin that involves the Golgi and TGN.

A mutant GBF1 gene lacking sensitivity to GCA can be prepared using site-directed mutagenesis. A GBF1 cDNA such as a hamster or human GBF1 cDNA is used as a template for constructing HA-tagged wild type and mutant cDNA. For example, GBF1-HA can be generated by PCR using appropriate primers, such as GBF1-HA (5'-GCCGCGCTAGCCT-GAGGCAT AGTCAGGCACGTCATAAGGATAGCCGT-TGACTTCAGAGGTGGGAATAGGGTCTGTAG-3'; (SEQ ID NO: 3)) and the upstream GBF1 primer (5'-GACAG-GTTTGCCAAGATGGTGGATAAGAATATT TACATC-3'; (SEQ ID NO: 4)). The resulting PCR product can be cloned into a suitable vector such as pcDNA3.1D/V5-His-TOPO (Invitrogen) under control of an appropriate promoter such as the cytomegalovirus (CMV) promoter. GBF1-ML and GBF1-EK mutants can be generated using mutagenic primers and a commercially available mutagenesis kit according to the manufacturer's instructions, such as the QuikChange II XL Site-Directed Mutagenesis Kit available from Stratagene. An exemplary sense primer for GBF1-E794K is (5'-GCCT-TCCGTTTGCCCGGGAAGGCACCAGTTAT-TCACAGGTTGC-3'; (SEQ ID NO: 5)), and an exemplary antisense primer for GBF1-E794K is (5'-GCAACCTGT-GAATAACTGGTGCCTTCCCGG GCAAACGGAAGGC-3'; (SEQ ID NO: 6). An exemplary sense primer for GBF1-M832L is (5'-GGCCTATGCTGTCATCTTGC TAATACTGACCAGC-3'; (SEQ ID NO: 7)), and an exemplary antisense GBF1-M832L primer is (5'-GCTGGTCAG-TATTAAGCAAGATGACAGCATAGGCC-3'; (SEQ ID NO: 8)).

To prepare an adenovirus that can express a mutant GBF1 gene, the appropriate cDNA is cloned into a plasmid such as pENTR-11, and then the cDNA insert is transferred to plasmid pAD/CMV/DEST using the Clonase II reaction (all from Invitrogen). Crude adenoviral stocks can be generated and isolated from transfected host cells such as 293A cells, which are then used to generate high titer stocks that can be aliquoted and frozen until needed or transduction.

Methods for achieving transient transfection of a cell in vitro with a selected heterologous gene such as a mutant GBF1 lacking sensitivity to GCA are well known. Such methods include use of a viral vector or of any commonly known transfection reagents according to manufacturer's instructions. Non-viral transfection methods typically exploit normal cellular mechanisms in eukaryotic cells including mammalian cells for the uptake and intracellular transport of macromolecules. Exemplary such non-viral transfection methods rely on endocytic pathways for the uptake of the expression constructs by the targeted cell. Exemplary methods thus typically involve use of liposomal derived systems, poly-lysine conjugates, or artificial viral envelopes. Non-limiting examples of suitable transfection reagents include Lipofectamine 2000 available from Invitrogen Corporation, TransFectin available from Bio-Rad Laboratories, TransIT-LT1 available from Mirus Bio, GeneJuice available from Novagen, and Effectene available from Qiagen. It will be recognized that different transfection reagents are optimized for gene or nucleotide delivery to particular cell lines. Given a particular cell line, manufacturer's instructions and guidance for selection of a transfection reagent should be consulted. Cells targeted for transfection are maintained and typically incubated with the selected transfection reagent and gene or nucleotide sequence in a suitable cell tissue medium according to manufacturer's recommendations. For analysis after sufficient incubation time, cells are collected and disposed on slides such as chamber slides.

A radioactive amino acid incorporation assay is used to assess GCA's ability to inhibit a particular cytotoxin. Similar methods have previously been described to identify inhibitors of shiga toxin trafficking (see Saenz et al., 2007 and Zhao and Haslam, 2005). Confirmation of a GCA effect is assessed using a previously described radioactive [35S] incorporation assay adapted to a multi-well format (see Saenz et al., 2007). Briefly, cells such as Vero cells are cultured overnight under appropriate conditions (e.g. 37° C. and 5% CO2) in multi-well plates and treated with a GCA-containing solution or a medium with GCA at a desired concentration. Following a suitable incubation period of about 0.5 to about 3 hours at 37° C., or longer at a lower temperature, the selected toxin is added to wells, and cells are shifted to 37° C. for an additional incubation period of, for example, about 1 to about 4 hours. Medium containing trans [35S] label at 10 mCi/ml is added, and cells are incubated at 37° C. for an additional period of about 45 min, washed with a suitable buffer solution at a pH of about 7.4, and lysed by exposure for sufficient period of time (typically about 1 to about 24 hours) to a suitable lysing solution. Proteins from the lysed cells are TCA-precipitated to a final concentration of 15%, transferred to multi-screen HA plates, and the filters are washed with ice-cold 20% TCA. Filters are then removed from the plate, placed in a scintillation fluid and [35S] incorporation quantitated using a beta counter (Beckman).

Immunofluorescence is used to track GCA effects on specific cellular proteins involved in intracellular transport and trafficking. After exposure in vitro to GCA, cells are fixed in a fixative solution such as, for example, 4% paraformaldehyde in cold PBS. Cells are then permeabilized with a detergent solution such as 0.1% Triton X-100 in PBS, blocked, and probed with fluorescently labeled antibodies diluted in blocking buffer. Cells are typically rinsed in an appropriate buffer solution such as PBS prior to mounting in an anti-fade mounting agent such as SlowFade Gold. The mounting reagent may also contain a DNA (nuclear) stain such as DAPI or a Hoechst stain. Fluorescence imaging is performed for example using epifluorescence (Zeiss) microscopy.

Toxin and transferrin internalization after GCA exposure (or for comparative purposes after exposure to a control solution or a solution containing another agent such as BFA) can be tracked using immunofluorescence. For example, cells such as Vero cells are grown in chamber slides, treated with serum-free medium containing a control solution (e.g. DMSO), BFA or GCA at selected concentrations and for varying periods of time at 37° C. Following the binding of toxin and transferrin at 4° C., cells are shifted to 19° C. conditions for at least about one hour to allow for toxin internalization. Cells are then processed for immunofluorescence as described elsewhere herein.

II. Nucleotides, Expression Constructs and Vectors Including a Mutant GBF1 Gene (a) Constructs and Vectors In another aspect, the present disclosure provides an isolated mutant GBF1 gene lacking sensitivity to GCA. The mutant gene is a mammalian GBF1 gene such as the hamster GBF1 gene with an M for L substitution at the residue corresponding to residue 832 in the human GBF1 sequence (which, in the hamster sequence is residue 830). For example, to prepare the mutagenized form of the gene, a wild-type GBF1 cDNA such as hamster GBF1 cDNA (SEQ ID NO: 9; obtained from Paul Melançon, University of Alberta, Edmonton, AB; see published sequence in Claude A et al. (1999) GBF1*: A novel Golgi-associated BFA-resistant guanine nucleotide exchange factor that displays specificity for ADP-ribosylation factor* 5. J. Cell Biol 146(1): 71-84; GenBank Accession No. AF127523) is used as a template and mutants are generated using a commercial mutagenesis kit such as QuikChange II XL Site-Directed Mutagenesis Kit (Stratagene). The ML mutation described herein corresponds to residue 830 of SEQ ID NO. 9 because that sequence is from the hamster, which differs from the human GBF1 sequence by deletion of two bases. When referring to the ML mutation herein the convention is M832L because position 832 corresponds to the appropriate M in human GBF1. Similarly, other point mutations described herein (e.g. E794K) are designated with reference to the human GBF1. Mutagenic primers for the M832L mutation are M832L sense (5'-GGCCTATGCTGTCATCTTGCTTAATACTGACCAGC-3'; (SEQ ID NO: 7)), and M832L antisense (5'-GCTGGTCAGTATTAAGCAAGATGACAGCATAGGCC-3'; (SEQ ID NO: 8). Mutant clones are typically sequenced to ensure their fidelity.

An expression construct can be made that includes a mutant GBF1 gene lacking sensitivity to Golgicide A, and may also include another gene or nucleotide of interest. The construct is then used to transfect cells to produce the mutant protein. For example, adenovirus expressing GBF1-HA constructs, canine Arf1 switch mutants, and NPY-GFP can be prepared by using readily commercially available plasmids and cloning enzymes. For example, the appropriate cDNA can be cloned into a plasmid such as pENTR-11 (Invitrogen) then the cDNA insert transferred to a plasmid such as pAD/CMV/DEST (Invitrogen) using the Clonase II reaction (Invitrogen). The gene or nucleotide of interest can be any gene or nucleotide, such as for example a nucleotide sequence encoding an affinity or purification tag such as a histidine tag or other marker protein. A vector including a mutant GBF1 gene lacking sensitivity to Golgicide A such as GBF1-M832L can be prepared using conventional molecular biology, microbiology, and recombinant DNA techniques well known in the art and explained in the literature.

(b) Methods Using Constructs and Vectors

The mutant GBF1 gene and vectors containing a mutant GBF1 gene lacking sensitivity to Golgicide A provide the basis of certain methods. For example, a vector containing the mutant GBF1 gene can be used in a method of selecting cells expressing a gene or nucleotide of interest. A population of eukaryotic cells is exposed to a vector containing both the gene or nucleotide of interest and the mutant GBF1 gene lacking sensitivity to Golgicide A so that at least a cell in the population of cells is co-transfected with both the gene or nucleotide of interest and the mutant GBF1 gene. The population of cells is then exposed to Golgicide A so that non-transfected cells are destroyed, leaving only those cells in the population that have been transfected with the gene or nucleotide of interest and are also GCA-resistant by virtue of being co-transfected with the mutant GBF1, GCA-resistant gene.

The mutant GBF1 gene can also provide the basis of a gene therapy for treating cancers including leukemia or lymphoma in a subject in need thereof. The method takes advantage of GCA effects in combination with GCA resistance conferred by a mutant GBF1 gene. Generally, gene therapy methods rely on creating a genomic modification involving the introduction of specific DNA to an organism in such a manner that the introduced DNA integrates into the chromosomal DNA. Typically, retroviral vectors have been shown to provide the most efficient integration of the introduced DNA. Alternatively, other methods can be used to integrate DNA into a cell, including the use of adeno-associated virus (AAV) as a vector, calcium phosphate co-precipitation, electroporation, lipofection, microinjection, protoplast fusion, particle bombardment, and the use of site-specific recombinases such as Cre (Sternberg and Hamilton, J Mol Biol 150:467-486, 1981), Flp (Broach, et al, cell-29:227-234, 1982) and R (Matsuzaki, et al, J Bacteriology 172:610-618, 1990).

For example, to treat a subject suffering from a leukemia or lymphoma, a population of bone marrow cells is extracted from the subject and isolated. Non-cancerous bone marrow cells are identified and isolated using selection methods as known in the art. The non-cancerous bone marrow cells are transfected with the mutant GBF1 gene lacking sensitivity to GCA. Cancerous cells can be selectively destroyed by exposure to GCA following transfection of non-cancerous bone marrow cells with a mutant GBF1 gene lacking sensitivity to GCA. Thus, the method includes isolating a population of bone marrow cells from the subject, selecting non-cancerous cells from the population of bone marrow cells, transfecting the non-cancerous bone marrow cells with a mutant gene lacking sensitivity to Golgicide A, re-infusing the non-cancerous cells into the subject and administering an amount of Golgicide A to the subject so that non-transfected cells including cancerous cells are destroyed.

II. Kits

GCA and nucleic acid constructs according to the present disclosure also provide the basis for a kit useful for investigating mechanisms underlying assembly and transport in the Golgi in a eukaryotic cell, and in particular for characterizing GBF1 function. The kit may comprise for example an isolated nucleic acid encoding a mutant GCA-resistant GBF1; an amount of Golgicide A; and instructions for measuring at least one of: synthesis of a protein, secretion of a protein and transport of a protein in the cell. In an exemplary embodiment, the nucleic acid encoding a GCA-resistant GBF1 comprises SEQ. ID. NO: 10 or a conservative variant thereof, or complementary thereto, by which it will be understood that the nucleic acid may comprise DNA or RNA. The amount of GCA can be provided in a suitable solvent or medium, together with one or more additional reagents useful in applying GCA as a tool for in vitro investigations of Golgi transport. Such reagents include for example an amount of any one or more of the toxins mentioned herein, including shiga toxin, cholera toxin, heat labile toxin, heat stable toxin, abrin, and ricin, or a combination thereof. The kit may further comprise an amount of a GCA-fee medium for wash-out of the GCA. The kit may further include instructions for determining the effect of GCA on protein transport in a cell, or on the Golgi, according to methods described elsewhere herein. The kit may comprise a transfection reagent for transfecting cells with a mutant GBF1 gene lacking sensitivity to GCA. The kit may further include any detection material or device such as a labeling system, a cocktail of components such as solutions or suspensions required for any type of PCR, and especially real-time quantitative RT-PCR. The one or more reagents may comprise one or more other hybridization or amplification reagents, including for example a DNA polymerase and appropriate buffer solutions. Test kits according to the present disclosure preferably include instructions for carrying out one or more of the presently disclosed methods, including contacting the cell with GCA and washing GCA out. Instructions included in kits of the present disclosure can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

The present disclosure identifies and characterizes GCA as a potent, specific highly effective, and rapidly reversible inhibitor of intra-Golgi transport. The phenotypic effects of GCA treatment are markedly similar to those induced by expression of dominant-inactive GBF1. Canine cells are resistant to the effects of GCA, and characterization of the canine GBF1 gene reveals a methionine for leucine substitution at residue 832, which when introduced into the hamster GBF1, results in complete resistance to the phenotypic and functional effects of GCA. This residue is located in the Sec7 domain within an alpha-helix that associates with Arf1 in its GDP-bound state which together form a hydrophobic interfacial cleft. BFA binds within this pocket, interacting with residues both from the GBF1 Sec7 domain and from Arf1. Resistance of GBF1-M832L to GCA indicates that GCA also binds within the hydrophobic pocket and interacts with the same methionine residue. However, an important difference between GCA and BFA, which inhibits BIG1 and BIG2 in addition to GBF1, is that GCA is highly specific for GBF1. Notably, within the BFA-binding region, considerable amino acid sequence divergence exists between GBF1 and BIG1/BIG2. Without wishing to be bound by theory, molecular modeling and mutagensis studies reveal that a tripeptide loop within the GBF1 Sec 7 domain, which is lacking in all other known Arf1 GEF's, accounts for the selectivity of GCA for its target.

GCA inhibits Arf1 function, and this effect is largely rescued by the expression of GBF1-M832L, indicating that GCA directly inhibits GBF1 function. Knowing that GBF1 is the target of GCA, GCA can be used, for example as described herein, to investigate the role of GBF1 in anterograde and retrograde transport through the Golgi. Exposure of cells to GCA shows that transport of tsVSVG-GFP is arrested in the ER-Golgi intermediate compartment which indicates that GBF1 function is not required for exit of cargo from the ER, but is required for transport past the ERGIC. These results are consistent with the results obtained with expression of a dominant-negative GBF1 and by siRNA-mediated inhibition of GBF1 expression. (R. Garcia-Mata et al., 2003).

Inhibition of GBF1 function with GCA also blocks secretion of soluble cargo. These results surprisingly differ from a recent report that inhibited GBF1 expression by siRNA and found no effect on the secretion of soluble cargo, though transport of transmembrane proteins was impaired. (T. Szul et al., 2007). Golgi morphology in these cells was relatively mildly affected, which was unexpected given the dramatic effects of BFA, expression of dominant inhibitory GBF1, or inhibition of COPI expression or function. Without being bound by theory, it is believed that the relatively mild effect of GBF1 siRNA on Golgi morphology and secretion of soluble proteins are a consequence of incomplete inhibition of GBF1 expression and function by the siRNA. In contrast, GCA is shown herein to have a pronounced effect on the Golgi which is rapidly and completely dispersed. As a result, the secretion of soluble cargo is abolished upon inhibition of GBF1 function with GCA.

The role of GBF1 in retrograde transport to the Golgi has not previously been investigated. The results described herein show that endocytic cargo is transported normally through recycling endosomes in the presence of GCA, indicating that GBF1 function is not required for these pathways. However, upon inhibition of GBF1 function, bacterial toxins are trapped in the endocytic compartment and are unable to reach the dispersed TGN. These findings indicate that GBF1 function is required for endosome-to-TGN transport. GCA can be used further for example to investigate whether GBF1 function is required for recruitment of endosome-to-TGN transport or whether instead that an intact TGN (localized adjacent to perinuclear recycling endosomes) is a prerequisite for retrograde transport.

More generally, small molecule inhibition offers several advantages over RNAi or transfection with dominant-negative mutants, most notably in its ability to inhibit protein function in essentially all treated cells independent of transfection efficiency. Additionally, a reversible small molecule inhibitor offers the ability to dynamically monitor the role of protein function and affords the opportunity to examine mechanisms of recovery from perturbations in protein function. Moreover, RNAi cannot completely inhibit protein expression, and in some cases small amounts of residual protein are sufficient to maintain normal function and phenotype. However, an inherent caveat shared by RNAi, dominant-negative expression, and small molecules, is the possibility of non-specific or 'off target' effects. Demonstrating the specificity of small molecules can be relatively difficult, as these compounds often exhibit non-specific or 'off target' effects at higher concentrations. In some respects BFA, though it has been an extremely valuable tool to study membrane transport, demonstrates substantial off-target effects. For example, by simultaneously inhibiting GBF1, BIG1 and BIG2, it has not been possible with BFA to individually study the role of these ArfGEFs in membrane transport. Off-target effects are also of concern when inhibiting gene expression by siRNA. In the case of RNAi, specificity is often proven by expressing an siRNA-resistant version of the targeted gene and demonstrating reversal of the phenotypic effects. The results described herein demonstrate that a similar approach proves that GCA is highly specific for GBF1. Expression of the GBF1-M832L mutant renders cells completely resistant to the effects of this compound, indicating that the phenotypic and functional effects of GCA do not result from non-specific or off-target effects. The marked specificity and rapid reversibility of GCA provides the ability to probe GBF1 function in maintaining Golgi structure and function. Given its surprisingly high level of specificity, potency and reversibility, GCA is a valuable tool for investigating mechanisms underlying assembly and transport in the Golgi.

The following examples are thus included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various aspects and iterations of the invention.

Materials and Methods for Examples 1-8:

Antibodies and Reagents: Compound GCA was purchased from ChemDiv, reconstituted to 10 mM in DMSO and stored at −20° C. The purity of GCA was confirmed by mass spectroscopy. Shiga-like toxin 1 was from List Biological Laboratories. Recombinant Alexa Fluor 488-labeled cholera toxin B subunit, Alexa Fluor 594-labeled human transferrin, Slow-Fade Gold mounting reagent containing DAPI, and Alexa Fluor-labeled donkey anti-IgG secondary antibodies were obtained from Molecular Probes. Rabbit anti-giantin polyclonal antibody was obtained from Covance, rabbit anti-hemagglutinin (HA) polyclonal antibody from Sigma-Aldrich, mouse anti-GM130 from BD Transduction, rabbit anti-human TGN38 from Santa Cruz, rabbit anti-βCOP from ABR, and mouse anti-ERGIC-53 from Axxora. DMEM, EMEM, and nonessential amino acids were obtained from Mediatech. Cycloheximide, DMSO, and brefeldin A (BFA), actinomycin B, and latrunculin B were from Sigma. [125I]-labeled bovine serum albumin ([125I]-BSA) and trans [35S] were purchased from MP Biomedicals, and [35S]O4 was obtained from American Radiolabeled Chemicals.

Cell Lines and Cell Culture: Vero (African green monkey kidney, CRL-1587), MDCK (Madin-Darby canine kidney, CCL-34), and 293A-HEK (Human embryonic kidney, CRL-1573) cells were obtained from the American Type Tissue Culture Collection (Manassas, Va.). 293A cells were obtained from Invitrogen. Vero cells were maintained in DMEM supplemented with 10% fetal calf serum and 1% nonessential amino acids at 37° C. under 5% CO2. MDCK cells were maintained in EMEM supplemented with 10% fetal calf serum and 1% nonessential amino acids at 37° C. under 5% CO2. 293A cells were maintained in EMEM with 10% heat-inactivated horse serum.

Transient transfections were performed using Lipofectamine 2000 (Invitrogen) in OptiMem media, following the manufacturer's recommendations. Following overnight incubation at 37° C. under 5% CO2, cells were collected into chamber slides (Lab-Tek, Campbell, Calif.) or appropriate dishes and incubated another 24 h before experimentation.

Radioactive protein synthesis assay: The luciferase-based high-throughput screen to identify inhibitors of Stx trafficking has previously been described (Saenz et al., 2007; Zhao and Haslam, 2005). Similarly, confirmation of positive hits from the ChemDiv4 library screen was assessed by a previously described radioactive [35S] incorporation assay adapted to a multi-well format (Saenz et al., 2007). Briefly, Vero cells cultured overnight at 37° C. and 5% CO2 in 96-well plates (2.5×104 cells/well) were treated with 0.5% DMSO (v/v) or media containing B06 or BFA at the indicated concentrations. Following a 0.5 h incubation at 37° C., toxin was added to wells in triplicate, and cells were shifted to 37° C. for an additional 4 h. Medium containing trans [35S] label at 10 mCi/ml was added, and cells were incubated at 37° C. for 45 min, washed with PBS (pH 7.4), and lysed (1 mg/ml BSA, 0.2% deoxycholic acid, 0.1% SDS, 20 mM Tris pH 7.4) at 4° C. for 12 h. Proteins from the lysed cells were TCA-precipitated (final concentration 15%), transferred to multi-screen HA plates (Millipore), and the filters were washed with ice-cold 20% TCA. Filters were then removed from the plate, placed in 2 mL Bio-Safe II scintillation fluid (RPI), and [35S] incorporation quantitated using a beta counter (Beckman). Independent experiments were performed at least three times for B06 and BFA, and data were analyzed using Prism v4.0 software (2003).

Immunofluorescence

For all immunofluorescence experiments, cells were fixed in 4% paraformaldehyde in cold PBS, permeabilized with 0.1% Triton X-100 in PBS, blocked, then probed with primary and secondary (Alexa Fluor 488 or 594-labeled donkey anti-IgG) antibodies diluted in blocking buffer (DMEM containing 10% fetal calf serum plus, 1 mg/ml BSA). Cells were rinsed thoroughly in PBS prior to mounting in SlowFade Gold reagent containing DAPI. Fluorescence imaging used epifluorescence (Zeiss) microscopy.

Cloning and Sequence Analysis of Canine Arf1 and GBF1 Sec7 Domain

Total RNA was isolated from approximately 107 MDCK cells by silica membrane binding (RNeasy, Qiagen) and contaminating chromosomal DNA was removed by DNase treatment (Qiagen). The cDNA was prepared from isolated RNA with random primers and SuperScript II reverse transcriptase (Invitrogen) according to the manufacturer's instructions. The Arf1 gene was amplified from MDCK cDNA.

The canine GBF1 Sec7 mRNA sequence (Bankit accession #1167731(SEQ ID NO: 11)) is:

The upstream primer used was 5'-GTCCTTCCACCTG TCCACAAGCATGGTTGTGAGGTGGGAG-CAAAACCAACG-3' (SEQ ID NO: 12) which was derived from to contain a region from the human 5' untranslated region with Kozak consensus sequence followed by nucleotides that matching both Arf1 genes in the database. The downstream primer was the same as that used to amplify human Arf1 (5'-CCGCGCTAGCC TGAGGCATAGTCAG-GCACGTCATAAGGATAGCCGTTCTTCTG-GTTCCGGAGCTGA TTGGACAGCC-3; SEQ ID NO: 13) since the canine and human database sequences were identical through this region. Two resulting clones were sequenced, revealing no differences in the Arf1 coding region between the two. The Sec7 domain of the canine GBF1 gene was amplified from MDCK cDNA (SEQ ID NO: 11) using primers 5'-CGATTTTCCTGTCTCCTGCCAGATCCACGGG-3' (SEQ ID NO: 14) and 5'CCACACATAGTTCT CCCGAAC-CAAGCC-3' (SEQ ID NO: 15), and the resulting product cloned into pcDNA3.1/V5/His. Four resulting clones were sequenced and compared to their human, hamster, and murine counterparts.

GBF1 Site-Directed Mutagenesis

The hamster GBF1 cDNA (SEQ ID NO: 9) a gift from Paul Melangon, University of Alberta, Edmonton, AB) was used as template for constructing HA-tagged wild-type and mutant cDNA. GBF1-HA was generated by PCR using primers GBF1-HA (5'-GCCGCGCTAGCCTGAGGCAT AGTCAG-GCACGTCATAAGGATAGCCGTTGACT-TCAGAGGTGGGAATAGGGTCTGT AG-3'; (SEQ ID NO: 3)) and the upstream GBF1 primer (5'-GACAGGTTTGC-CAAGATGGTGGATAAGAATATT TACATC-3'; (SEQ ID NO: 4). The resulting PCR product was cloned into pcDNA3.1D/V5-His-TOPO (Invitrogen) under control of the cytomegalovirus (CMV) promoter. The insert was sequenced to ensure its fidelity. The GBF1-M832L (SEQ ID NO: 10) and GBF1-E794K (SEQ ID NO: 16) mutants were generated using the QuikChange II XL Site-Directed Mutagenesis Kit (Stratagene). Mutagenic primers were E794K sense (5'-GC-CTTCCGTTTGCCCGGGAAGGCACCAGT-TATTCACAGGTTGC-3'; (SEQ ID NO: 5)), E794K antisense (5'-GCAACCT GTGAATAACTGGT GCCTTCCCGGGC AAACGG AAGGC-3'; (SEQ ID NO: 6)), M832L sense (5'-GGCCTATGCTGTCATCTTGCT-TAATACTGACCAGC-3'; (SEQ ID NO: 7)), and M832L

```
  1 attgccctte gattttcctg tctcctgcca gatccacggg aactgattga aattaaaaac 61 aaaaagaagc tgctaatcac tggcacagag cagttcaacc agaaaccaaa gaagggaatc 121 cagtttctgc aggagaaagg cctcctcacc atcccaatgg acaacacaga ggtagcccag 181 tggctccgag agaaccctcg gctggacaag aaaatgattg gagagtttgt gagtgaccgc 241 aaaaacattg acctgttgga gagctttgtg agcaccttca gctttcaggg tctgcggctg 301 gatgaagctc ttcgtctcta cctggaagcc tttcgcttac ctggggaagc accagtcatc 361 cagaggttgc tggaggcatt cacagagcat tggaggaatt gtaatggctc cccatttgcc 421 aatagcgatg cctgctttgc tctggcctat gctgtcatct tgcttaatac tgaccagcac 481 aaccacaacg ttcgcaaaca gaatgcaccc atgactctag aggagtttcg caaaaaccta 541 aaaggtgtga atggaggcaa ggactttgag caagacatcc tggaggacat gtaccatgcc 601 atcaagaatg aggaaattgt gatgcctgaa gagcagacag gcttggttcg ggagaactat 661 gtgtggaagg g
``` antisense (5'-GCTGGTCAGTATTAAGCAAGATGACAG-CATAGGCC-3'; (SEQ ID NO: 8). Mutant clones were sequenced to ensure their fidelity.

Preparation of Adenovirus Expressing GBF1-HA, GBF1-HA Mutants and Human-Canine Arf1 Switch Mutants Adenovirus expressing GBF1-HA constructs, canine Arf1 switch mutants, and NPY-GFP were prepared by cloning the appropriate cDNA into plasmid pENTR-11 then transferring the cDNA insert to plasmid pAD/CMV/DEST using the Clonase II reaction (all from Invitrogen). Crude adenoviral stocks were isolated from transfected 293A cells, which were then used to generate high titer stocks. Each was aliquoted and frozen at −80° C. until used for transduction. Control experiments were performed with each stock to determine conditions resulting in 100% transduction efficiency. Arf1-GTP pulldown assay.

Human ARF1 bearing a carboxy-terminal HA epitope tag was amplified from a human liver cDNA (Invitrogen) using flanking primers 5'-GTCCTTCCACCTGTCCACAAG-CATGGGG-3' (SEQ ID NO: 17) and 5'-CCGCGCTAGCCT-GAGGCATAGTCAGGCACGTCATAAGGATAGCCGTT CTTCTGGTTCCGGAGCTGATTGGACAGCC-3' (SEQ ID NO: 18). The resulting product was ligated into plasmid pCDNA3.1/V5/His. Nucleotide sequencing was performed to verify fidelity of the HA-tagged wild-type cDNA. Following overexpression, the localization of ARF1 was tracked by indirect immunofluorescence using a mouse anti-V5 (Invitrogen) primary antibody, followed by staining with the corresponding secondary antibody.

The VHS and GAT domains from human GGA3 were amplified from a human cDNA library using primers 5-GGC-CGAATTCATGGCGGAGGCGGAAGGGGAAAGC-3' (SEQ ID NO: 19). and 5'-CCGGCTCGAGTCAGTCAG-GCAGGGTTAAGGTAGCCACCTCG-3' (SEQ ID NO: 20). The resulting product was initially cloned into plasmid pcDNA3.1/V5/His and sequenced to ensure its fidelity. The product was then released by digestion with EcoRI and XhoI and ligated into similarly digested plasmid pGEX-6p1. Expression of the recombinant GGA3-GST protein was induced by the addition of IPTG and the protein purified from crude bacterial lysates on a GSTrap column (Pharmacia). The protein was dialyzed into 50 mM Tris pH 7.5 plus 100 mM NaCl and used in Arf1 pulldown assays using the protocol of Santy and Casanova 34, with the following modifications.

Vero cells were seeded in 10 cm3 dishes and transduced with adenovirus expressing Arf1-V5 alone, or co-transduced with virus expressing Arf1-V5 and virus expressing GBF1-ML-HA. After overnight incubation, the cells were washed, trypsinized, and seeded into three 25 cm3 flasks each. The following day, monolayers were treated at 37° C. for 45 min with media alone, or media containing BFA (10 mg/ml) or GCA (10 mM). The cells were then washed with cold PBS and scraped into 1 ml lysis buffer (50 mM Tris pH 7.6, 100 mM NaCl, 2 mM MgCl2, 1% SDS, 1% Triton X-100, and 10% glycerol). To each sample was added 48 mg of GGA-GST bound to 30 ml of glutathione agarose (Pierce Chemical Company). The samples were incubated rocking at 4° C. for 30 mins, then the beads pelleted and washed three times with cold GGA wash buffer (50 mM Tris pH 7.6, 100 mM NaCl, 2 mM MgCl2, 1% NP-40, and 10% glycerol). SDS-PAGE loading buffer was added, the samples were boiled, and equal aliquots separated by SDS-PAGE. Arf1 was detected by Western blot using anti-V5 antibody (Invitrogen) followed by enhanced chemiluminescence. Band intensity was determined using the program ImageJ. The results of duplicate experiments were averaged.

Toxin and Transferrin Internalization:

For cholera toxin B subunit (CtxB) and transferrin trafficking experiments, Vero cells grown in chamber slides (2.5×104 cells/chamber) were treated with serum-free medium containing DMSO, B06, or BFA at the indicated concentrations and times at 37° C. Following the binding of toxin and transferrin at 4° C., cells were shifted to 19° C. for 1 h to allow for toxin internalization. Cells were processed for immunofluorescence as described above.

Expression and Trafficking of VSVG-GFP:

Vero cells were transiently transfected with VSVG-GFP ts045 using Lipofectamine 2000 (Invitrogen) In some experiments, cells were co-transfected with GBF1-HA WT or M832L plasmids. After overnight incubation at 37° C. in 5% CO2, cells were collected and placed into chamber slides (Lab-Tek) for an additional 8-10 h at 37° C. before their transfer to 42° C. for 12-16 h. Cells were then treated with cycloheximide (100 mg/ml) to prevent de novo protein synthesis and either no compound, GCA (10 mM), or brefeldin A (10 mg/ml) then transferred to 32° C. Cells were fixed following various incubation times at 32° C. Fixation, permeabilization, staining, and imaging were performed as described for immunofluorescence experiments.

NPY-GFP Secretion:

The NPY-GFP assay was similar to that previously reported (Saenz et al., 2007), with slight modifications. Briefly, 106 Vero cells were transduced overnight at 37° C. in 5% CO2 with pAD-NPY-GFP. Cells were then washed, trypsinized, and seeded into a 96-well plate (~1×104 cells/well). The next day, the cells were washed once with PBS then incubated at 37° C. with media containing DMSO, BFA (10 mg/ml), or B06 (10 mM). Supernatants were collected at various times thereafter. GFP quantitation was performed by ELISA using anti-GFP coated plates (Pierce) and rabbit anti-GFP in solution. Mean absorbance for control wells containing DMEM alone were subtracted from sample wells. Calculation of GFP concentration was performed by comparison to a recombinant GFP (rGFP; XX) standard curve.

Sulfation of StxB-SS-His:

A StxB construct containing a tandem of carboxy-terminal sulfation sites and a histidine tag for purification (StxB-SS-His) has been described (Saenz et al., 2007). Vero cells seeded in a 6-well plate (1×106 cells/well) were washed three times in serum-free DMEM lacking sulfate (Washington University Tissue Culture Support Center), and then incubated in sulfate-free medium for 3.5 h at 37° C. After treatment with DMSO (0.5% v/v), BFA (10 mg/ml) or GCA (10 mM) 30 min at 37° C., media was replaced with sulfate-free media containing these compounds plus StxB-SS-His (1 mg/ml) and 1 mCi/ml [35S]O4 for 3 h at 37° C. Wells were washed with cold PBS (pH 7.4) and lysed with PBS containing 1% Triton X-100. Lysates were added to 40 µl Ni-NTA Superflow beads (Qiagen) and rotated at 4° C. overnight. Beads were washed once with PBS containing 1% Triton X-100 and twice with PBS, then resuspended in imidazole (1.5 M in PBS). Eluates were resolved on a 10-20% Tris-HCl denaturing gel, treated with EnHance reagent (DuPont), dried and exposed to film. Band intensity was determined using ImageJ software.

Live Cell Imaging:

NRK cells were transiently transfected using FuGENE 6 Transfection Reagent according to the manufacturer's instructions (Roche Molecular Biochemicals). Cells were analyzed 15-24 h after transfection. Imaging was performed on a Zeiss LSM 510 Meta at 37° C. in DMEM medium supplemented with 20 mM Hepes. All plasmids used for live cell imaging were previously described (Liu et al., 2005).

Transferrin Recycling Assay:

Transferrin (Tf) recycling was analyzed by modification of a previously published assay for recycling of low density lipoprotein related protein (van Kerkhof et al., 2005). 2×105 Vero cells were seeded per well in seven 12-well dishes. The following day, media was removed and replaced with 500 ml serum-free media containing Tf-488 (Invitrogen) at 5 mg/ml and either no compound or B06 (10 mM). The samples were incubated at room temperature for 60 min to allow Tf transport to recycling endosomes. Cells were washed twice with 1 ml PBS, then overlaid with 400 ml media containing 10% FCS, anti-AlexaFluor-488 antibody (Invitrogen) at 15 mg/ml, and either no compound, BFA (10 mg/ml), or B06 (10 mM). T=0 min samples were maintained at room temperature to prevent recycling. The remaining samples were incubated at 37° C. and at various times ranging from 10 to 60 min. Media was removed, and 500 ml prewarmed cell release buffer (Sigma) was added. Cell suspensions were mixed with 250 ml 4% paraformaldehyde, and mean fluorescence was determined by FACS on a Becton Dickenson FACSCaliber System. Mean fluorescence of the T=0 samples was normalized to 100% fluorescence.

Example 1

Figure 2:
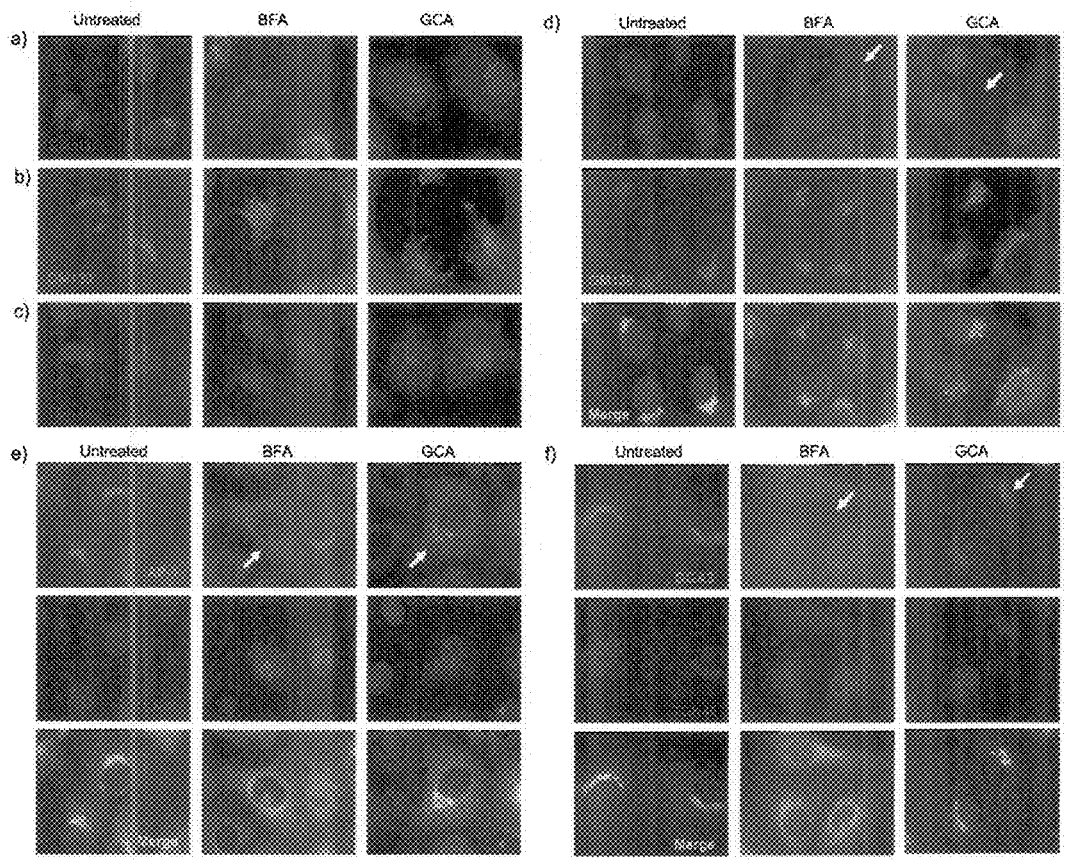
FIG. 2 is a series of photomicrographs of Vero cells treated with fluorescent stains indicating medial- and cis-Golgi, COPI recruitment, and localization of AP-1 and GGA3 to The Golgi Network (TGN), and comparative results in cells left untreated (left columns), treated with brefeldin A (BFA) (center columns), or treated with GCA (right columns).

Golgicide A (GCA) is a Potent and Highly Effective Inhibitor of Shiga Toxin Activity Vero cells were pretreated for 30 min at 37° C. with varying concentrations of GCA in solution, followed by incubation with shiga toxin (Stx, 1 ng/mL) for 4 h at 37° C. FIG. 1 shows graphs of the effects of Golgicide A in (A) as normalized level of protein synthesis against varying micromolar concentrations of GCA and in (B) as normalized level of protein synthesis in control and GCA-treated cells against varying concentrations of shiga toxin (Stx).

Referring to FIG. 1A, percent protein synthesis indicates the amount of radioactive amino acid incorporation in GCA-treated cells as a percentage of radioactive amino acid incorporation in cells lacking Stx treatment (control). Protein synthesis levels and compound-response curves were determined as described in Methods. FIG. 1B shows protein synthesis levels for control (squares; no compound), BFA-(dotted line), and GCA-treated Vero cells (diamonds) as determined using the radioactive amino acid incorporation assay as described for FIG. 1A. Percent protein synthesis is expressed as the amount of radioactive amino acid incorporation in untreated, BFA-, or GCA-treated cells at a given toxin concentration as a percentage of radioactive amino acid incorporation in cells lacking Stx treatment. Toxin $IC_{50}$ values for BFA- and GCA-treated cells were significantly increased over control cells ($p<0.01$, not shown). For FIGS. 1A and 1B, data points (mean±SD) represent triplicate data at the indicated compound or toxin concentrations, respectively, from one representative experiment.

Thus, from a high-throughput screen for small molecules that inhibit the effect of bacterial toxins on host cells, GCA was shown to potently and effectively protect Vero cells from shiga toxin. GCA inhibited the effect of shiga toxin on protein synthesis with an $IC_{50}$ of 3.3 μM. When treated at a concentration of 10 μM, Vero cells where highly protected against the effects of shiga toxin.

Example 2

GCA Causes Reversible Dissociation and Dispersal of the Golgi and TGN

Given the results described in Example 1, it was thought that GCA might have an effect on toxin trafficking and on intracellular organelle morphology. Immunofluorescence experiments were performed to track cellular morphology in response to GCA exposure. FIG. 2 is a series of photomicrographs of Vero cells treated with fluorescent stains indicating medial- and cis-Golgi, COPI recruitment, and localization of AP-1 and GGA3 to The Golgi Network (TGN) and endosomes, and left untreated, treated with GCA, or treated with brefeldin A (BFA). The results showed surprisingly dramatic and specific effects of GCA on the Golgi and TGN. GCA disperses medial- and cis-Golgi, inhibits COPI recruitment, and maintains localization of AP-1 and GGA3 to TGN and endosomes.

FIG. 2A (upper left of figure) shows results in Vero cells that were either left untreated or treated with BFA (10 mg/mL) or GCA (10 mM) for 1 hr and the localization of giantin (medial-Golgi; red) and GM130 (cis-Golgi; green) were determined. The distribution of medial- and cis-Golgi was similar in BFA and GCA treated cells. FIG. 2B shows Vero cells treated for 5 min with BFA (10 μg/mL) or GCA (10 μM) showing dispersed COPI staining (red) that does not colocalize with the Golgi (green) as in untreated cells. FIG. 2C shows that unlike BFA, GCA maintains AP-1 (green) association with the TGN (red) after 5 min of treatment (see arrows). FIG. 2D shows Vero cells treated for 5 min with BFA (10 μg/mL) showing a diffuse GGA3 staining pattern (green) compared to GCA-treated cells (10 μM), which showed GGA3 colocalizing with TGN (red) similar to untreated cells. Blue staining indicates nuclei.

FIG. 3 is a series of photomicrographs of results of further experiments showing that GCA exposure causes tubulation and subsequent dispersal of Golgi and TGN. More specifically, FIG. 3 shows the results obtained when Vero cells were treated with GCA (10 μM) and then fixed and labeled with anti-TGN46 (red) and anti-giantin (green) antibodies at periods of 2, 5, 10, 15 and 20 minutes post exposure to GCA. Both the TGN and medial-Golgi begin to disassemble within 5 min of treatment, and the insets demonstrate giantin-positive tubules (arrows) at the indicated times. Time course experiments thus revealed that the Golgi initially became extensively tabulated prior to its complete dispersal (FIG. 3), similar to the effects of BFA on cis- and medial-Golgi. Treatment with GCA resulted in diffuse and punctuate distribution of the medial-Golgi marker giantin.

FIG. 4 is a series of photomicrographs showing that BFA and GCA disperse the medial-Golgi marker giantin to a partially punctate pattern adjacent to ERES. Vero cells were treated with BFA (10 mg/ml) or GCA (10 mM) for 60 mins then fixed and labeled with antibodies against giantin (red) or Sec31 (green). Both compounds cause giantin redistribution into a hazy and punctate pattern. Giantin-positive punctate structures are closely approximated to Sec31-labeled ERES. Punctuate structures were in contact with Sec31-positive foci, indicating their association with endoplasmic reticulum exit sites (ERES; FIG. 4). Thus, whereas the Golgi remains as a tightly organized perinuclear ribbon in untreated cells, GCA caused complete dispersal of the Golgi marker giantin. This effect was seen at concentrations as low as 5 μM. Within two minutes of GCA addition, giantin labeling became extensively tubulated and had completely dispersed by 15 min. Unexpectedly, these morphological effects were highly reminiscent of those caused by BFA. The distribution of cis-Golgi and medial-Golgi markers were essentially identical following either GCA or BFA treatment.

However, the effects of BFA and GCA on the TGN were surprisingly different. Whereas BFA induced the formation of tubules derived from TGN endosomes, GCA caused the TGN to disperse into small vesicles that subsequently disseminated throughout the cell. For example, FIG. 2C shows the different patterns of TGN labeling with TGN46 in BFA treated cells (middle column) and GCA-treated cells (right column). FIG. 5 is a series of photomicrographs showing that BFA and GCA have distinct effects on the TGN and endosomes. Vero cells were treated with BFA (10 mg/ml) or GCA (10 mM) for 15 mins then fixed and labeled with antibodies against TGN46 (red) or transferrin receptor (Tfn; green). Whereas BFA treatment resulted in tubulation and partial overlap of TGN and recycling endosomes, GCA caused both to disperse into punctate structures that did not co-localize.

The results shown in FIG. 6 demonstrate that the morphologic effects of GCA did not result from disruption of microtubules or actin cytoskeleton. Referring to FIG. 6A, Vero cells were treated for 30 min at 37° C. with DMSO, GCA, or nocodazole at the indicated concentrations prior to fixation and immunostaining, as described elsewhere herein. At 10 µM, GCA had no observable effects on microtubules, while nocodazole, an inhibitor of microtubule polymerization, produced drastic morphological effects. In referring to FIG. 6B, Vero cells were treated with DMSO, GCA, or cytochalasin B at the indicated concentrations and developed for immunofluorescence, as in (A). GCA showed no effects on actin microfilaments compared to DMSO-treated cells, while the actin-depolymerizing agent cytochalasin B induced significant changes to actin morphology. [0001].

The results shown in FIG. 7 demonstrate that GCA does not affect transport through recycling endosomes. FIG. 7A shows that GCA treatment maintains endocytic transport to recycling endosomes. Vero cells were treated for 15 min with DMSO (control; 0.5% v/v) or GCA (10 µM), then incubated with AlexaFluor 594-labeled CtxB (1 µg/mL) and 488-labeled Tfn (1 µg/mL) for 1 h at 4° C. in serum-free medium prior to shifting cells to 19° C. for an additional hour. Cells were then fixed and developed for immunofluorescence. GCA, similar to control cells, did not affect CtxB trafficking to a juxtanuclear, Tfn-positive recycling endosome compartment. Blue, nuclei. In FIG. 7B, the graph shows that GCA treatment does not affect the kinetics of transferrin recycling. Vero cells were left untreated or were treated with GCA for 1 h. Cells were allowed to internalize AlexaFluor-488 labeled transferrin for 60 min. Fresh media containing quenching anti-AlexaFluor-488 antibodies were added, and at various times the cells were harvested and fixed (see Supplementary Methods). Each time point was performed in triplicate, and the mean and standard deviation of each is presented. All data were fitted by nonlinear regression assuming one phase decay, and half-lives (in min; inset) were calculated using GraphPad Prism. CtxB, cholera toxin B subunit; Tfn, transferrin. Thus, GCA does not interfere with transit of transferrin through the endocytic and recycling pathways.

Figure 8:
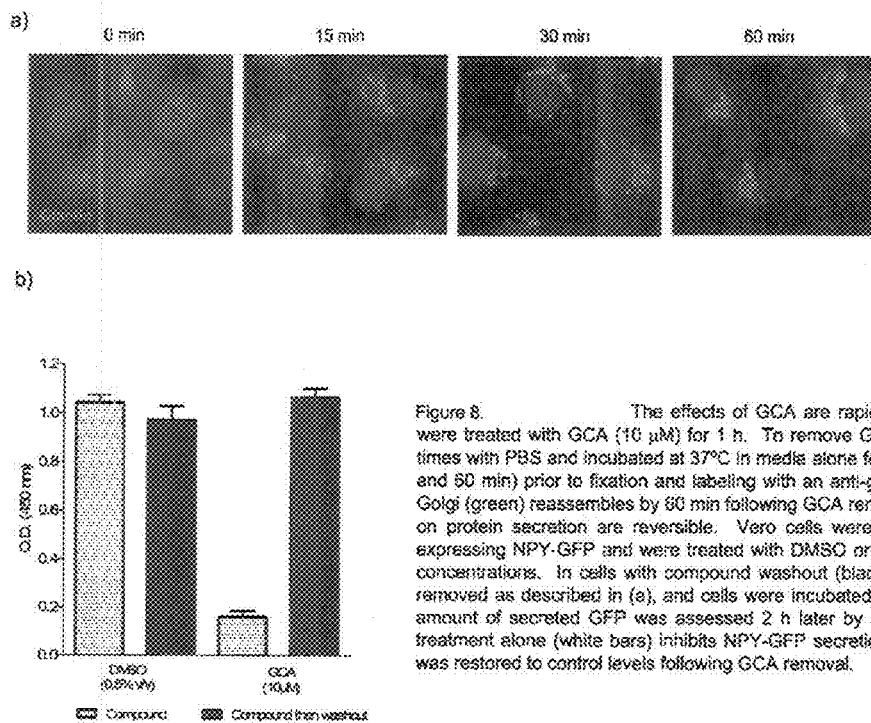
FIGS. 8A and B show (8A) photomicrographs of Vero cells treated with GCA followed by GCA removal and labeled with anti-giantin antibodies at various time points post GCA-removal, and (8B) a bar graph illustrating the reversible effects of GCA on protein (NPY-GFP) secretion in Vero cells transduced with adenovirus expressing NPY-GFP and treated with GCA for 1 hr followed by wash-out of GCA.

Finally, the effects of GCA were found to be rapidly reversible. For FIG. 8A, Vero cells were treated with GCA (10 mM) for 1 h. To remove GCA, cells were washed three times with PBS and incubated at 37° C. in media alone for various times (t=0, 15, 30, and 60 min) prior to fixation and labeling with an anti-giantin antibody. The medial-Golgi (green) reassembles by 60 min following GCA removal. FIG. 8B shows that the effects of GCA on protein secretion are also reversible. Vero cells were transduced with adenovirus expressing NPY-GFP and were treated with DMSO or (0.5% v/v) or treated with GCA (10 mM) for 1 hr. The cells were then washed in media containing no compound (washout) or GCA was added for 1 hr. Fresh media with or without GCA was added and after 2 hrs the amount of GFP secreted into the media was determined by ELISA. GCA treatment alone (white bars) inhibits NPY-GFP secretion, while NPY-GFP secretion was restored to control levels 1 hr after removal of GCA The rapid reversibility of GCA's effects was exploited to investigate the mechanism of Golgi reassembly. Cells were treated with GCA to disperse the cis/medial-Golgi and TGN. During compound washout, protein synthesis was inhibited by the addition of cycloheximide. If the TGN was derived from cis/medial- and trans-Golgi membranes, TGN46-labeling should remain dispersed after GCA washout and newly formed TGN should be devoid of de novo TGN46 protein. Specifically, Vero cells were treated for 3 hrs with cycloheximide (CHX; 100 mg/mL) plus GCA (10 mM). The media was removed and replaced with CHX plus no additional compound and the cells incubated for the indicated times before fixation and labeling with anti-GM130 and anti-TGN38 (not shown). Within 15 mins of GCA removal, dispersed TGN46-labeled vesicles reassembled into a typical TGN morphology adjacent to Golgi membranes, showing reassembly of The Golgi and TGN in the absence of de novo protein synthesis. Dispersed TGN rapidly reassembled adjacent to the Golgi. These results indicate that the reassembled TGN was derived by recruitment of dispersed TGN to reforming Golgi stacks and indicate that GBF1 activity is required to provide a scaffold for TGN localization.

Example 3

GCA Disperses COPI but not AP1 or GCA3 from Golgi Membranes

BFA inhibits Arf1 activation, resulting in the rapid dispersal of Golgi-associated vesicle coat proteins COPI and AP-1 at the Golgi and TGN, respectively. As shown in Example 2 above, since the effects of compound GCA on the Golgi were found comparable to those of BFA, the effects of GCA on COPI, AP-1 and GCA3 were also examined by comparing BFA- and GCA-treated cells. GCA treatment resulted in a rapid redistribution of COPI from the Golgi, which was evident in 5 minutes, prior to morphologic changes to Golgi structure and was similar to the effect of BFA, as shown in FIG. 2D. In contrast, AP-1 (FIG. 2E) and GCA3 (FIG. 2F) remained associated with the TGN until the Golgi and TGN began to disseminate. These results were distinct from those of BFA, which in contrast caused rapid dispersal of AP-1 and GCA3 to a diffuse cytoplasmic distribution within minutes of BFA addition.

The results establish that GCA and BFA have similar phenotypic effects on medial- and cis-Golgi, which correlate with rapid dispersal of COPI from Golgi. However, the results also establish that BFA and GCA have unexpectedly different effects on the TGN, which are correlated to differing effects on AP-1 and GCA3 localization. Together these observations indicate that GCA specifically targets GBF1, the ArfGEF responsible for Arf1 activation and COPI recruitment to cis-Golgi membranes.

Example 4

Phenotypic Effects of GCA are Similar to Expression of Dominant-Inactive GBF1

Figure 3:
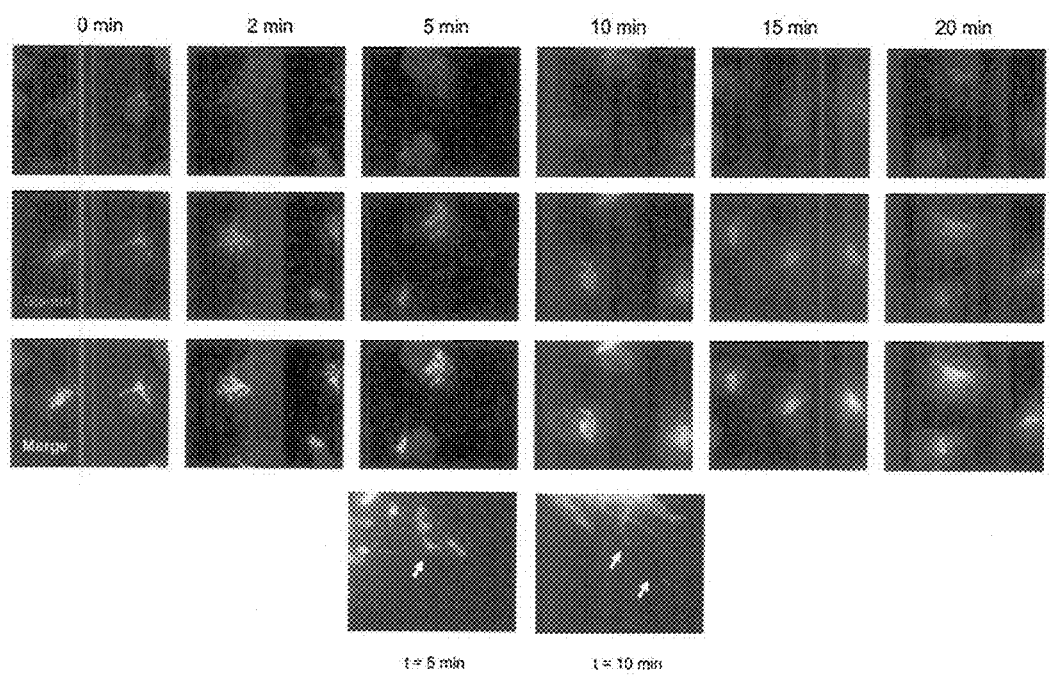
FIG. 3 is a series of photomicrographs of Vero cells treated with GCA (10 µM) for the indicated times prior to fixation and labeling with anti-TGN46 (red) and anti-giantin (green) antibodies showing that GCA causes tubulation and subsequent dispersal of the Golgi and TGN (insets demonstrate giantin-positive tubules (arrows) at the indicated times).
Figure 9:
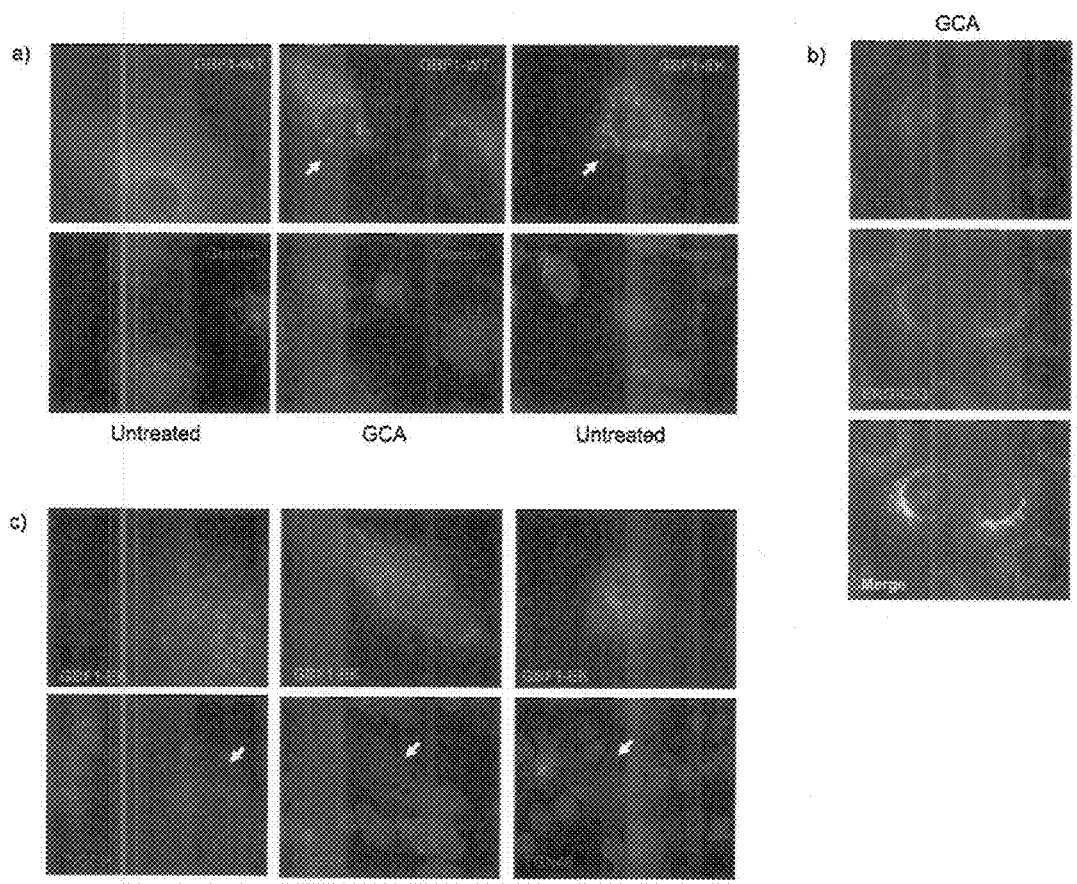
FIG. 9 is a series of photomicrographs showing results of immunoflourescence staining in GCA-treated cells revealing GCA effects similar to expression of inactive GBF1-E794K.

To further examine the specificity of GCA for GBF1, the effect of GCA on GBF1 localization was examined and compared to that of a dominant-inactive GBF1. FIG. 9A shows results demonstrating that inactive GBF1 localizes to punctate peripheral structures. Vero cells were transiently transfected with GBF1-WT and then were left untreated or exposed to GCA (10 mM for 1 hr) and then compared to untreated cells expressing GBF-E794K. The cells were fixed and labeled with anti-HA (GBF1-WT or GBF1-EK; green) and anti-giantin (red). In untreated cells, GBF1 localized to the Golgi and cytoplasm (FIG. 9A). Upon GCA treatment, GBF1 redistributed to dispersed punctate structures that partially overlapped with the Golgi marker giantin, similar to the distribution of inactive GBF1 bearing a glutamate for lysine substitution at residue 794 (GBF1-E794K; FIG. 3A). FIG. 9B shows that GBF1-WT (green) is predominantly membrane associated in GCA-treated cells and distributed to punctate structures that co-label with anti-ERGIC53. The dominant inactive GBF1 was previously shown to localize to the ER-Golgi intermediate compartment (ERGIC) 21, and we likewise found that upon GCA treatment, wild-type GBF1 was largely colocalized with ERGIC-53, a marker for this compartment (FIG. 9B). These results suggest that inactive GBF1 is trapped on ERGIC membranes.

FIG. 9C shows that Vero cells expressing the GBF1-EK mutant induce dispersal of β-COP, the medial-Golgi (giantin), and the trans-Golgi network (TGN48). Arrows indicate GBF1-E794K-overexpressing Vero cells. As seen with GCA treatment, expression of GBF1-E794K resulted in dispersal of β-COP from Golgi membranes and disruption of TGN and medial-Golgi structure (FIG. 9C). In summary, treatment with GCA phenotypically resembled expression of dominant-inactive GBF1, further indicating that GBF1 was the target of GCA.

Example 5

Figure 10:
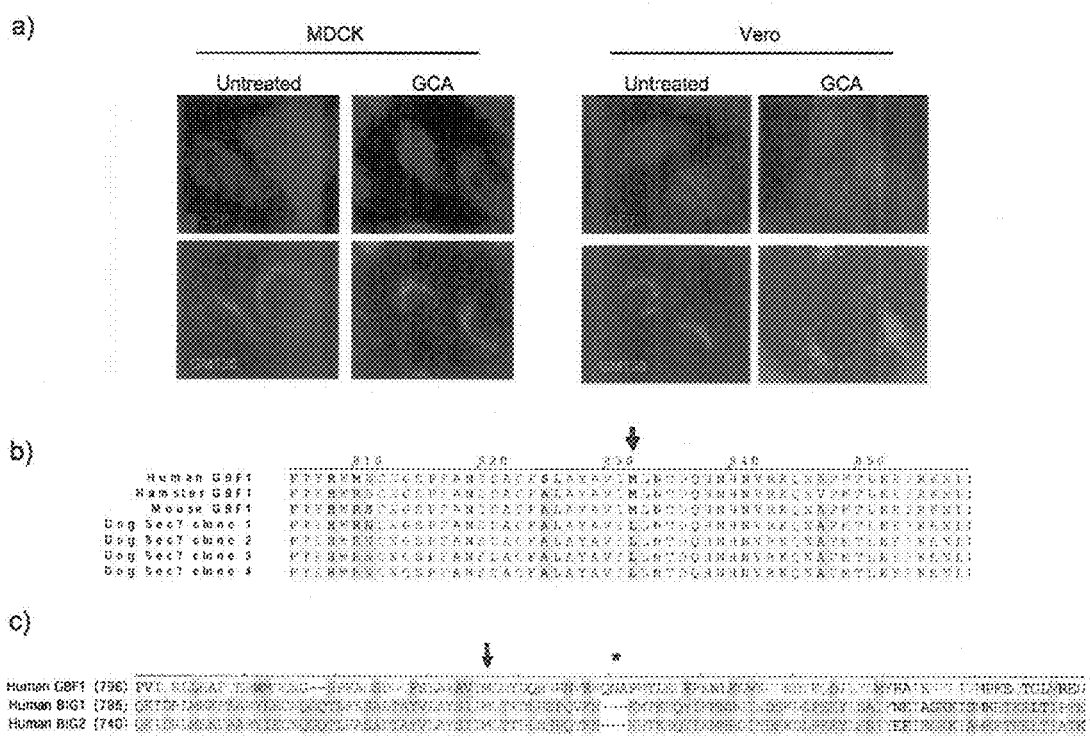
FIGS. 10A, B and C show (10A) a series of photomicrographs of MDCK cells and Vero cells that were left untreated or treated with GCA, (10B) a sequence comparison of published mammalian orthologues to four clones resulting from amplification of the Sec7 domain of GBF1 from MDCK cDNA, and (10C) a sequence comparison of the Sec7 domains of human GBF1, BIG1 and BIG2.

MDCK Cells are Resistant to GCA: A Single Nucleotide Substitution in Canine GBF1 Results in Resistance to BFA and GCA The data from Examples 1-3 indicated that GCA specifically inhibits vesicle coat recruitment at the cis-Golgi and results in similar morphologic abnormalities as expression of inactive GBF1. These data are consistent with GCA acting through the inhibition of GBF1. The Golgi apparatus of MDCK cells has been reported to be resistant to the effects of BFA. MDCK cells were tested for susceptibility to the effects of GCA treatment. Referring to FIG. 10, MDCK cells were found also to be resistant to GCA.

FIG. 10A shows the results of immunofluorescence experiments tracking βCOP (red) or GM130 (green) localization in MDCK (left) and Vero (right) cells that were left untreated or treated for 1 hr with GCA (10 mM). GCA did not affect βCOP localization or GM130 distribution in MDCK cells, while in contrast in Vero cells both βCOP and GM130 were dispersed following GCA treatment.

The possibility existed that the mechanism underlying GCA resistance in MDCK cells was similar to that for BFA resistance in the cells. Since BFA binds to specific residues in both Arf1 and the Sec7 domain of large ArfGEFs, the possibility existed that BFA and GCA resistance might result from polymorphisms in canine homologues of Arf1 or GBF1. Query of the canine genome database revealed two sequences with high homology to Arf1. Both of these differed from all other mammalian Arf1 orthologues within the interswitch region, which is known to contribute to BFA binding. For FIG. 10B, the Sec7 domain of GBF1 was amplified from MDCK cDNA, cloned and sequenced. The sequence of four resulting clones was compared to published mammalian orthologues (human, hamster, mouse). A methionine for leucine substitution was identified at residue 832 in the full-length canine peptide (residues numbered according to the human GBF1 sequence), consistent with the published genome sequence (arrow).

Comparison with all other mammalian GBF1 homologues revealed this methionine to leucine substitution to be unique to the canine gene. Notably, the methionine residue is known from structural studies to interact with BFA. A yeast mutant selected for BFA resistance was found to have an identical substitution in the GBF1 homologue Gea1 (Peyroche et al., 1999). Finally, the corresponding methionine to leucine substitution was introduced into the human GBF1 gene and demonstrated resistance to BFA as indicated by its inability to be trapped on membranes in the presence of BFA (Niu et al., 2005). This region is otherwise highly conserved among GBF1 orthologues, but demonstrates considerable sequence divergence from the corresponding region in BIG1 and BIG2.

FIG. 10C shows a comparison of the Sec7 domains of human GBF1, BIG1 and BIG2, which reveals the corresponding methionine to be conserved among these ArfGEFs (arrow), while there is considerable divergence in the GBF1 and BIG1/BIG2 Sec7 domains.

Figure 11:
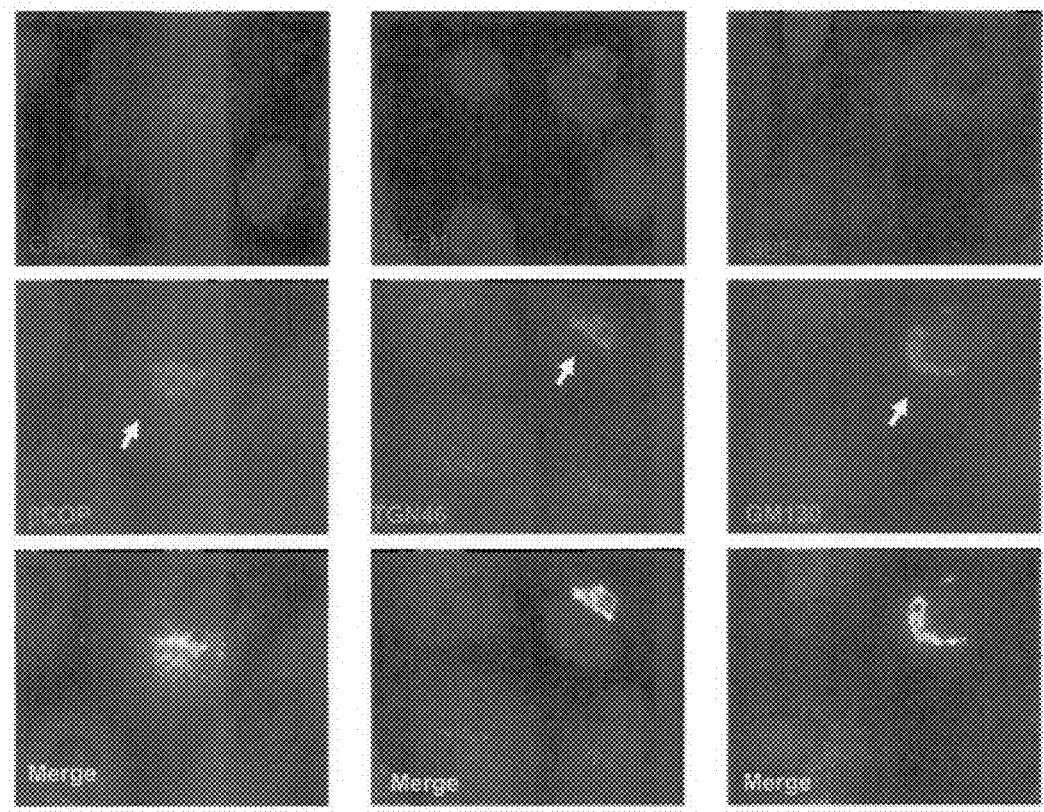
FIG. 11 is a series of photomicrographs showing β-COP, TG46, and GM130 localization in Vero cells after transient transfection with GBF1-ML (red) and exposure to 100 mg/ml GCA.

The M832L substitution was introduced into the hamster GBF1 and the effect of its expression on BFA and GCA susceptibility was examined in transfected cells. Cells expressing the GBF1-M832L mutant were shown to be resistant to GCA. FIG. 11 shows the results obtained when Vero cells were transiently transfected with GBF1-M832L (red) and exposed to 100 mg/ml GCA. Top row shows GBF1-ML expression. Second row, left to right respectively shows β-COP, TGN46, and GM130 localization, which was resistant to the effects of GCA. Blue indicates nuclei. Arrows indicate cells expressing GBF1-ML. Thus, βCOP localization, TGN structure, and cis-Golgi structure were maintained in cells expressing GBF1-M832L in the presence of GCA, even at compound concentrations as high as 250 μM (not shown). These results reveal that the leucine for methionine substitution in canine GBF1 enables resistance both to BFA and GCA. As described elsewhere herein, expression of a GBF1-M832L likewise rescued the effects of GCA on the secretory pathway and on intracellular toxin transport. The ability of GBF1-M832L to fully protect Vero cells against GCA's phenotypic effects indicates that GCA specifically targets GBF1 and does not demonstrate 'off target' effects.

Example 6

GCA Causes a Decrease in GBF1-Mediated Arf1 Activation

GBF1 facilitates the exchange of GDP for GTP on Arf1 5,6. To determine whether GCA affected GBF1-mediated Arf1 activation, cells were treated with this compound or with BFA and Arf1-GTP was isolated from cellular extracts 34. More specifically, Vero cells were transduced with Arf1-V5 alone or Arf1-V5 plus GBF1-M832L-HA and then exposed either to no compound (Untreated), BFA (10 mg/ml) or GCA (10 mM) for 1 hr. The cells were then lysed and extracts incubated with immobilized GST-GGA3. Bound proteins were released and separated by SDS-PAGE. Arf1-V5 was detected by Western blot and band intensity was determined using ImageJ software. Statistical analysis was performed on duplicate experiments. (*, statistically significant from untreated sample [P=0.05]; ns, not statistically significantly different from untreated sample).

Figure 12:
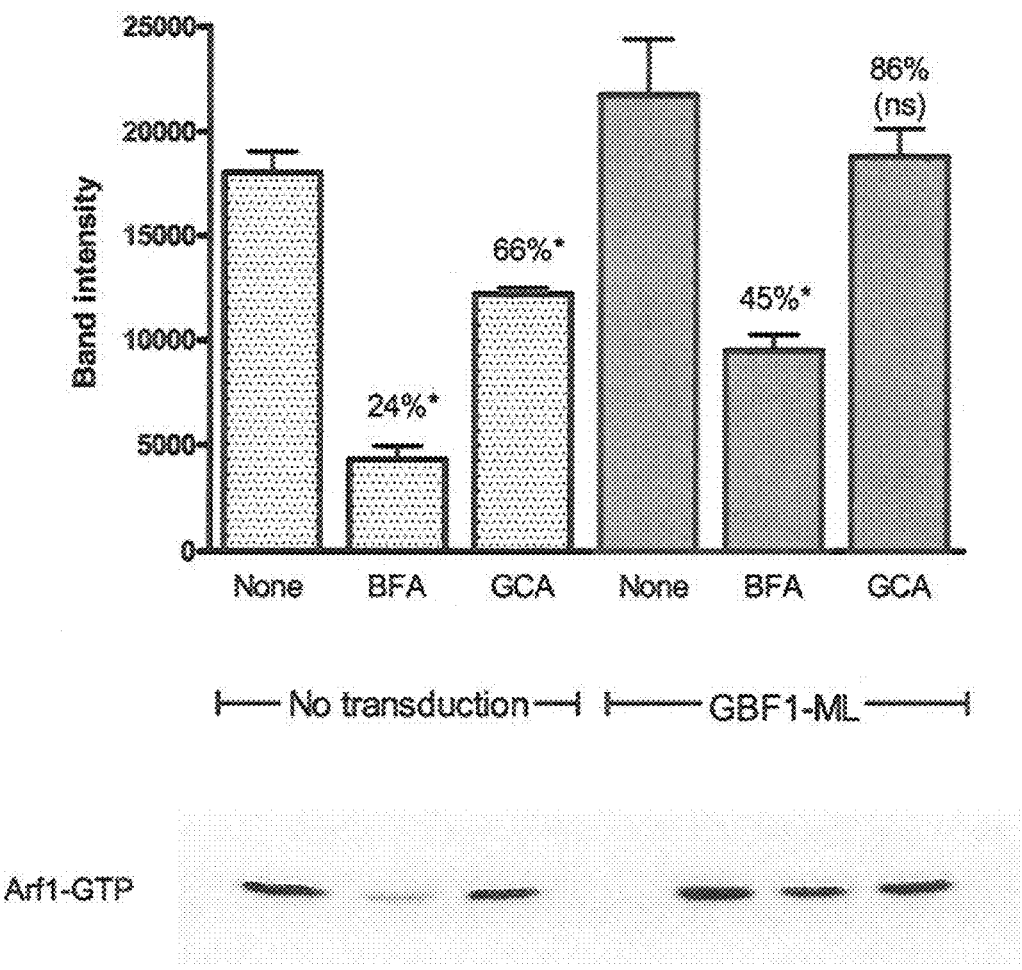
FIG. 12 is a bar graph of results obtained when Vero cells were transduced with Arf1-V5 alone, or with Arf1-V5 plus GBF1-M832L-HA, and then were exposed either to no compound (Untreated), BFA (10 mg/ml) or GCA (10 mM) for 1 hr.

GCA caused a consistent and statistically significant decrease in Arf1 activation, averaging 34% (FIG. 12).

BFA caused a greater decrease in Arf1-GTP, approximating 75%, which was expected given this compound's more promiscuous effects on ArfGEFs. In order to directly determine whether the effect of GCA on Arf1 activation was due to inhibition of GBF1 function, cells were transduced with the GCA- and BFA-resistant GBF1-M832L mutant and Arf1-GTP levels were assessed in cells treated with these compounds. Whereas GBF1-M832L expression restored Arf1-GTP to approximately 45% of control in BFA-treated cells, Arf1 activation was increased to 86% of control in GCA-treated cells (FIG. 12). Interestingly, expression of GBF1-M832L resulted in increased cellular Arf1-GTP levels in untreated cells. In summary, GCA caused a decrease in Arf1 activation that was attenuated in cells expressing the GCA-resistant mutant.

Transduction with GBF1-M832L is less than 100% efficient. Vero cells were transduced with GBF1-M832L to be used in Arf1 activation assay. An aliquot of cells was seeded in a slide chamber. Simultaneous with cells used for an Arf1-GTP pulldown assay, these cells were treated with GCA for 1 hour then fixed and labeled with antibodies against HA (GBF1; red) or giantin (green). Nuclei were labeled with DAPI. GBF1 expression varies from cell to cell, with about 85% of cells expressing detectable GBF1. These cells are protected from the effects of GCA, while approximately 15% express low or undetectable GBF1 and are not protected from GCA (white asterisk).

The results indicate that the Inability to restore Arf1-GTP in GCA-treated cells to 100% of the level in untreated cells was likely due to minimal GBF1-M832L expression in approximately 15% of cells (FIG. 13). BFA caused a much larger decrease in cellular Arf1-GTP and the effect was only partially reversed by the expression of GBF1-M832L. Both of these observations are explained by the effects of BFA on ArfGEFs other than GBF1. The data also provide a rough estimate of the relative contribution of GBF1 and other Arf-GEFs to cellular Arf1 activation. In Vero cells growing in tissue culture conditions, the results indicate that GBF1 accounts for approximately 30% of cellular Arf1 activation, BIG1 and BIG2 account for approximately 45%, and BFA-resistant Arf1 GEFS, such as ARNO, account for the remainder.

Example 7

GCA is Selective for GBF1

Figure 14:
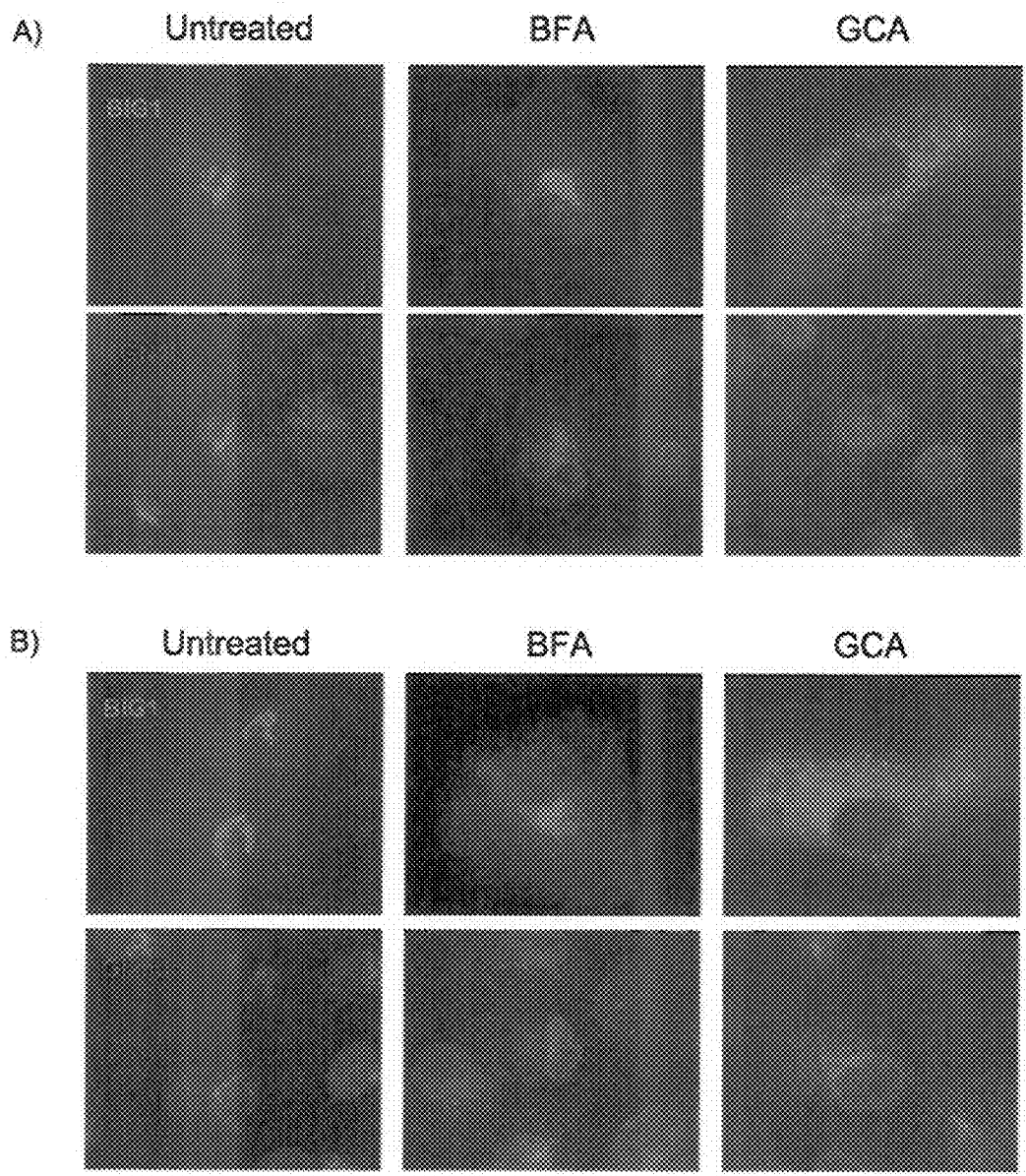
FIGS. 14A and B is a series of photomicrographs showing that GCA is a specific inhibitor of GBF1.

The results presented thus far suggest that GCA is a specific inhibitor of GBF1. In order to further investigate the differing specificities of GCA and BFA, we examined the effect of BIG1 overexpression on susceptibility to these two compounds. Previous reports showed that overexpression of BIG1 partially rescues the effects of BFA on the TGN 16. For FIGS. 14A and B, Vero cells were transiently transfected with BIG1-HA, exposed either to BFA (10 mg/ml) or GCA (10 mM) for 1 hr, then labeled with anti-HA plus either (14A) anti-giantin or (14B) anti-TGN46. The results showed that BIG1 transfection was partially protective against BFA effects on the TGN (FIG. 14A) and had no protective effect at the Golgi (FIG. 14A). By comparison, expression of BIG1 had no protective effect against GCA on either the TGN (FIG. 14A) or the Golgi (FIG. 14B).

The mechanism of GCA specificity for GBF1 was investigated by molecular modeling and site-directed mutagenesis. The observation that the GBF1-M832L mutant was resistant to both BFA and GCA suggested these compounds may bind within the same GBF1-Arf1 interfacial cleft. The GBF1 Sec7 domain was modeled in complex with Arf1 using the published structure of the Arf1-ARNO-BFA complex 35. When ARNO-Arf1 and GBF1-Arf1 complexes were compared, the BFA-binding region of this pocked was virtually identical. However, docking of GCA into this pocket revealed the compound to extend past the BFA binding region to the vicinity of a GBF1 tripeptide loop that does not exist in other ArfGEFS and therefore differs from ARNO, BIG1 or BIG2.

Figure 15:
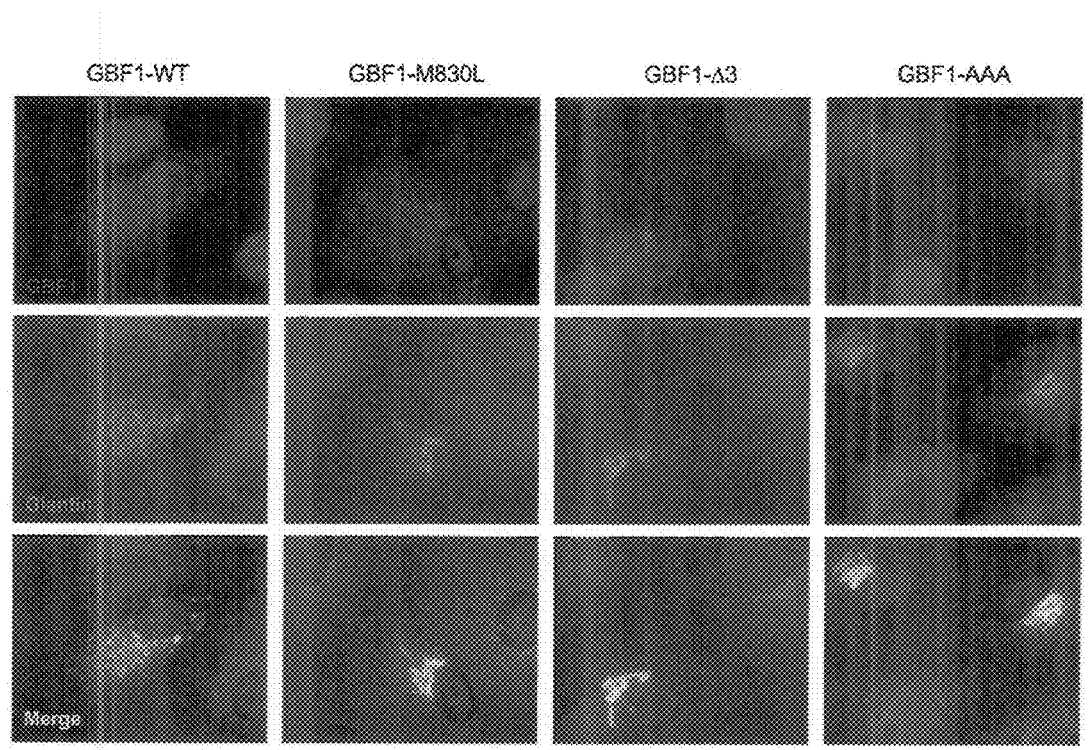
FIG. 15 is a series of photomicrographs showing that mutagenesis of the tripeptide, either by deletion of the three residues, or alteration to three alanine residues, results in resistance to GCA.

The contribution of the GBF1 tripeptide extension to GCA susceptibility was investigated by mutagenesis. Expression of GBF1-ML but not GBF1-loop mutants results in resistance to the effects of BFA on Golgi morphology. Vero cells were transiently transfected with GBF1-WT, or a GBF1-R843A, GBF1-K844A, GBF1-Q845A, or GBF1-N846A. Thirty-six hours later the cells were treated for 60 minutes with GCA (10 mM), the fixed and labeled with anti-HA epitope (GBF1; red) or giantin (green). Deletion of the entire tripeptide (Δ3), or mutagenesis of the three residues to alanine (-AAA) resulted in resistance to GCA, as indicated by the ability of these mutants to protect Golgi morphology in the presence of GCA (FIG. 15).

The mutants also maintained transport of tsVSVG-GFP to the plasma membrane in the presence of GCA. FIG. 16 is a series of photomicrographs showing that expression of GBF1-ML or GBF1-loop mutants results in resistance of the effects of GCA on is VSVG-GFP transport. Vero cells were co-transfected with tsVSVG-GFP and either GBF1-WT or a GBF1-mutant. One day after transfection the cells were incubated for 12 hrs at 42° C. to arrest VSVG-GFP in the endoplasmic reticulum. The cells were treated with GCA (10 mM) for 30 mins then shifted to 32° C. and incubated 4 hrs. The cells were then fixed and labeled with anti-HA (red) antibodies. Whereas expression of GBF1-WT fails to rescue VSVG-GFP transport in the presence of GCA, GBF1-ML and the GBF1-loop mutants are resistant to the effects of GCA.

However, as expected, these mutants remained susceptible to BFA, as this loop lies outside the BFA-binding pocket and not be expected to contribute to BFA susceptibility (FIG. 17). Expression of GBF1-ML but not GBF1-loop mutants results in resistance to the effects of BFA on Golgi morphology. Vero cells were transiently transfected with GBF1-WT, or a GBF1-ML, GBF1-D3, GBF1-AAA. Two days later the cells were treated for 60 mins with BFA (10 mg/ml) then fixed and labeled with anti-HA (GBF1; red) or anti-giantin antibodies (green). Cells expressing GBF1-ML, but not GBF1-WT, GBF1-D3, or GBF1-AAA are resistant to the effects of BFA on Golgi morphology.

Mutagenesis of individual residues around the tripeptide extension revealed that arginine 843, glutamate 845 and asparagine 846 were required for susceptibility to GCA while none of these residues were required for BFA susceptibility (FIG. 18). Expression of GBF1-ML but not GBF1-loop mutants results in resistance to the effects of BFA on Golgi morphology. Vero cells were transiently transfected with GBF1-WT, or a GBF1-R843A, GBF1-K844A, GBF1-Q845A, or GBF1-N846A. Thirty-six hours later the cells were treated for 60 mins with GCA (10 mM) then fixed and labeled with anti-HA epitope (GBF1; red) or giantin (green). Thus, cells expressing GBF1-R843A, GBF1-Q845A, and GBF1-N846A are resistant to the effects of GCA on Golgi morphology, whereas cells expressing GBF1-WT and GBF1-K844A are only partially protected. White asterisks mark the partially protected cells. Lysine 845, which protrudes from the opposite side of the GBF1 loop was not required for GCA susceptibility. In summary, these results reveal that the specificity of GCA for GBF1 resides within a tripeptide found within the GBF1 Sec7 domain and lacking from the Sec7 domain of other ArfGEFs.

Example 8

Inhibition of GBF1 Function Arrests Secretion of Soluble and Membrane-Anchored Proteins Having demonstrated that GCA was a specific inhibitor of GBF1 function, GCA was used to examine the role of GBF1 in secretory transport. Previous studies with a dominant-inactive mutant indicated that GBF1 function was required for maturation of ER-Golgi intermediate vesicles to a transport-competent state. Recent studies with siRNA-mediated inhibition suggested that GBF1 was required for anterograde transport of membrane-anchored cargo but was not required for secretion of soluble molecules.

To assess the role of GBF1 in secretion of membrane-anchored proteins, we examined the effect of GCA on transport of a GFP-tagged temperature-sensitive VSV-G protein (tsVSVG-GFP). At the non-permissive temperature of 40° C., this protein is retained and accumulates in the ER. Following a shift to the permissive temperature (32° C.), tsVSVG-GFP transits through the ERGIC to the Golgi and ultimately to the plasma membrane.

Figure 19:
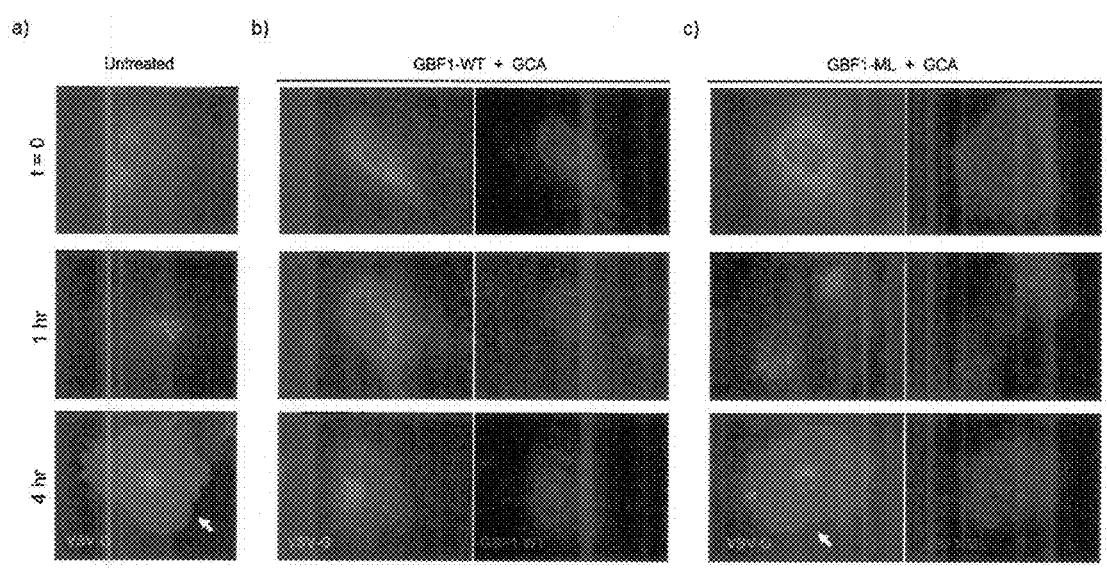
FIGS. 19A, B and C are a series of photomicrographs of immunofluorescence results obtained in GCA-treated Vero cells co-transfected with GFP-tagged tsVSVG and (19A) no additional plasmid, (19B) GBF1-WT or (19C) GBF1-ML.
Figure 20:
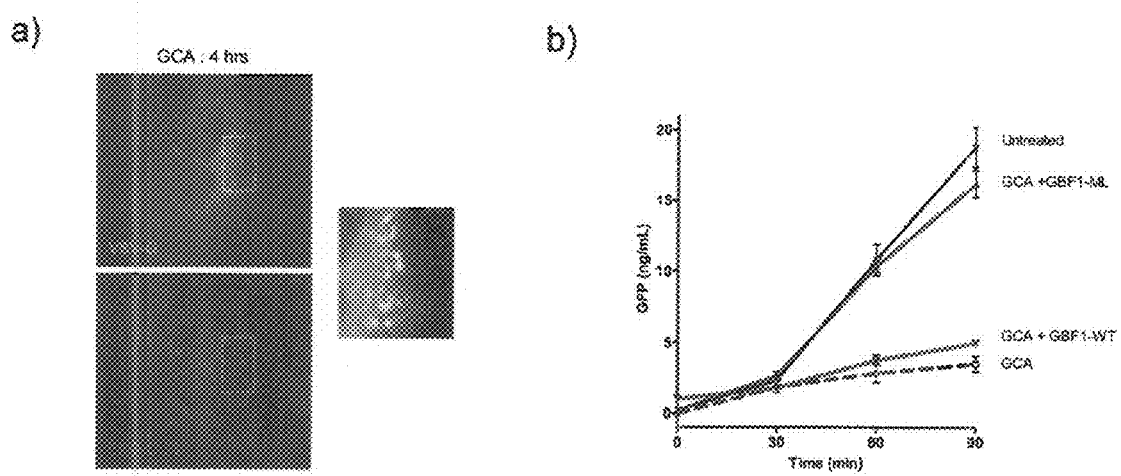
FIGS. 20A and B are (20A) a series of photomicrographs showing tsVSVG-GFP co-localizing with ERGIC53 in Vero cells treated with GCA, and (20B) a graph showing that exposure of cells to GCA inhibits secretion of soluble cargo.

To monitor the secretion of soluble cargo proteins, we expressed GFP bearing a neuropeptide Y secretion signal (NPY-GFP). This protein is secreted from Vero cells with a half life of approximately 60 min as judged by pulse chase experiments. Vero cells expressing NPY-GFP demonstrated markedly decreased GFP secretion in the presence of GCA. If inhibition of NPY-GFP secretion in GCA-treated cells was solely due to the inhibition of GBF1 function, then expression of the GCA-resistant GBF1-M832L mutant should restore protein secretion to levels seen with untreated cells. Therefore, the effect of expressing GBF1-WT or GBF1-ML on GFP secretion was assessed in GCA-treated cells. FIGS. 19 and 20 show the results obtained when cells were transfected either with tsVSVG-GFP alone or co-transfected with plasmid encoding GBF1-WT or GBF1-M832L, and the fate of tsVSV-G was followed in GCA-treated cells. FIG. 19A shows results obtained when cells were transfected with GFP-tagged tsVSVG, incubated with ERGIC53, then fixed, labeled with anti-ERGIC53 antibodies (red) and visualized by epifluoresence microscopy. In untreated cells, tsVSVG-GFP was transported from the ER to Golgi within 60 mins and was located predominantly at the plasma membrane by 4 hrs. GCA treatment, however, caused tsVSVG-GFP to be partially retained in a reticular, ER-like distribution and was also found in diffuse punctate structures (FIGS. 19B and 20A). Thus, whereas cells transduced with GBF1-WT failed to secrete NPY-GFP (FIG. 19B), the expression of NPY-GFP was restored to normal levels (FIG. 19A) in cells expressing GBF1-M832L (FIG. 19C). These data indicate that GBF1 function is required for secretion of both soluble and membrane-associated cargo. FIG. 20B shows a graph of GFP secretion over time in cells transduced either with adenovirus expressing NPY-GFP alone or co-transduced with NPY-GFP plus adenovirus expressing GBF1-WT or GBF1-M832L. GBF1-WT overexpression did not overcome the block in tsVSVG-GFP secretion in GCA-treated cells whereas co-transfection with GBF1-M832L restored tsVSVG-GFP transport to the plasma membrane (see also FIG. 19C).

GCA treatment did not completely block tsVSVG-GFP transport from the ER, as this protein was also found in peripheral punctate structures after 60 min incubation. These structures were identified as the ER-Golgi intermediate compartment by their labeling with anti-ERGIC53, indicating that tsVSVG-GFP was capable of transport from the ER to the ERGIC in cells lacking GBF1 function (FIG. 20A).

Example 9

Inhibition of GBF1 Function Impairs Retrograde Toxin Transport

As described in Example 2 above and in FIG. 7, the role of GBF1 in endocytic and retrograde transport pathways was assessed by tracking the fate of cholera toxin B subunit (CtxB), shiga toxin (Stx) and transferrin (Tfn). These ligands bind to receptors at the plasma membrane and are transported in retrograde direction to recycling endosomes. From there, Tfn recycles back to the plasma membrane, while CtxB and Stx are transported from endosomes to the TGN, through the Golgi to the ER. GCA treatment was shown not to affect endocytic transport to recycling endosomes. Referring again to FIG. 7, Vero cells were treated for 15 min with DMSO or GCA (10 µM) then incubated with AlexaFluor 594-labeled cholera toxin B subunit and 488-labeled transferrin, then fixed and developed for immunofluorescence as also described above. GCA treatment did not affect the transport of Ctx or Tfn to perinuclear recycling endosomes (FIG. 7A) nor did it affect the rate of Tfn recycling to the plasma membrane (FIG. 7B). These results indicate that GBF1 function is not required for transport through endocytic transport pathways.

Figure 21:
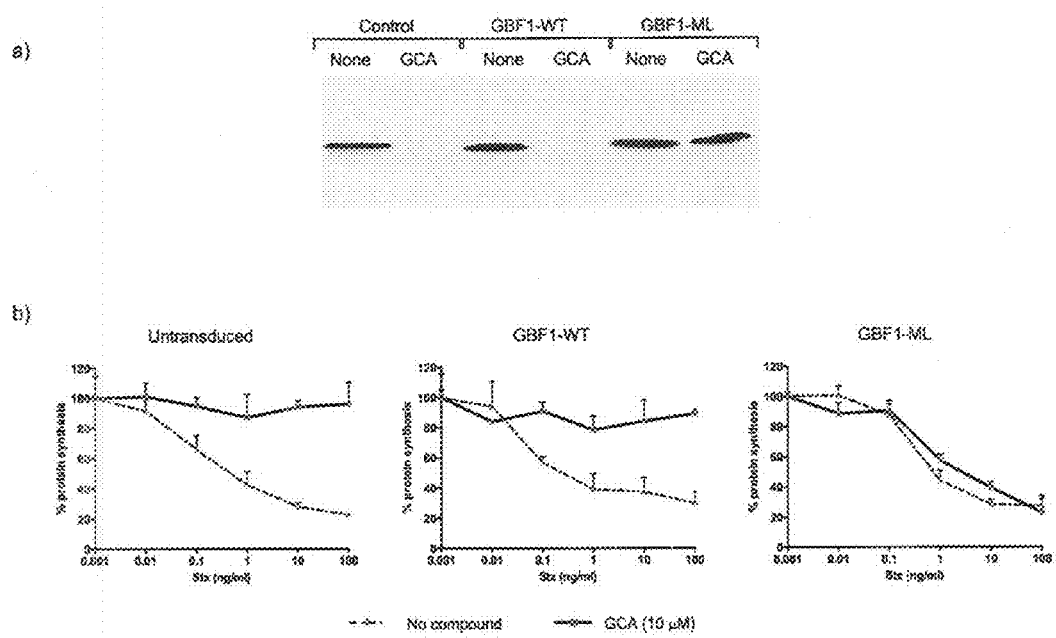
FIGS. 21A and B show (21A) comparative effects of GCA and BFA on cellular protein trafficking using sulfation of an StxB construct with a tandem of sulfation sites (StxB-SS) in untransduced Vero cells (control) or cells expressing wild-type GBF1 (GBF1-WT), and (21B) results showing complete restoration of Stx susceptibility in GCA-treated cells also expressing GBF1-ML.

The effect of GCA on transport of Stx from endosomes to the TGN was also examined using Stx B subunit that bears overlapping tyrosine sulfation sites (StxB-SS). During its transport through the retrograde transport pathway, this protein is transported from endosomes to the TGN where it is sulfated by resident tyrosyl-protein sulfotransferases (TPST). However, treatment GCA resulted in marked attenuation of toxin sulfation. Expression of GBF1-WT failed to rescue the transport of StxB-SS to the TGN, while expression of GBF1-M832L completely restored toxin sulfation to control levels in GCA-treated cells (FIG. 21A). These results indicate that GBF1 function is required for toxin transport from endosomes to the TGN. GCA was identified in a high-throughput screen for its ability to inhibit the effects of Shiga toxin on mammalian cells. The data presented thus far indicate that retrograde toxin transport was arrested within the endocytic compartment. To determine whether the effects of GCA on toxin transport were due solely to GBF1 inhibition, the ability of GBF1-M832L to restore toxin susceptibility to GCA-treated cells was examined. Cells were transduced with appropriate GBF1 constructs and treated with GCA. Toxin susceptibility was highly attenuated in control cells and those transduced with GBF1-WT. In contrast, toxin susceptibility was fully restored to GCA-treated cells expressing GBF1-M832L, indicating that the effects of GCA on toxin susceptibility were solely due to GBF1 inhibition (FIG. 21B). Together, these results indicate that GBF1 function is not required for transport of bacterial toxins to recycling endosomes, but that ArfGEF is required for retrograde transport from endosomes to the TGN and Golgi.

REFERENCES

1. Adorini, L., Ullrich, S. J., Appella, E., and Fuchs, S. (1990). Inhibition by brefeldin A of presentation of exogenous protein antigens to MHC class II-restricted T cells. Nature 346, 63-66.

2. Boehm, M., Aguilar, R. C., and Bonifacino, J. S. (2001). Functional and physical interactions of the adaptor protein complex AP-4 with ADP-ribosylation factors (ARFs). Embo J 20, 6265-6276.
3. Boman, A. L., Zhang, C., Zhu, X., and Kahn, R. A. (2000). A family of ADP-ribosylation factor effectors that can alter membrane transport through the trans-Golgi. Mol Biol Cell 11, 1241-1255.
4. Bonifacino, J. S., and Glick, B. S. (2004). The mechanisms of vesicle budding and fusion. Cell 116, 153-166.
5. Cherfils, J., and Melancon, P. (2005). On the action of Brefeldin A on Sec7-stimulated membrane-recruitment and GDP/GTP exchange of Arf proteins. Biochemical Society transactions 33, 635-638.
6. Citterio, C., Vichi, A., Pacheco-Rodriguez, G., Aponte, A. M., Moss, J., and Vaughan, M. (2008). Unfolded protein response and cell death after depletion of brefeldin A-inhibited guanine nucleotide-exchange protein GBF1. Proc Natl Acad Sci USA.
7. Claude, A., Zhao, B. P., Kuziemsky, C. E., Dahan, S., Berger, S. J., Yan, J. P., Armold, A. D., Sullivan, E. M., and Melancon, P. (1999). GBF1: A novel Golgi-associated BFA-resistant guanine nucleotide exchange factor that displays specificity for ADP-ribosylation factor 5. J Cell Biol 146, 71-84.
8. Cohen, L. A., Honda, A., Varnai, P., Brown, F. D., Balla, T., and Donaldson, J. G. (2007). Active Arf6 recruits ARNO/cytohesin GEFs to the PM by binding their PH domains. Mol Biol Cell 18, 2244-2253.
9. Cole, N. B., Sciaky, N., Marotta, A., Song, J., and Lippincott-Schwartz, J. (1996). Golgi dispersal during microtubule disruption: regeneration of Golgi stacks at peripheral endoplasmic reticulum exit sites. Mol Biol Cell 7, 631-650.
10. De Matteis, M. A., and Morrow, J. S. (2001). ADP-ribosylation factor (ARF) as regulator of spectrin assembly at Golgi complex. Methods in enzymology 329, 405-416.
11. Dell'Angelica, E. G., Puertollano, R., Mullins, C., Aguilar, R. C., Vargas, J. D., Hartnell, L. M., and Bonifacino, J. S. (2000). GGAs: a family of ADP ribosylation factor-binding proteins related to adaptors and associated with the Golgi complex. J Cell Biol 149, 81-94.
12. di Campli, A., Valderrama, F., Babia, T., De Matteis, M. A., Luini, A., and Egea, G. (1999). Morphological changes in the Golgi complex correlate with actin cytoskeleton rearrangements. Cell motility and the cytoskeleton 43, 334-348.
13. Doms, R. W., Russ, G., and Yewdell, J. W. (1989). Brefeldin A redistributes resident and itinerant Golgi proteins to the endoplasmic reticulum. J Cell Biol 109, 61-72.
14. Donaldson, J. G., Honda, A., and Weigert, R. (2005). Multiple activities for Arf1 at the Golgi complex. Biochim Biophys Acta 1744, 364-373.
15. Donaldson, J. G., and Jackson, C. L. (2000). Regulators and effectors of the ARF GTPases. Curr Opin Cell Biol 12, 475-482.
16. Doray, B., Ghosh, P., Griffith, J., Geuze, H. J., and Kornfeld, S. (2002). Cooperation of GGAs and AP-1 in packaging MPRs at the trans-Golgi network. Science 297, 1700-1703.
17. Egea, G., Lazaro-Dieguez, F., and Vilella, M. (2006). Actin dynamics at the Golgi complex in mammalian cells. Curr Opin Cell Biol 18, 168-178.
18. El Meskini, R., Jin, L., Marx, R., Bruzzaniti, A., Lee, J., Emeson, R., and Mains, R. (2001). A signal sequence is sufficient for green fluorescent protein to be routed to regulated secretory granules. Endocrinology 142, 864-873.
19. Garcia-Mata, R., Szul, T., Alvarez, C., and Sztul, E. (2003). ADP-ribosylation factor/COPI-dependent events at the endoplasmic reticulum-Golgi interface are regulated by the guanine nucleotide exchange factor GBF1. Mol Biol Cell 14, 2250-2261.
20. Ghosh, P., and Kornfeld, S. (2004). The GGA proteins: key players in protein sorting at the trans-Golgi network. European journal of cell biology 83, 257-262.
21. Godi, A., Santone, I., Pertile, P., Devarajan, P., Stabach, P. R., Morrow, J. S., Di Tullio, G., Polishchuk, R., Petrucci, T. C., Luini, A., et al. (1998). ADP ribosylation factor regulates spectrin binding to the Golgi complex. Proc Natl Acad Sci USA 95, 8607-8612.
22. Guillemain, I., and Exton, J. H. (1997). Effects of brefeldin A on phosphatidylcholine phospholipase D and inositolphospholipid metabolism in HL-60 cells. European journal of biochemistry/FEBS 249, 812-819.
23. Helms, J. B., and Rothman, J. E. (1992). Inhibition by brefeldin A of a Golgi membrane enzyme that catalyses exchange of guanine nucleotide bound to ARF. Nature 360, 352-354.
24. Hirschberg, K., Miller, C. M., Ellenberg, J., Presley, J. F., Siggia, E. D., Phair, R. D., and Lippincott-Schwartz, J. (1998). Kinetic analysis of secretory protein traffic and characterization of golgi to plasma membrane transport intermediates in living cells. J Cell Biol 143, 1485-1503.
25. Holloway, Z. G., Grabski, R., Szul, T., Styers, M., Coventry, J., Monaco, A. P., and Sztul, E. (2007). Activation of ADP-ribosylation factor (Arf) regulates biogenesis of the ATP7A containing trans-Golgi network compartment and its Cu-induced trafficking. Am J Physiol Cell Physiol.
26. Hunziker, W., Whitney, J. A., and Mellman, I. (1991). Selective inhibition of transcytosis by brefeldin A in MDCK cells. Cell 67, 617-627.
27. Jackson, C. L. (2000). Brefeldin A revealing the fundamental principles governing membrane dynamics and protein transport. Subcell Biochem 34, 233-272.
28. Jones, H. D., Moss, J., and Vaughan, M. (2005). BIG1 and BIG2, brefeldin A-inhibited guanine nucleotide-exchange factors for ADP-ribosylation factors. Methods in enzymology 404, 174-184.
29. Kahn, R. A., Cherfils, J., Elias, M., Lovering, R. C., Munro, S., and Schurmann, A. (2006). Nomenclature for the human Alf family of GTP-binding proteins: ARF, ARL, and SAR proteins. J Cell Biol 172, 645-650.
30. Kawamoto, K., Yoshida, Y., Tamaki, H., Torii, S., Shinotsuka, C., Yamashina, S., and Nakayama, K. (2002). GBF1, a guanine nucleotide exchange factor for ADP-ribosylation factors, is localized to the cis-Golgi and involved in membrane association of the COPI coat. Traffic 3, 483-495.
31. Ktistakis, N. T., Brown, H. A., Sternweis, P. C., and Roth, M. G. (1995). Phospholipase D is present on Golgi-enriched membranes and its activation by ADP ribosylation factor is sensitive to brefeldin A. Proc Natl Acad Sci USA 92, 4952-4956.
32. Lazaro-Dieguez, F., Jimenez, N., Barth, H., Koster, A. J., Renau-Piqueras, J., Llopis, J. L., Burger, K. N., and Egea, G. (2006). Actin filaments are involved in the maintenance of Golgi cisternae morphology and intra-Golgi pH. Cell motility and the cytoskeleton 63, 778-791.
33. Lefrancois, S., and McCormick, P. J. (2007). The AlfGEF GBF1 is required for GGA recruitment to Golgi membranes. Traffic 8, 1440-1451.
34. Lin, W. H., Larsen, K., Hortin, G. L., and Roth, J. A. (1992). Recognition of substrates by tyrosylprotein sulfotransferase. Determination of affinity by acidic amino acids near the target sites. J Biol Chem 267, 2876-2879.

35. Lippincott-Schwartz, J., Donaldson, J. G., Schweizer, A., Berger, E. G., Hauri, H. P., Yuan, L. C., and Klausner, R. D. (1990). Microtubule-dependent retrograde transport of proteins into the ER in the presence of brefeldin A suggests an ER recycling pathway. Cell 60, 821-836.
36. Lippincott-Schwartz, J., Yuan, L., Tipper, C., Amherdt, M., Orci, L., and Klausner, R. D. (1991). Brefeldin A's effects on endosomes, lysosomes, and the TGN suggest a general mechanism for regulating organelle structure and membrane traffic. Cell 67, 601-616.
37. Lippincott-Schwartz, J., Yuan, L. C., Bonifacino, J. S., and Klausner, R. D. (1989). Rapid redistribution of Golgi proteins into the ER in cells treated with brefeldin A: evidence for membrane cycling from Golgi to ER. Cell 56, 801-813.
38. Liu, W., Duden, R., Phair, R. D., and Lippincott-Schwartz, J. (2005). ArfGAP1 dynamics and its role in COPI coat assembly on Golgi membranes of living cells. J Cell Biol 168, 1053-1063.
39. Mallard, F., Tang, B. L., Galli, T., Tenza, D., Saint-Pol, A., Yue, X., Antony, C., Hong, W., Goud, B., and Johannes, L. (2002). Early/recycling endosomes-to-TGN transport involves two SNARE complexes and a Rab6 isoform. Journal of Cell Biology 156, 653-664.
40. Manolea, F., Claude, A., Chun, J., Rosas, J., and Melancon, P. (2008). Distinct Functions for Arf Guanine Nucleotide Exchange Factors at the Golgi Complex: GBF1 and BIGs Are Required for Assembly and Maintenance of the Golgi Stack and trans-Golgi Network, Respectively. Mol Biol Cell 19, 523-535.
41. Mansour, S. J., Skaug, J., Zhao, X. H., Giordano, J., Scherer, S. W., and Melancon, P. (1999). p200 ARF-GEP1: a Golgi-localized guanine nucleotide exchange protein whose Sec7 domain is targeted by the drug brefeldin A. Proc Natl Acad Sci USA 96, 7968-7973.
42. Monetta, P., Slavin, I., Romero, N., and Alvarez, C. (2007). Rab1b interacts with GBF1 and modulates both ARF1 dynamics and COPI association. Mol Biol Cell 18, 2400-2410.
43. Mossessova, E., Corpina, R. A., and Goldberg, J. (2003). Crystal structure of ARF1 Sec7 complexed with Brefeldin A and its implications for the guanine nucleotide exchange mechanism. Mol Cell 12, 1403-1411.
44. Niehrs, C., and Huttner, W. B. (1990). Purification and characterization of tyrosylprotein sulfotransferase. Embo J 9, 35-42.
45. Niu, T. K., Pfeifer, A. C., Lippincott-Schwartz, J., and Jackson, C. L. (2005). Dynamics of GBF1, a Brefeldin A-sensitive Arf1 exchange factor at the Golgi. Mol Biol Cell 16, 1213-1222.
46. Orci, L., Tagaya, M., Amherdt, M., Perrelet, A., Donaldson, J. G., Lippincott-Schwartz, J., Klausner, R. D., and Rothman, J. E. (1991). Brefeldin A, a drug that blocks secretion, prevents the assembly of non-clathrin-coated buds on Golgi cisternae. Cell 64, 1183-1195.
47. Pacheco-Rodriguez, G., Moss, J., and Vaughan, M. (2002). BIG1 and BIG2: brefeldin A-inhibited guanine nucleotide-exchange proteins for ADP-ribosylation factors. Methods in enzymology 345, 397-404.
48. Pasqualato, S., Menetrey, J., Franco, M., and Cherfils, J. (2001). The structural GDP/GTP cycle of human Arf6. EMBO Rep 2, 234-238.
49. Peyroche, A., Antonny, B., Robineau, S., Acker, J., Cherfils, J., and Jackson, C. L. (1999). Brefeldin A acts to stabilize an abortive ARF-GDP-Sec7 domain protein complex: involvement of specific residues of the Sec7 domain. Mol Cell 3, 275-285.
50. Presley, J. F., Ward, T. H., Pfeifer, A. C., Siggia, E. D., Phair, R. D., and Lippincott-Schwartz, J. (2002). Dissection of COPI and Arf1 dynamics in vivo and role in Golgi membrane transport. Nature 417, 187-193.
51. Prydz, K., Hansen, S. H., Sandvig, K., and van Deurs, B. (1992). Effects of brefeldin A on endocytosis, transcytosis and transport to the Golgi complex in polarized MDCK cells. J Cell Biol 119, 259-272.
52. Reaves, B., and Banting, G. (1992). Perturbation of the morphology of the trans-Golgi network following Brefeldin A treatment: redistribution of a TGN-specific integral membrane protein, TGN38. J Cell Biol 116, 85-94.
53. Reaves, B., Horn, M., and Banting, G. (1993). TGN38/41 recycles between the cell surface and the TGN: brefeldin A affects its rate of return to the TGN. Mol Biol Cell 4, 93-105.
54. Renault, L., Christova, P., Guibert, B., Pasqualato, S., and Cherfils, J. (2002). Mechanism of domain closure of Sec7 domains and role in BFA sensitivity. Biochemistry 41, 3605-3612.
55. Renault, L., Guibert, B., and Cherfils, J. (2003). Structural snapshots of the mechanism and inhibition of a guanine nucleotide exchange factor. Nature 426, 525-530.
56. Rios, R. M., and Bornens, M. (2003). The Golgi apparatus at the cell centre. Curr Opin Cell Biol 15, 60-66.
57. Rios, R. M., Sanchis, A., Tassin, A. M., Fedriani, C., and Bornens, M. (2004). GMAP-210 recruits gamma-tubulin complexes to cis-Golgi membranes and is required for Golgi ribbon formation. Cell 118, 323-335.
58. Robinson, M. S. (2004). Adaptable adaptors for coated vesicles. Trends Cell Biol 14, 167-174.
59. Saenz, J. B., Doggett, T. A., and Haslam, D. B. (2007). Identification and characterization of small molecules that inhibit intracellular toxin transport. Infection and immunity 75, 4552-4561.
60. Sanchez, R. M., Vervoordeldonk, M. J., Schalkwijk, C. G., and van den Bosch, H. (1993). Prevention of the induced synthesis and secretion of group II phospholipase A2 by brefeldin A. FEBS Lett 332, 99-104.
61. Sandvig, K., Prydz, K., Hansen, S. H., and van Deurs, B. (1991). Ricin transport in brefeldin A-treated cells: correlation between Golgi structure and toxic effect. J Cell Biol 115, 971-981.
62. Santy, L. C., and Casanova, J. E. (2001). Activation of ARF6 by ARNO stimulates epithelial cell migration through downstream activation of both Rac1 and phospholipase D. J Cell Biol 154, 599-610.
63. Shen, X., Hong, M. S., Moss, J., and Vaughan, M. (2007). BIG1, a brefeldin A-inhibited guanine nucleotide-exchange protein, is required for correct glycosylation and function of integrin beta1. Proc Natl Acad Sci USA 104, 1230-1235.
64. Shewan, A. M., van Dam, E. M., Martin, S., Luen, T. B., Hong, W., Bryant, N. J., and James, D. E. (2003). GLUT4 recycles via a trans-Golgi network (TGN) subdomain enriched in Syntaxins 6 and 16 but not TGN38: involvement of an acidic targeting motif. Mol Biol Cell 14, 973-986.
65. Shinotsuka, C., Waguri, S., Wakasugi, M., Uchiyama, Y., and Nakayama, K. (2002a). Dominant-negative mutant of BIG2, an ARF-guanine nucleotide exchange factor, specifically affects membrane trafficking from the trans-Golgi network through inhibiting membrane association of AP-1 and GGA coat proteins. Biochemical and biophysical research communications 294, 254-260.
66. Shinotsuka, C., Yoshida, Y., Kawamoto, K., Takatsu, H., and Nakayama, K. (2002b). Overexpression of an ADP- 66. (cont.) ribosylation factor-guanine nucleotide exchange factor, BIG2, uncouples brefeldin A-induced adaptor protein-1 coat dissociation and membrane tubulation. J Biol Chem 277, 9468-9473.
67. Shmuel, M., Santy, L. C., Frank, S., Avrahami, D., Casanova, J. E., and Altschuler, Y. (2006). ARNO through its coiled-coil domain regulates endocytosis at the apical surface of polarized epithelial cells. J Biol Chem 281, 13300-13308.
68. Siddhanta, A., Radulescu, A., Stankewich, M. C., Morrow, J. S., and Shields, D. (2003). Fragmentation of the Golgi apparatus. A role for beta III spectrin and synthesis of phosphatidylinositol 4,5-bisphosphate. J Biol Chem 278, 1957-1965.
69. Silletta, M. G., Di Girolamo, M., Fiucci, G., Weigert, R., Mironov, A., De Matteis, M. A., Luini, A., and Gorda, D. (1997). Possible role of BARS-50, a substrate of brefeldin A-dependent mono-ADP-ribosylation, in intracellular transport. Advances in experimental medicine and biology 419, 321-330.
70. Stoorvogel, W., Oorschot, V., and Geuze, H. J. (1996). A novel class of clathrin-coated vesicles budding from endosomes. J Cell Biol 132, 21-33.
71. Szul, T., Garcia-Mata, R., Brandon, E., Shestopal, S., Alvarez, C., and Sztul, E. (2005). Dissection of membrane dynamics of the ARF-guanine nucleotide exchange factor GBF1. Traffic 6, 374-385.
72. Szul, T., Grabski, R., Lyons, S., Morohashi, Y., Shestopal, S., Lowe, M., and Sztul, E. (2007). Dissecting the role of the ARF guanine nucleotide exchange factor GBF1 in Golgi biogenesis and protein trafficking. J Cell Sci 120, 3929-3940.
73. Tamura, G., Ando, K., Suzuki, S., Takatsuki, A., and Arima, K. (1968). Antiviral activity of brefeldin A and verrucarin A. The Journal of antibiotics 21, 160-161.
74. Thyberg, J., and Moskalewski, S. (1999). Role of microtubules in the organization of the Golgi complex. Exp Cell Res 246, 263-279.
75. Traub, L. M., Ostrom, J. A., and Kornfeld, S. (1993). Biochemical dissection of AP-1 recruitment onto Golgi membranes. J Cell Biol 123, 561-573.
76. Valderrama, F., Duran, J. M., Babia, T., Barth, H., Renau-Piqueras, J., and Egea, G. (2001). Actin microfilaments facilitate the retrograde transport from the Golgi complex to the endoplasmic reticulum in mammalian cells. Traffic 2, 717-726.
77. van Dam, E. M., and Stoorvogel, W. (2002). Dynamin-dependent transferrin receptor recycling by endosome-derived clathrin-coated vesicles. Mol Biol Cell 13, 169-182.
78. van Kerkhof, P., Lee, J., McCormick, L., Tetrault, E., Lu, W., Schoenfish, M., Oorschot, V., Strous, G. J., Klumperman, J., and Bu, G. (2005). Sorting nexin 17 facilitates LRP recycling in the early endosome. Embo J 24, 2851-2861.
79. Wood, S. A., Park, J. E., and Brown, W. J. (1991). Brefeldin A causes a microtubule-mediated fusion of the trans-Golgi network and early endosomes. Cell 67, 591-600.
80. Yang, J. S., Lee, S. Y., Spano, S., Gad, H., Zhang, L., Nie, Z., Bonazzi, M., Gorda, D., Luini, A., and Hsu, V. W. (2005). A role for BARS at the fission step of COPI vesicle formation from Golgi membrane. Embo J 24, 4133-4143.
81. Yoon, H. Y., Bonifacino, J. S., and Randazzo, P. A. (2005). In vitro assays of Arf1 interaction with GGA proteins. Methods in enzymology 404, 316-332.
82. Yoshida, T., Chen, C. C., Zhang, M. S., and Wu, H. C. (1991). Disruption of the Golgi apparatus by brefeldin A inhibits the cytotoxicity of ricin, modeccin, and *Pseudomonas* toxin. Exp Cell Res 192, 389-395.
83. Zeeh, J. C., Zeghouf, M., Grauffel, C., Guibert, B., Martin, E., Dejaegere, A., and Cherfils, J. (2006). Dual specificity of the interfacial inhibitor brefeldin a for arf proteins and sec7 domains. J Biol Chem 281, 11805-11814.
84. Zhao, L., and Haslam, D. B. (2005). A quantitative and highly sensitive luciferase-based assay for bacterial toxins that inhibit protein synthesis. Journal of Medical Microbiology 54, 1023-1030.
85. Zhao, X., Claude, A., Chun, J., Shields, D. J., Presley, J. F., and Melancon, P. (2006). GBF1, a cis-Golgi and VTCs-localized ARF-GEF, is implicated in ER-to-Golgi protein traffic. J Cell Sci 119, 3743-3753.
86. Zhao, X., Lasell, T. K., and Melancon, P. (2002). Localization of large ADP-ribosylation factor-guanine nucleotide exchange factors to different Golgi compartments: evidence for distinct functions in protein traffic. Mol Biol Cell 13, 119-133.

The invention claimed is:

1. A method of inhibiting Golgi BFA resistance factor (GBF1) in a eukaryotic cell, the method comprising contacting the cell with Golgicide A.

2. The method of claim 1, wherein contacting the cell with Golgicide A comprises contacting the cell with a solution of Golgicide A in an organic solvent.

3. The method of claim 2, wherein the organic solvent is DMSO.

4. The method of claim 2, wherein the solution of Golgicide A comprises Golgicide A at a concentration of from about 0.1 µM to about 100 µM.

5. The method of claim 4, wherein the solution of Golgicide A comprises Golgicide A at a concentration of from about 5 µM to about 20 µM.

6. The method of claim 1, wherein the eukaryotic cell is a mammalian cell.

7. The method of claim 1, wherein the eukaryotic cell is a human cell.

8. The method of claim 1, further comprising exposing the cell to a cytotoxin selected from the group consisting of: shiga toxin, cholera toxin, heat labile toxin, heat stable toxin, abrin, and ricin.

9. The method of claim 1, further comprising at least partially reversing the effect of Golgicide A on GBF1 by washout of Golgicide A with a cell medium lacking Golgicide A.

* * * * *